(12) United States Patent
Schrock et al.

(10) Patent No.: US 9,701,702 B2
(45) Date of Patent: *Jul. 11, 2017

(54) METATHESIS CATALYSTS AND METHODS THEREOF

(71) Applicant: Massachusetts Institute of Technology, Cambridge, MA (US)

(72) Inventors: Richard Royce Schrock, Winchester, MA (US); Michael R. Reithofer, Vienna (AT)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/961,346

(22) Filed: Dec. 7, 2015

(65) Prior Publication Data

US 2016/0229877 A1 Aug. 11, 2016

Related U.S. Application Data

(62) Division of application No. 14/255,290, filed on Apr. 17, 2014, now Pat. No. 9,206,211.

(60) Provisional application No. 61/813,096, filed on Apr. 17, 2013.

(51) Int. Cl.

| | | |
|---|---|---|
| *C07F 11/00* | (2006.01) | |
| *C07C 6/04* | (2006.01) | |
| *B01J 31/22* | (2006.01) | |
| *C07D 207/325* | (2006.01) | |
| *C08F 132/08* | (2006.01) | |
| *C07D 403/10* | (2006.01) | |
| *C08G 61/08* | (2006.01) | |

(52) U.S. Cl.
CPC .......... *C07F 11/00* (2013.01); *B01J 31/2265* (2013.01); *C07C 6/04* (2013.01); *C07D 207/325* (2013.01); *C07D 403/10* (2013.01); *C08F 132/08* (2013.01); *C08G 61/08* (2013.01); *B01J 2231/543* (2013.01); *B01J 2531/64* (2013.01); *B01J 2531/66* (2013.01); *C07C 2531/22* (2013.01); *C08G 2261/11* (2013.01); *C08G 2261/1426* (2013.01); *C08G 2261/418* (2013.01)

(58) Field of Classification Search
CPC .......... C07F 11/00; C07C 6/04; B01J 31/2265
See application file for complete search history.

(56) References Cited

U.S. PATENT DOCUMENTS

| | | | |
|---|---|---|---|
| 6,121,473 A | 9/2000 | Schrock et al. | |
| 7,932,397 B2 | 4/2011 | Hock et al. | |
| 8,222,469 B2 | 7/2012 | Schrock et al. | |
| 8,350,073 B2 | 1/2013 | Hock et al. | |
| 8,362,311 B2 | 1/2013 | Schrock et al. | |
| 8,546,500 B2 | 10/2013 | Hoveyda et al. | |
| 8,598,400 B2 | 12/2013 | Hoveyda | |
| 8,829,219 B2 | 9/2014 | Hock et al. | |
| 9,073,801 B2 | 7/2015 | Hoveyda et al. | |
| 2011/0015430 A1 | 1/2011 | Schrock et al. | |
| 2011/0065915 A1 | 3/2011 | Malcolmson et al. | |
| 2011/0077421 A1 | 3/2011 | Schrock et al. | |
| 2011/0237815 A1 | 9/2011 | Hock et al. | |
| 2011/0245477 A1 | 10/2011 | Hoveyda et al. | |
| 2012/0302710 A1 | 11/2012 | Hoveyda et al. | |
| 2012/0323000 A1 | 12/2012 | Hoveyda et al. | |
| 2013/0116434 A1 | 5/2013 | Schrock et al. | |
| 2013/0274482 A1 | 10/2013 | Schrock et al. | |
| 2013/0281706 A1 | 10/2013 | Hock et al. | |
| 2014/0309388 A1 | 10/2014 | Schrock et al. | |
| 2014/0330018 A1 | 11/2014 | Czirok et al. | |
| 2014/0378637 A1 | 12/2014 | Schrock et al. | |
| 2015/0065723 A1 | 3/2015 | Hock et al. | |

FOREIGN PATENT DOCUMENTS

| | | |
|---|---|---|
| DE | 19541146 | 4/1997 |
| EP | 2239263 | 10/2010 |
| WO | 2012167171 | 12/2012 |

OTHER PUBLICATIONS

International Search Report and Written Opinion dated Jul. 16, 2014 for PCT/US2014/034487.
Addison, et al., "Synthesis, Structure, and Spectroscopic Properties of Copper (II) Compounds Containing Nitrogen-Sulphur donor Ligands: The Crystal and Molecular Structure of Aqua[1,7-bis(N-methylbenzimidazol-2'-yl)-2,6-dithiaheptane]copper(II) Perchlorate", J Chem Soc., Dalton Trans., 1984, 1349-1356.
Ballesteros, et al., "Reaction of Pyrazole Addition to Quinones", Database CA [online] 9, 10 Chemical Abstracts Service, Columbus, Ohio, US, XP002726318, retrieved from STN database accession No. 1992:128755 abstract.
Ballesteros, et al., "Reaction of Pyrazole Addition to Quinones", The Journal of Organic Chemistry, 57(6), 1992, 1873-1876.
Claramunt, et al., "Electrochemical Behavior of Substituted Hydroqinones", Chemical Abstract Service, ZP002726319, retrieved from STN Database No. 1995:752321 Abstract, 1995.
Couzijn, et al., "Steromutation of Pentavalent Compounds: Validating the Berry Pseudorotation, Redressing Ugi's Turnstile Rotation, and Revealing the Two- and Three-Arm Turnstiles", Journal of American Chemical Society, 132, 2010, 18127-18140.
Dickie, et al., "Synthesis of the Bulky M-Terphenyl Phenol Ar*OH (Ar*=C6H3-2,6-Mes2, Mes=2,4,6-Trimethylphenyl) and the Preparation and Structural Characterization of Several of its Metal Complexes", Canadian Journal of Chemistry, 86, 2008, 20-31.
Elsevier, Database Reaxys [online] Elsevier; 2010, XRN=20772536: XP002726321, database accession No. XRN=20772536 abstract.
Flook, et al., "Z-Selective and Syndioselective Ring-Opening Metathesis Polymerization (ROMP) Initiated by Monoaryloxidepyrrolide (MAP) Catalysts", Micromolecule, 43, 2010, 7515-7522.

(Continued)

Primary Examiner — Caixia Lu
(74) Attorney, Agent, or Firm — Stoel Rives LLP

(57) ABSTRACT

The present invention provides, among other things, novel compounds and methods for metathesis reactions. In some embodiments, a provided compound has the structure of formula I or II. In some embodiments, the present invention provides compounds and methods for Z-selective olefin metathesis.

14 Claims, 5 Drawing Sheets

(56) References Cited

OTHER PUBLICATIONS

Flook, et al., "Z-Selective Olefin Metathesis Processes Catalyzed by a Molybdenum Hexaisopropyltenphenoxide Momopyrrolide Complex", J Am Chem Soc., 131(23), 2009, 7962-7963.

Hock, et al., "Dipyrrolyl Precursors to Bisalkoxide Molybdenum Olefin Metathesis Catalysts", J Am Chem Soc., 128(50), 2006, 16373-16375.

Hoelscher, et al., "Preparation of 1-Phenylimidazoles as Nitric Oxide Synthase Inhibitors", Chemical Abstracts Services, ZP002726320, retrieved from STN Database No. 1997:389124, 1997.

Ibrahem, et al., "Highly Z- and Enantioselective Ring-Opening/ Cross-Metathesis Reactions Catalyzed by Stereogenic-at-Mo Adamantylimido Complexes", J Am Chem Soc., 131(11), 2009, pp. 3844-3845.

Ito, et al., "Reaction of Ketone Enolates with Copper Dichloride a Synthesis of 1,4-Diketones", Journal of the American Chemical Society, 97(10), 1975, 2912-2914.

Jiang, "Fundamental Studies of Tungsten Alkylidene Imido Monoalkoxidepyrrolide Complexes", J Am Chem Soc., 131(22), 2009, 7770-7780.

Jiang, et al., "Highly Z-Selective Metathesis Homocoupling of Terminal Olefins", J Am Chem Soc., 131(46), 2009, 16630-16631.

Kreickmann, et al., "Imido alkylidene Bispyrrolyl Complexes of Tungsten", Organometallics, 26, 2007, 5702-5711.

Marinescu, et al., "Room-Temperature Z-Selective Homocoupling of a-Olefins by Tungsten Catalysts", Organometallics, 30, 2011, 1780-1782.

Moberg, "Stereomutation in Trigonal-Bipyramidal Systems: A Unified Picture", Angewandte Chemie International Edition, 50, 2011, 10290-10292.

Muller, "Practical Suggestions for Better Crystal Structures", Crysatllography Reviews, 15(1), 2009, 57-83.

Poater, et al., "Understanding D(0)-Olefin Metathesis CatalystsL Which Metal, Which Legands?", J Am Chem Soc., 129(26), E pub Jun. 9, 2007, Jul. 4, 2007, 8207-8216.

Reithofer, et al., "Monoaryloxide Pyrrolide (MAP) Imido Alkylidene Complexes of Molybdenum and Tundsten that Contain 2,6-Bis(2,5-R 2-Pyrrolyl) Phenoxide (R . i-Pr, Ph) Ligands and an Unsubstituted Metallacyclobutane on its Way to Losing Ethylene", Organometallics, 32(9), 2013, 2489-2492.

Schrock, et al., Notice of Allowance dated Jul. 31, 2015 for U.S. Appl. No. 14/255,290.

Schrock, et al., "Fundamental Studies of Molybdenum and Tungsten Methylidene and Metallacyclobutane Complexes", Organometallics, 29, 2010, 5241-5251.

Sheldrick, et al., "A Short History of SHELX", Acta Crystallographica A, 64(pt1), 2008, 112-122.

Sheldrick, "Phase Annealing in SHELX-90: Direct Methods for Larger Structures", Acta Crystallographica, A46, 1990, 467-473.

Sienkowska, et al., "Preparation and NMR Analysis of 2,6-Heterodifunctional Halobenzenes as Precursors for Sumstituted Biphenyls", Tetrahedron, 56, 2000, 165-173.

Solans-Monfort, et al., "d0 Re-Based Olefin Metathesis Catalysts, RE(=CR)(=CHR)(X)(Y): The Key Role of X and Y Ligands for Efficient Active Sites", J Am Chem Soc., 127(40), 2005, 14015-14025.

Solans-Monfort, et al., "Oxo vs Imido Alkylidene d0-Metal Species: How and Why Do They Differ in Structure, Activity, and Efficiency in Alkene Metathesis?,", Organometallics, 31, 2012, 6812-6822.

Solans-Monfort, et al., "Shutting Down Secondary Reaction Pathways: The Essential Role of the Pyrrolyl Ligand in Improving Silica Supported d0-ML4 Alkene Metathesis Catalysts from DFT Calculations", Journal of the American Chemical Society, 132, 2010, 7750-7757.

Stanciu, et al., "Synthesis and Characterization of the very Bulky Phenols Ar*OH and Ar'OH (Ar*=C6H3-2,6- Trip2, Trip=C6H2-2,4,6-iPr3; Ar'=C6H3-2,6-Dipp2, Dipp=C6H3-2,6-iPr2) and Their Lithium and Sodium Derivatives (Li OAr')2", European Journal of Inorganic Chemistry, 2003, 3495-3500.

Tabor, et al., "Regioselective Catalytic Transfer Hydrogenation of Dimethyl Bicycle[2.2. 1] hepta-2,5-Diene-2,3-Dicarboxylate, Dimethyl Bicycle[2.2.1]Hept-2-Ene-2,3-Dicargoxylate, and Related Compounds Over Palladium on Carbon", Journal of Organic Chemistry, 48, 1983, 1638-1643.

Wang, et al., "Molybdenum-Based Complexes with Two Aryloxides and a Pentafluoroimido Ligand: Catalysts for Efficient Z-Selective Synthesis of a Macrocyclic Trisubstituted alkene by Ring-Closing Metathesis", Angew Chem Int Ed Engl, 52(7), 2013, 1939-1943.

Yuan, et al., "Pentafluorophenylimido Alkylidene Complexes of Molybdenum and Tungsten", Organometallics, 31, 2012, 4650-4653.

Yuan, et al., "Preparation of Tungsten-Based Olefin Metathesis Catalysts Supported on Alumina", Adv. Synth. Catal., 353, 2011, 1985-1992.

Five TBP Structures     SP structure

METATHESIS CATALYSTS AND METHODS THEREOF

CROSS-REFERENCE TO RELATED APPLICATIONS

The present application claims priority to U.S. Provisional Application Ser. No. 61/813,096, filed Apr. 17, 2013, the entirety of which is incorporated herein by reference.

STATEMENT REGARDING FEDERALLY SPONSORED RESEARCH OR DEVELOPMENT

This invention was made with government support under Grant Nos. CHE1111133 and CHE1205189 awarded by the National Science Foundation. The government has certain rights in the invention.

FIELD OF THE INVENTION

The present invention generally relates to metathesis reactions.

BACKGROUND

Catalytic olefin metathesis has transformed chemical synthesis and offers exceptionally efficient pathways for synthesis of alkenes. In the last several years sterically demanding phenoxide ligands have been employed to make Mo- and W-based MAP (MonoAlkoxide Pyrrolide) catalysts for olefin metathesis reactions. One of the first was $OBr_2Bitet$, an enantiomerically pure monophenoxide ligand that yielded diastereomeric mixtures of MAP catalysts (R'=H or Me) for enantioselective ring-opening/cross-metathesis reactions (Ibrahem, I; Yu, M.; Schrock, R. R.; Hoveyda, A. H. *J. Am. Chem. Soc.* 2009, 131, 3844).

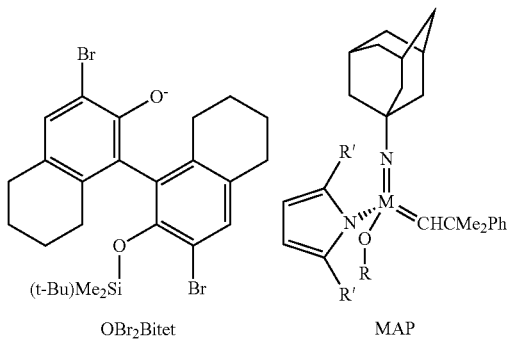

OBr₂Bitet                MAP

In the process, it was found that the reaction was not only enantioselective but also Z-selective. The search for other suitable sterically demanding phenoxides led to terphenoxides such as $O-2,6-(2,4,6-i-Pr_3C_6H_2)_2C_6H_3$ (OHIPT)(Stanciu, C.; Olmstead, M. M.; Phillips, A. D.; Stender, M.; Power, P. P. *Eur. J. Inorg. Chem.* 2003, 3495) and $O-2,6$-Mesityl$_2C_6H_3$ (OHMT) (Dickie, D. A.; MacIntosh, I. S.; Ino, D. D.; He, Q.; Labeodan, O. A.; Jennings, M. C.; Schatte, G.; Walsby, C. J.; Clyburne, J. A. C. *Can. J. Chem.* 2008, 86, 20), which were employed to produce Z-selective catalysts for ROMP ((a) Flook, M. M.; Jiang, A. J.; Schrock, R. R.; Müller, P.; Hoveyda, A. H. *J. Am. Chem. Soc.* 2009, 131, 7962. (b) Flook, M. M.; Gerber, L. C. H.; Debelouchina, G. T.; Schrock, R. R. *Macromolecules* 2010, 43, 7515) and homocoupling of terminal olefins ((a) Jiang, A. J.; Zhao, Y.; Schrock, R. R.; Hoveyda, A. H. *J. Am. Chem. Soc.* 2009, 131, 16630. (b) Marinescu, S. C.; Schrock, R. R.; Müller, P.; Takase, M. K.; Hoveyda, A. H. *Organometallics* 2011, 30, 1780). Decafluoroterphenoxide $(O-2,6-(C_6F_5)_2C_6H_3 =$ ODFT) has also been added to the list of 2,6-terphenoxides (Yuan, J.; Schrock, R. R.; Müller, P.; Axtell, J. C.; Dobereiner, G. E. *Organometallics* 2012, 31, 4650). Recently it also has been possible to make bisaryloxide complexes that are especially efficient in certain stereoselective reactions, one example being $Mo(NC_6F_5)(CHCMe_2Ph)(OF_2Bitet)_2$, where $OF_2Bitet$ is a fluorinated relative of $OBr_2Bitet$ (Wang, C.; Haeflher, F.; Schrock, R. R.; Hoveyda, A. H. *Angew. Chem. Int. Ed.* 2013, 52, 1939). Despite all the development, there remains a need for olefin metathesis catalysts and methods for highly selective and efficient synthesis of Z alkenes.

SUMMARY

The present invention, among other things, encompasses the recognition that new catalysts and methods for highly efficient Z-selective metathesis reactions are needed. In some embodiments, the present invention provides new compounds as sterically demanding ligands or ligand precursors suitable for preparation of compounds that promote Z-selective metathesis reactions. In some embodiments, a new sterically demanding ligand is an aryloxide ligand. In some embodiments, the present invention provides new compounds that promote metathesis reactions. In some embodiments, a provided compound comprises a new sterically demanding ligand. In some embodiments, a provided compound comprises a new sterically demanding aryloxide ligand. In some embodiments, a provided compound is a MAP compound comprising a new sterically demanding aryloxide ligand. In some embodiments, the present invention provides new methods for metathesis reactions. In some embodiments, a provided method produces Z-alkenes with unprecedented efficiency and/or selectivity.

In some embodiments, the present invention provides a compound of formula I:

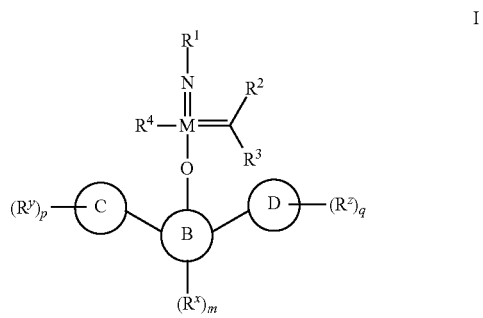

wherein:

M is molybdenum or tungsten;

$R^1$ is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

each of $R^2$ and $R^3$ is independently R', —OR', —SR', —N(R')$_2$, —OC(O)R', —SOR', —SO$_2$R', —SO$_2$N(R')$_2$, —C(O)N(R')$_2$, —NR'C(O)R', or —NR'SO$_2$R';

m is 0-3;

Ring B is an optionally substituted group selected from phenyl or a 5-6 membered monocyclic heteroaryl ring having 1-4 heteroatoms independently selected from nitrogen, oxygen, or sulfur;

each of p and q is independently 0-4;

each of Ring C and Ring D is independently an optionally substituted 5-membered monocyclic heteroaryl ring having 1-4 nitrogen atoms;

each of $R^x$, $R^y$ and $R^z$ is independently halogen, —OR', —N(R')$_2$, —NR'C(O)R', —NR'C(O)OR', —NR'C(O)N(R')$_2$, —NR'SO$_2$R', —NR'SO$_2$N(R')$_2$, —NR'OR', or an optionally substituted group selected from C$_{1-20}$ aliphatic, C$_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

$R^4$ is an optionally substituted 5-membered monocyclic heteroaryl ring having 1-2 nitrogen atoms; and each R' is independently hydrogen or an optionally substituted group selected from C$_{1-6}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or:

two R' groups on the same nitrogen atom are optionally taken together with the nitrogen atom to form an optionally substituted 3-8 membered, saturated, partially unsaturated, or aryl ring having 1-4 heteroatoms independently selected from nitrogen, oxygen, or sulfur.

In some embodiments, the present invention provides a compound of formula II:

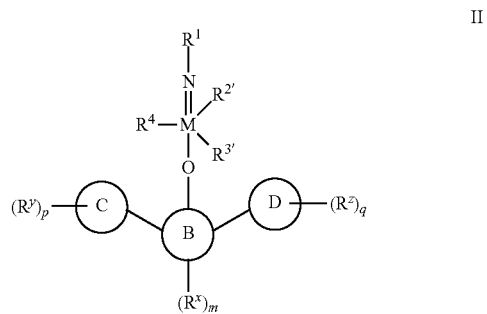

wherein:

M is molybdenum or tungsten;

$R^1$ is an optionally substituted group selected from C$_{1-20}$ aliphatic, C$_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

$R^{2'}$ and $R^{3'}$ are taken together with their intervening metal atoms to form an optionally substituted 3-8 membered saturated or partially unsaturated ring having, in addition to the intervening metal atom, 0-4 heteroatoms independently selected from nitrogen, oxygen, or sulfur;

m is 0-3;

Ring B is an optionally substituted group selected from phenyl or a 5-6 membered monocyclic heteroaryl ring having 1-4 heteroatoms independently selected from nitrogen, oxygen, or sulfur;

each of p and q is independently 0-4;

each of Ring C and Ring D is independently an optionally substituted 5-membered monocyclic heteroaryl ring having 1-4 nitrogen atoms;

each of $R^x$, $R^y$ and $R^z$ is independently halogen, —OR', —N(R')$_2$, —NR'C(O)R', —NR'C(O)OR', —NR'C(O)N(R')$_2$, —NR'SO$_2$R', —NR'SO$_2$N(R')$_2$, —NR'OR', or an optionally substituted group selected from C$_{1-20}$ aliphatic, C$_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

$R^4$ is an optionally substituted 5-membered monocyclic heteroaryl ring having 1-2 nitrogen atoms; and each R' is independently hydrogen or an optionally substituted group selected from $C_{1-6}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or:

two R' groups on the same nitrogen atom are optionally taken together with the nitrogen atom to form an optionally substituted 3-8 membered, saturated, partially unsaturated, or aryl ring having 1-4 heteroatoms independently selected from nitrogen, oxygen, or sulfur.

In some embodiments, the present invention provides new methods for highly efficient Z-selective metathesis reactions. In some embodiments, the present invention provides a method, comprising:

(a) providing a compound of formula I or II;

(b) reacting a first unsaturated bond and a second unsaturated bond to produce a product comprising an unsaturated bond.

In some embodiments, a compound in a provided method is a compound of formula I. In some embodiments, a compound in a provided method is a compound of formula II. In some embodiments, a first unsaturated bond is an unsaturated carbon-carbon bond. In some embodiments, a second unsaturated bond is an unsaturated carbon-carbon bond. In some embodiments, both the first and the second unsaturated bonds are unsaturated carbon-carbon bonds. In some embodiments, a product comprising an unsaturated bond comprises an unsaturated carbon-carbon bond. In some embodiments, a product comprising an unsaturated bond comprises an unsaturated carbon-carbon bond, wherein the unsaturated carbon-carbon bond comprises a carbon atom from the first unsaturated bond and a carbon atom from the second unsaturated bond. In some embodiments, an unsaturated carbon-carbon bond is a double bond (C=C). In some embodiments, an unsaturated carbon-carbon bond is a triple bond (C≡C).

DETAILED DESCRIPTION OF CERTAIN EMBODIMENTS

Figure 1:
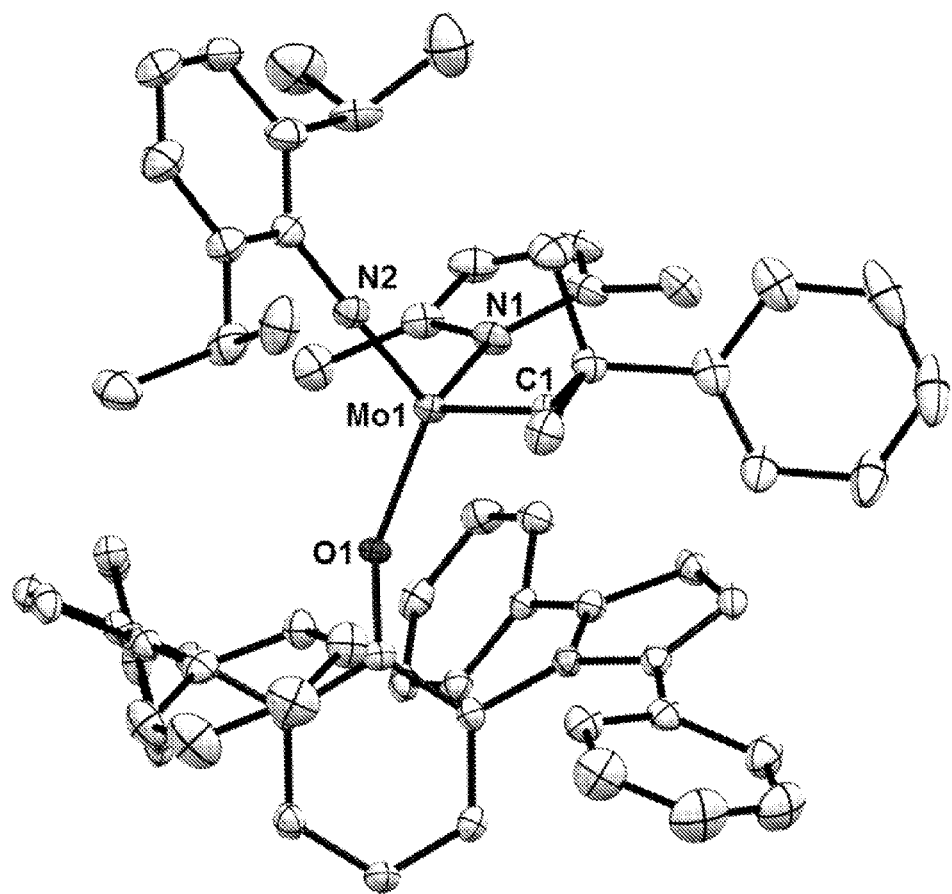
FIG. 1. Thermal ellipsoid representation of the structure of 2b at the 50% probability level. The solvent molecule and hydrogen atoms were omitted for clarity.

1. General Description of Certain Embodiments of the Invention

The present invention, among other things, provides new compounds that can be used as ligand or ligand precursor for the preparation of compounds that promotes highly efficient metathesis reactions that selectively produce Z-olefins. In some embodiments, the present invention provides compounds that promote highly efficient Z-selective metathesis reactions. In some embodiments, the present invention provides new methods for metathesis reactions. In some embodiments, a method comprising the use of a provided compound delivers up to 62% conversion and >95% Z-selectivity in the homocoupling of 1-octene in 10 minutes. Among other things, the provided compounds and methods are useful for the preparation of biologically active molecules and industrially important chemicals.

In some embodiments, the present invention provides a compound of formula I:

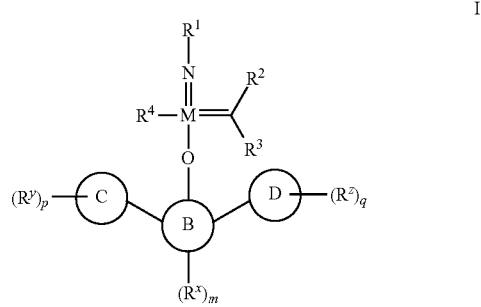

wherein:

M is molybdenum or tungsten;

$R^1$ is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

each of $R^2$ and $R^3$ is independently R', —OR', —SR', —N(R')$_2$, —OC(O)R', —SOR', —SO$_2$R', —SO$_2$N(R')$_2$, —C(O)N(R')$_2$, —NR'C(O)R', or —NR'SO$_2$R';

m is 0-3;

Ring B is an optionally substituted group selected from phenyl or a 5-6 membered monocyclic heteroaryl ring having 1-4 heteroatoms independently selected from nitrogen, oxygen, or sulfur;

each of p and q is independently 0-4;

each of Ring C and Ring D is independently an optionally substituted 5-membered monocyclic heteroaryl ring having 1-4 nitrogen atoms;

each of $R^x$, $R^y$ and $R^z$ is independently halogen, —OR', —N(R')$_2$, —NR'C(O)R', —NR'C(O)OR', —NR'C(O)N(R')$_2$, —NR'SO$_2$R', —NR'SO$_2$N(R')$_2$, —NR'OR', or an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

$R^4$ is an optionally substituted 5-membered monocyclic heteroaryl ring having 1-2 nitrogen atoms; and each R' is independently hydrogen or an optionally substituted group selected from $C_{1-6}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur; or an 8-10 membered bicyclic heteroaryl ring having 1-5 heteroatoms independently selected from nitrogen, oxygen, or sulfur; or:

two R' groups on the same nitrogen atom are optionally taken together with the nitrogen atom to form an optionally substituted 3-8 membered, saturated, partially unsaturated, or aryl ring having 1-4 heteroatoms independently selected from nitrogen, oxygen, or sulfur.

In some embodiments, the present invention provides a compound of formula II:

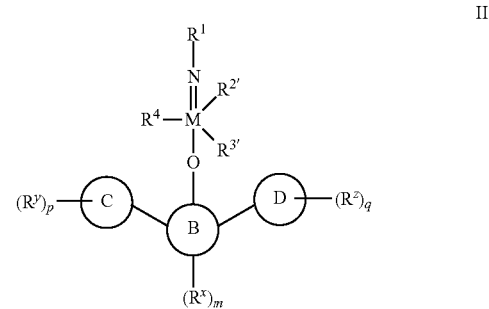

II wherein:

M is molybdenum or tungsten;

$R^1$ is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

$R^{2'}$ and $R^{3'}$ are taken together with their intervening metal atoms to form an optionally substituted 3-8 membered saturated or partially unsaturated ring having, in addition to the intervening metal atom, 0-4 heteroatoms independently selected from nitrogen, oxygen, or sulfur;

m is 0-3;

Ring B is an optionally substituted group selected from phenyl or a 5-6 membered monocyclic heteroaryl ring having 1-4 heteroatoms independently selected from nitrogen, oxygen, or sulfur;

each of p and q is independently 0-4;

each of Ring C and Ring D is independently an optionally substituted 5-membered monocyclic heteroaryl ring having 1-4 nitrogen atoms;

each of $R^x$, $R^y$ and $R^z$ is independently halogen, —OR', —N(R')$_2$, —NR'C(O)R', —NR'C(O)OR', —NR'C(O)N(R')$_2$, —NR'SO$_2$R', —NR'SO$_2$N(R')$_2$, —NR'OR', or an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

R⁴ is an optionally substituted 5-membered monocyclic heteroaryl ring having 1-2 nitrogen atoms; and each R' is independently hydrogen or an optionally substituted group selected from $C_{1-6}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or:

two R' groups on the same nitrogen atom are optionally taken together with the nitrogen atom to form an optionally substituted 3-8 membered, saturated, partially unsaturated, or aryl ring having 1-4 heteroatoms independently selected from nitrogen, oxygen, or sulfur.

In some embodiments, the present invention provides a compound of formula III:

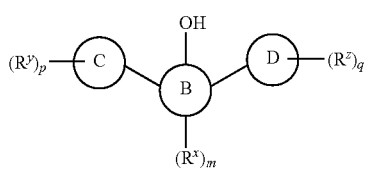

or its salt thereof,
wherein:
m is 0-3;
Ring B is an optionally substituted group selected from phenyl or a 5-6 membered monocyclic heteroaryl ring having 1-4 heteroatoms independently selected from nitrogen, oxygen, or sulfur;
each of p and q is independently 0-4;
each of Ring C and Ring D is independently an optionally substituted 5-membered monocyclic heteroaryl ring having 1-4 nitrogen atoms;
each of $R^x$, $R^y$ and $R^z$ is independently halogen, —OR', —N(R')$_2$, —NR'C(O)R', —NR'C(O)OR', —NR'C(O)N(R')$_2$, —NR'SO$_2$R', —NR'SO$_2$N(R')$_2$, —NR'OR', or an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

each R' is independently hydrogen or an optionally substituted group selected from $C_{1-6}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or:

two R' groups on the same nitrogen atom are optionally taken together with the nitrogen atom to form an optionally substituted 3-8 membered, saturated, partially unsaturated, or aryl ring having 1-4 heteroatoms independently selected from nitrogen, oxygen, or sulfur.

In some embodiments, the present invention provides new methods for highly efficient Z-selective metathesis reactions. In some embodiments, the present invention provides a method, comprising:

(a) providing a compound of formula I or II;
(b) reacting a first unsaturated bond and a second unsaturated bond to produce a product comprising an unsaturated bond.

In some embodiments, the present invention provides a method, comprising:

(a) providing a compound of formula I or II;
(b) reacting a first carbon-carbon double bond with a second carbon-carbon double to produce a product comprising a double bond, wherein said double bond in the product comprises one carbon atom from the first double bond and one carbon atom from the second double bond.

2. Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon, bicyclic hydrocarbon, or tricyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-30 aliphatic carbon atoms. In some embodiments, aliphatic groups contain 1-20 aliphatic carbon atoms. In other embodiments, aliphatic groups contain 1-10 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "cycloaliphatic," as used herein, refers to saturated or partially unsaturated cyclic aliphatic monocyclic, bicyclic, or polycyclic ring systems, as described herein, having from 3 to 14 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, the cycloalkyl has 3-6 carbons. The terms "cycloaliphatic," may also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic group is bicyclic. In some embodiments, a carbocyclic group is tricyclic. In some embodiments, a carbocyclic group is polycyclic. In some embodiments, "cycloaliphatic" (or "carbocycle" or "cycloalkyl") refers to a monocyclic $C_3$-$C_6$ hydrocarbon, or a $C_8$-$C_{10}$ bicyclic hydrocarbon that is completely saturated or that contains one or more units of unsaturation, but which is not aromatic, that has a single point of attachment to the rest of the molecule, or a $C_9$-$C_{16}$ tricyclic hydrocarbon that is completely saturated or that contains one or more units of unsaturation, but which is not aromatic, that has a single point of attachment to the rest of the molecule.

As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 1-20 carbon atoms in its backbone (e.g., $C_1$-$C_{20}$ for straight chain, $C_2$-$C_{20}$ for branched chain), and alternatively, about 1-10. In some embodiments, a cycloalkyl ring has from about 3-10 carbon atoms in their ring structure where such rings are monocyclic or bicyclic, and alternatively about 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls).

As used herein, the term "alkenyl" refers to an alkyl group, as defined herein, having one or more double bonds.

As used herein, the term "alkynyl" refers to an alkyl group, as defined herein, having one or more triple bonds.

The term "heteroalkyl" is given its ordinary meaning in the art and refers to alkyl groups as described herein in which one or more carbon atoms is replaced with a heteroatom (e.g., oxygen, nitrogen, sulfur, and the like). Examples of heteroalkyl groups include, but are not limited to, alkoxy, poly(ethylene glycol)-, alkyl-substituted amino, tetrahydrofuranyl, piperidinyl, morpholinyl, etc.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, binaphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms (i.e., monocyclic or bicyclic), in some embodiments 5, 6, 9, or 10 ring atoms. In some embodiments, such rings have 6, 10, or 14π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, a heteroaryl is a heterobiaryl group, such as bipyridyl and the like. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5-to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

The term "halogen" means F, Cl, Br, or I.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; —SiR°$_3$; —OSiR°$_3$; —(C$_{1-4}$ straight or branched)alkylene)O—N(R°)$_2$; or —(C$_{1-4}$ straight or branched)alkylene)C(O)O—N(R°)$_2$, wherein each R° may be substituted as defined below and is independently hydrogen, C$_1$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_1$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^†$ are independently halogen, —$R^•$, -(halo$R^•$), —OH, —O$R^•$, —O(halo$R^•$), —CN, —C(O)OH, —C(O)O$R^•$, —NH$_2$, —NH$R^•$, —N$R^•_2$, or —NO$_2$, wherein each $R^•$ is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "stereogenic metal atom" is given its ordinary meaning, and refers to a metal atom coordinated by at least two ligands (e.g., at least four ligands), wherein the ligands are arranged about the metal atom such that the overall structure (e.g., metal complex) lacks a plane of symmetry with respect to the metal atom. In some cases, the stereogenic metal atom may be coordinated by at least three ligands, at least four ligands, at least five ligands, at least six ligands, or more. In certain embodiments, the stereogenic metal atom may be coordinated by four ligands. Metal complexes comprising a stereogenic metal center may provide sufficient space specificity at a reaction site of the metal complex, such that a molecular substrate having a plane of symmetry may be reacted at the reaction site to form a product that is free of a plane of symmetry. That is, the stereogenic metal center of the metal complex may impart sufficient shape specificity to induce stereogenicity effectively, producing a chiral product. Such metal complexes may exhibit improved catalytic activity and stereoselectivity, relative to previous systems, and may reduce undesired side reactions (e.g., dimerization or oligomerization of the metal complex).

The term "chiral" is given its ordinary meaning in the art and refers to a molecule that is not superimposable with its mirror image, wherein the resulting nonsuperimposable mirror images are known as "enantiomers" and are labeled as either an (R) enantiomer or an (S) enantiomer. Typically, chiral molecules lack a plane of symmetry.

The term "achiral" is given its ordinary meaning in the art and refers to a molecule that is superimposable with its mirror image. Typically, achiral molecules possess a plane of symmetry.

As used herein, a ligand may be either monodentate or polydentate. In some embodiments, a ligand is monodentate. In some embodiments, a ligand is bidentate. In some embodiments, a ligand is tridentate. In some embodiments, two or more monodentate ligands are taken together to form a polydentate ligand. A ligand may have hapticity of more than one. In some cases, a ligand has a hapticity of 1 to 10. In some embodiments, a ligand has a hapticity of 1. In some embodiments, a ligand has a hapticity of 2. In some embodiments, a ligand has a hapticity of 3. In some embodiments, a ligand has a hapticity of 4. In some embodiments, a ligand has a hapticity of 5. In some embodiments, a ligand has a hapticity of 6. For a ligand having hapticity greater than one, as sometimes done in the art, a single bond may be drawn between the ligand and the metal. In some cases, a ligand is alkylidene. In some cases, a ligand is a nitrogen-containing ligand. In some cases, a ligand is an oxygen-containing ligand. In some cases, a ligand is a phosphorus-containing ligand. In some embodiments, a ligand comprises an unsaturated bond, and the unsaturated bond is coordinated to a metal. In some embodiments, a ligand comprises a carbon-carbon double bond, and the double bond is coordinated to a metal. In some embodiments, a ligand is an olefin. When an olefin double bond is coordinated to a metal, the chemical bonding between the olefin and the metal can either be depicted as a 3-membered ring wherein the ring members comprises the metal and both carbon atoms of the double bond, or as a single bond between the metal and the double bond.

As used herein, a "nitrogen-containing ligand" may be any species comprising a nitrogen atom. In some cases, the nitrogen atom may bind to the metal atom. In some cases, the nitrogen-containing ligand may bind the metal center via a different atom. In some cases, the nitrogen atom may be a ring atom of a heteroaryl or heteroalkyl group. In some cases, the nitrogen atom may be a substituted amine group. It should be understood that, in catalyst precursors described herein, the nitrogen-containing ligand may have sufficiently ionic character to coordinate a metal center, such as a Mo or W metal center. Examples of nitrogen-containing ligands include, but are not limited to, pyrrolyl, pyrazolyl, pyridinyl, pyrazinyl, pyrimidinyl, imidazolyl, triazolyl, tetrazolyl, oxazolyl, isoxazolyl, thiazolyl, isothiazolyl, indolyl, indazolyl, carbazolyl, morpholinyl, piperidinyl, oxazinyl, substituted derivatives thereof, and the like. For example, the nitrogen-containing ligand may be pyrrolide or 2,5-dimethylpyrrolide. The nitrogen-containing ligand may be selected to interact with an oxygen-containing ligand such that the oxygen-containing ligand can readily replace the nitrogen-containing ligand in a precatalyst to generate a catalyst. In cases where the catalyst composition may be generated in situ in order to carry out a chemical reaction, the first, nitrogen-containing ligand may be selected such that, upon replacement by an oxygen-containing ligand, the nitrogen-containing ligands or protonated versions thereof do not interfere with the chemical reaction. In some embodiments, the nitrogen-containing ligand may be chiral and the precatalyst may be provided as a racemic mixture or a purified stereoisomer.

In some embodiments, a nitrogen-containing ligand may also describe a ligand precursor comprising at least one hydrogen atom directly bonded to a nitrogen atom, wherein deprotonation of the at least one hydrogen atom results in a negatively charged nitrogen atom, which may coordinate to a metal atom. Exemplary such precursors include but are not limited to amines, amides, and pyrrole and its derivatives thereof. A nitrogen-containing ligand may be a heteroaryl or heteroalkyl group comprising at least one nitrogen ring atom. In some cases, the nitrogen atom may be positioned on a substituent of an alkyl, heteroalkyl, aryl, or heteroaryl group. For example, a nitrogen-containing ligand may be an amine- or amide-substituted aryl group, wherein the amine or amide group is deprotonated upon coordination to the metal center.

As used herein, the term "oxygen-containing ligand" may be used to refer to ligands comprising at least one oxygen atom. In some cases, the oxygen atom binds to the metal atom thereby forming an ether-linkage. In other cases, the oxygen-containing ligand may bind the metal center via a different atom. The term "oxygen-containing ligand" may also describe ligand precursors comprising at least one hydroxyl group (e.g., a hydroxyl-containing ligand), wherein deprotonation of the hydroxyl group results in a negatively charged oxygen atom, which may coordinate to a metal atom. The oxygen-containing ligand may be a heteroaryl or heteroalkyl group comprising at least one oxygen ring atom. In some cases, the oxygen atom may be positioned on a substituent of an alkyl, heteroalkyl, aryl, or heteroaryl group. For example, the oxygen-containing ligand may be a hydroxy-substituted aryl group, wherein the hydroxyl group is deprotonated upon coordination to the metal center.

In some embodiments, an oxygen-containing ligand may also describe a ligand precursor comprising at least one hydroxyl group (e.g., a hydroxyl-containing ligand), wherein deprotonation of the hydroxyl group results in a negatively charged oxygen atom, which may coordinate to a metal atom. An oxygen-containing ligand may be a heteroaryl or heteroalkyl group comprising at least one oxygen ring atom. In some cases, the oxygen atom may be positioned on a substituent of an alkyl, heteroalkyl, aryl, or heteroaryl group. For example, an oxygen-containing ligand may be a hydroxy-substituted aryl group, wherein the hydroxyl group is deprotonated upon coordination to the metal center.

As used herein, the term "phosphorus-containing ligand" may be used to refer to ligands comprising at least one phosphorus atom. In some cases, the phosphorus atom binds to the metal. In other cases, the phosphorus-containing ligand may bind to the metal center via a different atom (i.e., an atom other than the phosphorous). The phosphorus-containing ligand may have phosphorus atom of various oxidation states. In some cases the phosphorus-containing ligand is phosphine. In some cases the phosphorus-containing ligand is phosphite. In some cases the phosphorus-containing ligand is phosphate. The phosphorus-containing ligand may be either monodentate or polydentate. In some cases, two or more phosphorus atoms bind to the metal. In some cases, one or more phosphorus atoms together with one or more non-phosphorus atoms bind to the metal.

As defined herein, a "metal complex" is any complex used to form a provided precursor complex or any complex generated from a provided precursor complex (e.g., for use as a catalyst in a reaction such as a metathesis reaction). In some embodiments, a metal complex is a compound having the structure of formula I described herein. In some embodiments, a metal complex is a compound having the structure of formula II described herein.

The phrase "protecting group," as used herein, refers to temporary substituents which protect a potentially reactive functional group from undesired chemical transformations. Examples of such protecting groups include esters of carboxylic acids, silyl ethers of alcohols, and acetals and ketals of aldehydes and ketones, respectively. A "Si protecting group" is a protecting group comprising a Si atom, such as Si-trialkyl (e.g., trimethylsilyl, tributylsilyl, t-butyldimethylsilyl), Si-triaryl, Si-alkyl-diphenyl (e.g., t-butyldiphenylsilyl), or Si-aryl-dialkyl (e.g., Si-phenyldialkyl). Generally, a Si protecting group is attached to an oxygen atom. The field of protecting group chemistry has been reviewed (Greene, T. W.; Wuts, P. G. M. Protective Groups in Organic Synthesis, 2nd ed.; Wiley: New York, 1991). Such protecting groups (and associated protected moieties) are described in detail below.

Protected hydroxyl groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Examples of suitably protected hydroxyl groups further include, but are not limited to, esters, carbonates, sulfonates, allyl ethers, ethers, silyl ethers, alkyl ethers, arylalkyl ethers, and alkoxyalkyl ethers. Examples of suitable esters include formates, acetates, proprionates, pentanoates, crotonates, and benzoates. Specific examples of suitable esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetate), crotonate, 4-methoxy-crotonate, benzoate, p-benzylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Examples of suitable alkyl ethers include methyl, benzyl, p-methoxybenzyl, 3,4-dimethoxybenzyl, trityl, t-butyl, and allyl ether, or derivatives thereof. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyran-2-yl ether. Examples of suitable arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

Protected amines are well known in the art and include those described in detail in Greene (1999). Suitable mono-protected amines further include, but are not limited to, aralkylamines, carbamates, allyl amines, amides, and the like. Examples of suitable mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxocarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Suitable di-protected amines include amines that are substituted with two substituents independently selected from those described above as mono-protected amines, and further include cyclic imides, such as phthalimide, maleimide, succinimide, and the like. Suitable di-protected amines also include pyrroles and the like, 2,2,5,5-tetramethyl-[1,2,5] azadisilolidine and the like, and azide.

Protected aldehydes are well known in the art and include those described in detail in Greene (1999). Suitable protected aldehydes further include, but are not limited to, acyclic acetals, cyclic acetals, hydrazones, imines, and the like. Examples of such groups include dimethyl acetal, diethyl acetal, diisopropyl acetal, dibenzyl acetal, bis(2-nitrobenzyl) acetal, 1,3-dioxanes, 1,3-dioxolanes, semicarbazones, and derivatives thereof.

Protected carboxylic acids are well known in the art and include those described in detail in Greene (1999). Suitable protected carboxylic acids further include, but are not limited to, optionally substituted $C_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, benzyl, and phenyl ester, wherein each group is optionally substituted. Additional suitable protected carboxylic acids include oxazolines and ortho esters.

Protected thiols are well known in the art and include those described in detail in Greene (1999). Suitable protected thiols further include, but are not limited to, disulfides, thioethers, silyl thioethers, thioesters, thiocarbonates, and thiocarbamates, and the like. Examples of such groups include, but are not limited to, alkyl thioethers, benzyl and substituted benzyl thioethers, triphenylmethyl thioethers, and trichloroethoxycarbonyl thioester, to name but a few.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{11}$C- or $^{13}$C- or $^{14}$C-enriched carbon are within the scope of this invention. Such compounds are useful, for example, as analytical tools or probes in biological assays.

As used herein and in the claims, the singular forms "a", "an", and "the" include the plural reference unless the context clearly indicates otherwise. Thus, for example, a reference to "a compound" includes a plurality of such compounds.

3. Description of Certain Embodiments of the Invention

The present invention, among other things, encompasses the recognition that new catalysts and methods for highly efficient Z-selective metathesis reactions are needed. In some embodiments, the present invention provides new compounds as sterically demanding ligands or ligand precursors suitable for preparation of compounds that promote Z-selective metathesis reactions. In some embodiments, a new sterically demanding ligand or ligand precursor is an aryloxide ligand. In some embodiments, the present invention provides new compounds that promote metathesis reactions. In some embodiments, a provided compound comprises a new sterically demanding ligand. In some embodiments, a provided compound comprises a new sterically demanding aryloxide ligand. In some embodiments, a provided compound is a MAP compound comprising a new sterically demanding aryloxide ligand. In some embodiments, the present invention provides new methods for metathesis reactions. In some embodiments, a provided method produces Z-alkenes with unprecedented efficiency and/or selectivity.

As used herein, the term "metathesis reaction" is given its ordinary meaning in the art and refers to a chemical reaction in which two reacting species exchange partners. In some embodiments, a metathesis reaction is performed in the presence of a transition-metal catalyst. In some cases, a byproduct of a metathesis reaction may be ethylene. A metathesis reaction may involve reaction between species comprising, for example, olefins and/or alkynes. Examples of different kinds of metathesis reactions include cross metathesis, ring-closing metathesis, ring-opening metathesis, acyclic diene metathesis, alkyne metathesis, enyne metathesis, olefin metathesis and the like. A metathesis reaction may occur between two substrates which are not joined by a bond (e.g., intermolecular metathesis reaction) or between two portions of a single substrate (e.g., intramolecular metathesis reaction). In some embodiments, two substrates of a metathesis reaction are identical. In some embodiments, a provided compound of the present invention is useful in the formation of a metathesis product with high efficiency and high Z-selectivity.

As defined above, M is molybdenum or tungsten. In some embodiments, M is molybdenum. In other embodiments, M is tungsten.

As defined generally above, $R^1$ is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur.

In some embodiments, $R^1$ is optionally substituted $C_{1-20}$ aliphatic. In some embodiments, $R^1$ is optionally substituted $C_{1-20}$ cycloaliphatic. In some embodiments, $R^1$ is optionally substituted $C_{1-12}$ aliphatic. In some embodiments, $R^1$ is optionally substituted $C_{1-12}$ cycloaliphatic. In some embodiments, $R^1$ is optionally substituted $C_{1-12}$ cycloalkyl. In some embodiments, $R^1$ is optionally substituted adamantyl. In some embodiments, $R^1$ is adamantyl. In some embodiments, $R^1$ is optionally substituted $C_{1-6}$ aliphatic. In some embodiments, $R^1$ is optionally substituted $C_{1-6}$ alkyl. In some embodiments, $R^1$ is optionally substituted hexyl, pentyl, butyl, propyl, ethyl or methyl. In some embodiments, $R^1$ is optionally substituted hexyl. In some embodiments, $R^1$ is optionally substituted pentyl. In some embodiments, $R^1$ is optionally substituted butyl. In some embodiments, $R^1$ is optionally substituted propyl. In some embodiments, $R^1$ is optionally substituted ethyl. In some embodiments, $R^1$ is optionally substituted methyl. In some embodiments, $R^1$ is hexyl. In some embodiments, $R^1$ is pentyl. In some embodiments, $R^1$ is butyl. In some embodiments, $R^1$ is propyl. In some embodiments, $R^1$ is ethyl. In some embodiments, $R^1$ is methyl. In some embodiments, $R^1$ is isopropyl.

In certain embodiments, $R^1$ is optionally substituted phenyl. In some embodiments, $R^1$ is substituted phenyl. In some embodiments, $R^1$ is mono-, di-, tri-, tetra- or penta-substituted phenyl. In some embodiments, $R^1$ is mono-substituted phenyl. In certain embodiments, $R^1$ is 2,6-disubstituted phenyl. In some embodiments, $R^1$ is tri-substituted phenyl. In some embodiments, $R^1$ is tetra-substituted phenyl. In some embodiments, $R^1$ is penta-substituted phenyl. In some embodiments, a substituent is a halogen. In some embodiments, a substituent is —F, and $R^1$ is phenyl substituted with one or more —F. In some embodiments, $R^1$ is pentafluorophenyl. In some embodiments, a substituent is optionally substituted $C_{1-4}$ aliphatic. In some embodiments, $R^1$ is phenyl disubstituted with halogen or $C_{1-4}$ aliphatic. Such $R^1$ groups include but are not limited to 2,6-dichlorophenyl, 2,6-dibromophenyl, 2,6-dimethylphenyl, 2,6-di-tert-butylphenyl, and 2,6-diisopropylphenyl.

In some embodiments, $R^1$ is selected from:

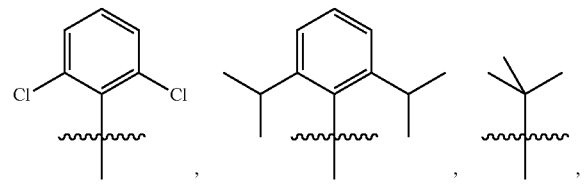

-continued

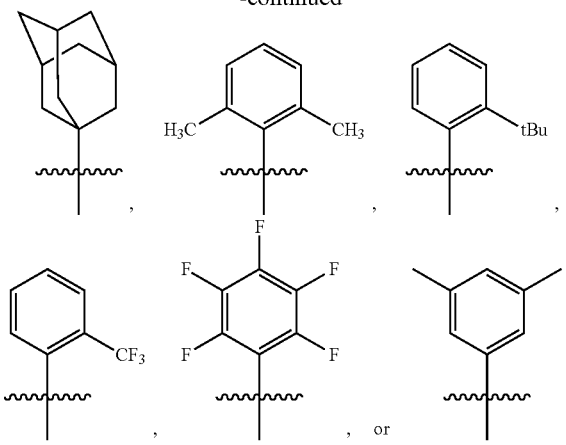

As defined generally above, each of $R^2$ and $R^3$ is independently R', —OR', —SR', —N(R')$_2$, —OC(O)R', —SOR', —SO$_2$R', —SO$_2$N(R)$_2$, —C(O)N(R')$_2$, —NR'C(O)R', or —NR'SO$_2$R', wherein each R' is independently as defined above and described herein.

In some embodiments, both of $R^2$ and $R^3$ are hydrogen. In some embodiments, one of $R^2$ and $R^3$ is hydrogen and the other is an optionally substituted group selected from $C_{1-6}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur, —OR', —SR', —N(R')$_2$, —OC(O)R', —SOR', —SO$_2$R', —SO$_2$N(R')$_2$, —C(O)N(R')$_2$, —NR'C(O)R', or —NR'SO$_2$R'. In some embodiments, one of $R^2$ and $R^3$ is hydrogen and the other is an optionally substituted group selected from $C_{1-6}$ aliphatic, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur.

In certain embodiments, $R^2$ or $R^3$ is optionally substituted $C_{1-6}$ aliphatic. In certain embodiments, $R^2$ or $R^3$ is optionally substituted $C_{1-6}$ alkyl. In certain embodiments, $R^2$ or $R^3$ is $C_{1-6}$ alkyl substituted with phenyl and one or two additional substituents. In certain embodiments, $R^2$ or $R^3$ is a lower alkyl group optionally substituted with one or two methyl groups and phenyl. In certain embodiments, $R^2$ or $R^3$ is —C(Me)$_2$Ph. In certain embodiments, $R^2$ or $R^3$ is —C(Me)$_3$.

In certain embodiments, each of $R^2$ and $R^3$ is independently R', wherein R' is as defined above and described herein. In some embodiments, each of $R^2$ and $R^3$ is independently R', wherein at least one of $R^2$ and $R^3$ is not hydrogen.

In certain embodiments, $R^2$ is hydrogen and $R^3$ is R', —OR', —SR', —N(R')$_2$, —OC(O)R', —SOR', —SO$_2$R', —SO$_2$N(R')$_2$, —C(O)N(R')$_2$, —NR'C(O)R', or —NR'SO$_2$R', wherein each R' is independently as defined above and described herein. In certain embodiments, $R^2$ is hydrogen and $R^3$ is R', wherein R' is as defined above and described herein. In certain embodiments, $R^2$ is hydrogen and $R^3$ is optionally substituted $C_{1-20}$ aliphatic. In some embodiments, $R^2$ is hydrogen and $R^3$ is optionally substituted $C_{1-20}$ alkyl. In certain embodiments, $R^2$ is hydrogen and $R^3$ is $C_{1-6}$ alkyl substituted with phenyl and one or two additional substituents. In certain embodiments, $R^2$ is hydrogen and $R^3$ is a lower alkyl group optionally substituted with one or two methyl groups and phenyl. In certain embodiments, $R^2$ is hydrogen and $R^3$ is —C(Me)$_2$Ph. In certain embodiments, $R^2$ is hydrogen and $R^3$ is —C(Me)$_3$.

As generally defined above, m is 0-3. In some embodiments, m is 0. In some embodiments, m is 1-3. In some embodiments, m is 1. In some embodiments, m is 2. In some embodiments, m is 3. In some embodiments, m is 0-2.

As generally defined above, Ring B is an optionally substituted group selected from phenyl or a 5-6 membered monocyclic heteroaryl ring having 1-4 heteroatoms independently selected from nitrogen, oxygen, or sulfur. In some embodiments, Ring B is of the following structure:

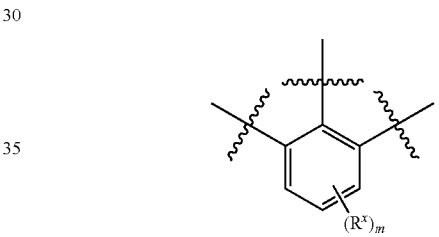

wherein $R^x$ and m are as defined above and described herein. In some embodiments, Ring B is optionally substituted phenyl. In some embodiments, m=0. In some embodiments, Ring B is

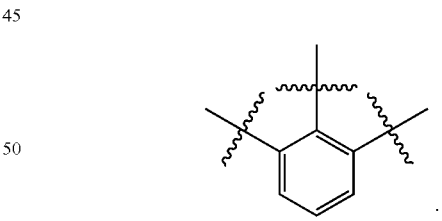

In some embodiments, Ring B is an optionally substituted 5-6 membered monocyclic heteroaryl ring having 1-4 heteroatoms independently selected from nitrogen, oxygen, or sulfur. In some embodiments, Ring B is an optionally substituted 5-membered monocyclic heteroaryl ring having 1-4 heteroatoms independently selected from nitrogen, oxygen, or sulfur, and m is 0-2. In some embodiments, Ring B is an optionally substituted 6-membered monocyclic heteroaryl ring having 1-4 heteroatoms independently selected from nitrogen, oxygen, or sulfur, and m is 0-3.

In some embodiments, Ring B is a 5-6 membered monocyclic heteroaryl ring having 1-4 heteroatoms independently selected from nitrogen, oxygen, or sulfur. In some embodiments, Ring B is a 5-6 membered monocyclic heteroaryl ring having 1-2 heteroatoms independently selected from nitrogen, oxygen, or sulfur.

In some embodiments, Ring B is a 5-membered monocyclic heteroaryl ring having 1-4 heteroatoms independently selected from nitrogen, oxygen, or sulfur. In some embodiments, Ring B is a 5-membered monocyclic heteroaryl ring having 1-2 heteroatoms independently selected from nitrogen, oxygen, or sulfur.

In some embodiments, Ring B is a 6-membered monocyclic heteroaryl ring having 1-4 heteroatoms independently selected from nitrogen, oxygen, or sulfur. In some embodiments, Ring B is a 6-membered monocyclic heteroaryl ring having 1-2 heteroatoms independently selected from nitrogen, oxygen, or sulfur.

Exemplary optionally substituted Ring B heteroaryl groups include thienylene, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, and the like.

As generally defined above, each of p and q is independently 0-4. In some embodiments, p is 0. In some embodiments, p is 1-4. In some embodiments, p is 1. In some embodiments, p is 2. In some embodiments, p is 3. In some embodiments, p is 4.

In some embodiments, q is 0. In some embodiments, q is 1-4. In some embodiments, q is 1. In some embodiments, q is 2. In some embodiments, q is 3. In some embodiments, q is 4.

In some embodiments, each of p and q is independently 1-4. In some embodiments, p is 2 and q is 2. In some embodiments, p is 2 and q is 2, and each of Ring C and Ring D independently has two substituents. In some embodiments, each of Ring C and Ring D has two substituents, and each substituent is at the o-position relative to the ring atom bonded to Ring B.

As generally defined above, each of Ring C and Ring D is independently an optionally substituted 5-membered monocyclic heteroaryl ring having 1-4 nitrogen atoms. In some embodiments, each of Ring C and Ring D is independently an optionally substituted group selected from pyrrolyl, imidazolyl, and pyrazolyl.

In some embodiments, at least one of Ring C and Ring D is a 2,5-disubstituted 5-membered monocyclic heteroaryl ring having 1-4 nitrogen atoms. In some embodiments, at least one of Ring C and Ring D is a 2,5-disubstituted 5-membered monocyclic heteroaryl ring having 1-4 nitrogen atoms. In some embodiments, each of Ring C and Ring D is a disubstituted 5-membered monocyclic heteroaryl ring having 1-4 nitrogen atoms. In some embodiments, each of Ring C and Ring D is a 2,5-disubstituted 5-membered monocyclic heteroaryl ring having 1-4 nitrogen atoms.

In some embodiments, at least one of Ring C and Ring D is optionally substituted pyrrolyl. In some embodiments, at least one of Ring C and Ring D is independently optionally substituted pyrrolyl having the structure of

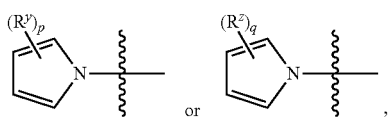

wherein each of p, q, $R^y$ and $R^z$ is independently as defined above and described herein. In some embodiments, at least one of Ring C and Ring D is disubstituted pyrrolyl having the structure of

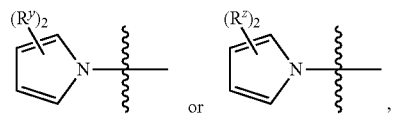

wherein each of $R^y$ and $R^z$ is independently as defined above and described herein. In some embodiments, at least one of Ring C and Ring D is 2,5-disubstituted pyrrolyl. In some embodiments, at least one of Ring C and Ring D is 2,5-disubstituted pyrrolyl having the structure of

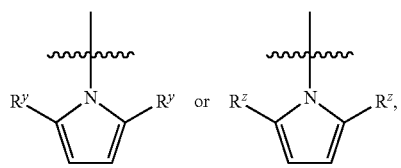

wherein each of $R^y$ and $R^z$ is independently as defined above and described herein. In some embodiments, at least one of Ring C and Ring D is

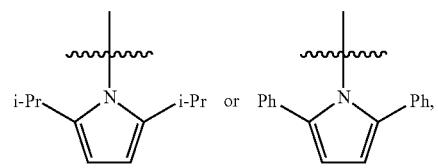 [SMILES: *n1c(C(C)C)ccc1C(C)C ; *n1c(-c2ccccc2)ccc1-c1ccccc1]

wherein each of the phenyl and isopropyl group is independently optionally substituted. In some embodiments, at least one of Ring C and Ring D is

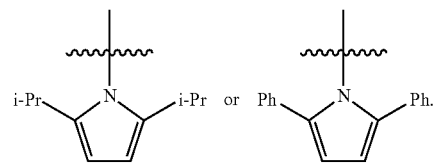 [SMILES: *n1c(C(C)C)ccc1C(C)C ; *n1c(-c2ccccc2)ccc1-c1ccccc1]

In some embodiments, at least one of Ring C and Ring D is

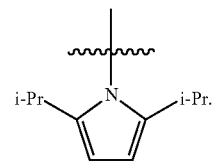 [SMILES: *n1c(C(C)C)ccc1C(C)C]

In some embodiments, at least one of Ring C and Ring D is

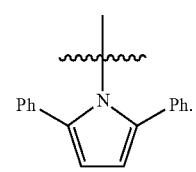

In some embodiments, each of Ring C and Ring D is independently optionally substituted pyrrolyl. In some embodiments, each of Ring C and Ring D is independently disubstituted pyrrolyl. In some embodiments, Ring C has the structure of

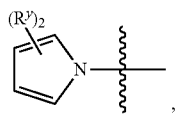

and Ring D has the structure of

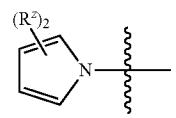

wherein each of $R^y$ and $R^z$ is independently as defined above and described herein. In some embodiments, each of Ring C and Ring D is independently 2,5-disubstituted pyrrolyl. In some embodiments, Ring C has the structure of

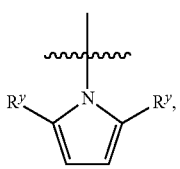

and Ring D has the structure of

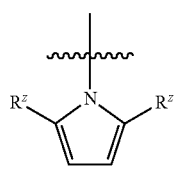

wherein each of $R^y$ and $R^z$ is independently as defined above and described herein. In some embodiments, each of Ring C and Ring D is independently

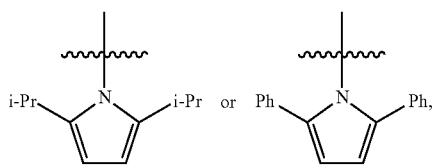 [SMILES: *n1c(C(C)C)ccc1C(C)C ; *n1c(-c2ccccc2)ccc1-c1ccccc1]

wherein each of the phenyl, isopropyl and pyrrolyl groups is independently optionally substituted. In some embodiments, each of Ring C and Ring D is independently

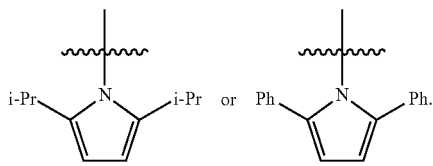 [SMILES: *n1c(C(C)C)ccc1C(C)C ; *n1c(-c2ccccc2)ccc1-c1ccccc1]

In some embodiments, each of Ring C and Ring D is

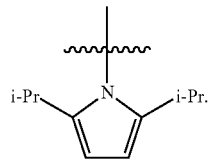

In some embodiments, each of Ring C and Ring D is

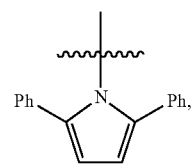

wherein each phenyl group is optionally substituted. In some embodiments, each of Ring C and Ring D is

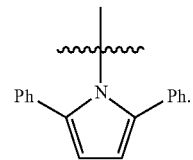 [SMILES: *n1c(-c2ccccc2)ccc1-c1ccccc1]

In some embodiments, Ring C is an optionally substituted 5-membered monocyclic heteroaryl ring having 1-4 nitrogen atoms. In some embodiments, Ring C is an optionally substituted 5-membered monocyclic heteroaryl ring having one nitrogen atom. In some embodiments, Ring C is optionally substituted pyrrolyl. In some embodiments, Ring C is optionally substituted 1-pyrrolyl. In some embodiments, Ring C is an optionally substituted 5-membered monocyclic heteroaryl ring having two nitrogen atoms. In some embodiments, Ring C is optionally substituted imidazolyl. In some embodiments, Ring C is optionally substituted pyrazolyl. In some embodiments, Ring C is an optionally substituted 5-membered monocyclic heteroaryl ring having three nitrogen atoms. In some embodiments, Ring C is optionally substituted triazolyl. In some embodiments, Ring C is an optionally substituted 5-membered monocyclic heteroaryl ring having four nitrogen atoms. In some embodiments, Ring C is optionally substituted tetrazolyl.

In some embodiments, Ring C is optionally substituted pyrrolyl. In some embodiments, Ring C is optionally substituted 1-pyrrolyl. In some embodiments, Ring C is optionally substituted pyrrolyl having the structure of

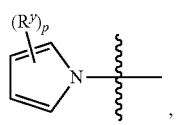

wherein each of p and $R^y$ is independently as defined above and described herein. In some embodiments, Ring C is

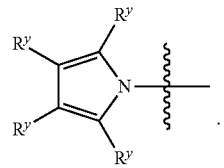

In some embodiments, Ring C is tetrasubstituted. In some embodiments, Ring C is disubstituted pyrrolyl. In some embodiments, Ring C is disubstituted pyrrolyl having the structure of

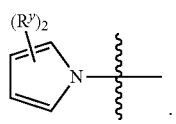

In some embodiments, Ring C is 2,5-disubstituted pyrrolyl. In some embodiments, Ring C is 2,5-disubstituted pyrrolyl having the structure of

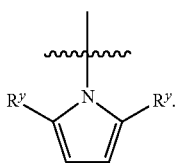

In some embodiments, Ring C is 2,5-disubstituted pyrrolyl having the structure of

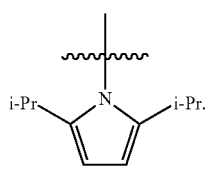

In some embodiments, Ring C is 2,5-disubstituted pyrrolyl having the structure of

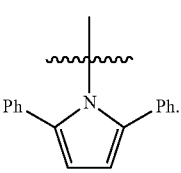

In some embodiments, Ring C is optionally substituted imidazolyl. In some embodiments, Ring C is optionally substituted imidazolyl having the structure of

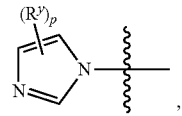

wherein each of p and $R^y$ is independently as defined above and described herein. In some embodiments, Ring C is disubstituted imidazolyl. In some embodiments, Ring C is disubstituted imidazolyl having the structure of

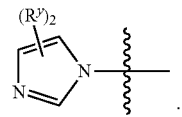

In some embodiments, Ring C is 2,5-disubstituted imidazolyl. In some embodiments, Ring C is 2,5-disubstituted imidazolyl having the structure of

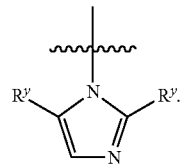

In some embodiments, Ring C is 2,5-disubstituted pyrrolyl having the structure of

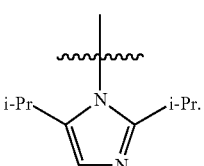 [SMILES: *n1c(C(C)C)ccc1C(C)C]

In some embodiments, Ring C is 2,5-disubstituted pyrrolyl having the structure of

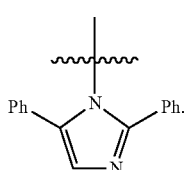

In some embodiments, Ring C is optionally substituted pyrazolyl. In some embodiments, Ring C is optionally substituted pyrazolyl having the structure of

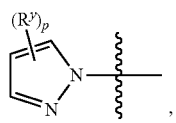

wherein each of p and $R^y$ is independently as defined above and described herein. In some embodiments, Ring C is disubstituted pyrazolyl. In some embodiments, Ring C is disubstituted pyrazolyl having the structure of

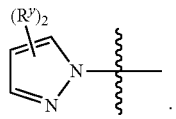

In some embodiments, Ring D is an optionally substituted 5-membered monocyclic heteroaryl ring having 1-4 nitrogen atoms. In some embodiments, Ring D is an optionally substituted 5-membered monocyclic heteroaryl ring having one nitrogen atom. In some embodiments, Ring D is optionally substituted pyrrolyl. In some embodiments, Ring D is optionally substituted 1-pyrrolyl. In some embodiments, Ring D is an optionally substituted 5-membered monocyclic heteroaryl ring having two nitrogen atoms. In some embodiments, Ring D is optionally substituted imidazolyl. In some embodiments, Ring D is optionally substituted pyrazolyl. In some embodiments, Ring D is an optionally substituted 5-membered monocyclic heteroaryl ring having three nitrogen atoms. In some embodiments, Ring D is optionally substituted triazolyl. In some embodiments, Ring D is an optionally substituted 5-membered monocyclic heteroaryl ring having four nitrogen atoms. In some embodiments, Ring D is optionally substituted tetrazolyl.

In some embodiments, Ring D is optionally substituted pyrrolyl. In some embodiments, Ring D is optionally substituted 1-pyrrolyl. In some embodiments, Ring D is optionally substituted pyrrolyl having the structure of

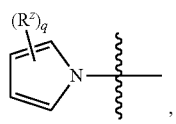

wherein each of p and $R^y$ is independently as defined above and described herein. In some embodiments, Ring D is

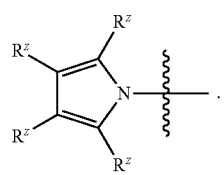

In some embodiments, Ring D is tetrasubstituted. In some embodiments, Ring D is disubstituted pyrrolyl. In some embodiments, Ring D is disubstituted pyrrolyl. In some embodiments, Ring D is disubstituted pyrrolyl having the structure of In some embodiments, Ring D is 2,5-disubstituted pyrrolyl. In some embodiments, Ring D is 2,5-disubstituted pyrrolyl having the structure of

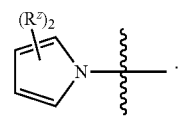

In some embodiments, Ring D is 2,5-disubstituted pyrrolyl having the structure of

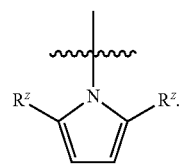

In some embodiments, Ring D is 2,5-disubstituted pyrrolyl having the structure of

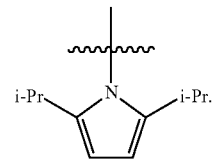

In some embodiments, Ring D is optionally substituted imidazolyl. In some embodiments, Ring D is optionally substituted imidazolyl having the structure of

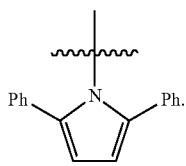

wherein each of p and $R^y$ is independently as defined above and described herein. In some embodiments, Ring D is disubstituted imidazolyl. In some embodiments, Ring D is disubstituted imidazolyl having the structure of

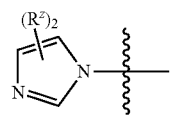

In some embodiments, Ring D is 2,5-disubstituted imidazolyl. In some embodiments, Ring D is 2,5-disubstituted imidazolyl having the structure of

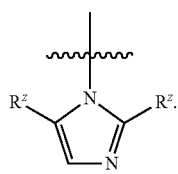

In some embodiments, Ring D is 2,5-disubstituted pyrrolyl having the structure of

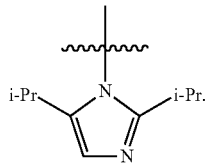

In some embodiments, Ring D is 2,5-disubstituted pyrrolyl having the structure of

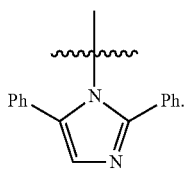

In some embodiments, Ring D is optionally substituted pyrazolyl. In some embodiments, Ring D is optionally substituted pyrazolyl having the structure of

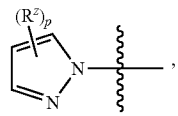

wherein each of p and $R^y$ is independently as defined above and described herein. In some embodiments, Ring D is disubstituted pyrazolyl. In some embodiments, Ring D is disubstituted pyrazolyl having the structure of

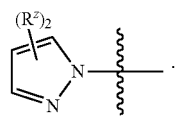

In some embodiments, Ring C and Ring D are the same. In some embodiments, Ring C and Ring D are different. In some embodiments, Ring C and Ring D are different, and at least one of Ring C and Ring D is optionally substituted pyrrolyl.

As generally defined above, each of $R^x$, $R^y$ and $R^z$ is independently halogen, —OR', —N(R')$_2$, —NR'C(O)R', —NR'C(O)OR', —NR'C(O)N(R')$_2$, —NR'SO$_2$R', —NR'SO$_2$N(R')$_2$, —NR'OR', or an optionally substituted group selected from C$_{1-20}$ aliphatic, C$_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur.

In certain embodiments, $R^x$ is independently halogen. In some embodiments, $R^x$ is —F. In some embodiments, $R^x$ is —Cl. In some embodiments, $R^x$ is —Br. In some embodiments, $R^x$ is —I.

In some embodiments, $R^x$ is —OR', —N(R')$_2$, —NR'C(O)R', —NR'C(O)OR', —NR'C(O)N(R')$_2$, —NR'SO$_2$R', —NR'SO$_2$N(R')$_2$, or —NR'OR', wherein each of R' is independently as defined above and described herein.

In some embodiments, $R^x$ is an optionally substituted group selected from C$_{1-20}$ aliphatic, C$_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur.

In some embodiments, $R^x$ is optionally substituted C$_{1-20}$ aliphatic. In some embodiments, $R^x$ is optionally substituted C$_{1-20}$ alkyl. In some embodiments, $R^x$ is optionally substituted C$_{1-12}$ aliphatic. In some embodiments, $R^x$ is optionally substituted C$_{1-12}$ alkyl. In some embodiments, $R^x$ is optionally substituted C$_{1-6}$ aliphatic. In some embodiments, $R^x$ is optionally substituted C$_{1-6}$ alkyl. In some embodiments, $R^x$ is optionally substituted hexyl, pentyl, butyl, propyl, ethyl or methyl. In some embodiments, $R^x$ is optionally substituted hexyl. In some embodiments, $R^x$ is optionally substituted pentyl. In some embodiments, $R^x$ is optionally substituted butyl. In some embodiments, $R^x$ is optionally substituted propyl. In some embodiments, $R^x$ is optionally substituted ethyl. In some embodiments, $R^x$ is optionally substituted methyl. In some embodiments, $R^x$ is hexyl. In some embodiments, $R^x$ is pentyl. In some embodiments, $R^x$ is butyl. In some embodiments, $R^x$ is propyl. In some embodiments, $R^x$ is ethyl. In some embodiments, $R^x$ is methyl. In some embodiments, $R^x$ is isopropyl.

In some embodiments, $R^x$ optionally substituted C$_{1-20}$ heteroaliphatic having 1-3 heteroatoms independently selected from nitrogen, oxygen, or sulfur. In some embodiments, $R^x$ is —OR', wherein R' is as defined above and described herein. In some embodiments, $R^x$ is —SR', wherein R' is as defined above and described herein. In some embodiments, Rx is —N(R')$_2$, wherein each R' is independently as defined above and described herein.

In some embodiments, $R^x$ is R', wherein R' is as defined above and described herein.

In some embodiments, $R^x$ is optionally substituted phenyl. In some embodiments, $R^x$ is optionally substituted phenyl wherein one or more substituents are halogen. In some embodiments, $R^x$ is optionally substituted phenyl wherein one or more substituents are —F. In some embodiments, $R^x$ is optionally substituted phenyl wherein one or more substituents are —Cl. In some embodiments, $R^x$ is optionally substituted phenyl wherein one or more substituents are —Br. In some embodiments, $R^x$ is optionally substituted phenyl wherein one or more substituents are —I. In some embodiments, $R^x$ is phenyl.

In some embodiments, $R^x$ is a 3-7 membered saturated or partially unsaturated carbocyclic ring. In some embodiments, $R^x$ is a 3-membered saturated or partially unsaturated carbocyclic ring. In some embodiments, $R^x$ is a 4-membered saturated or partially unsaturated carbocyclic ring. In some embodiments, $R^x$ is a 5-membered saturated or partially unsaturated carbocyclic ring. In some embodiments, $R^x$ is a 6-membered saturated or partially unsaturated carbocyclic ring. In some embodiments, $R^x$ is a 7-membered saturated or partially unsaturated carbocyclic ring.

In some embodiments, $R^x$ is an 8-10 membered bicyclic saturated, partially unsaturated or aryl ring. In some embodiments, $R^x$ is an 8-10 membered bicyclic saturated ring. In some embodiments, $R^x$ is an 8-10 membered bicyclic partially unsaturated ring. In some embodiments, $R^x$ is an 8-10 membered bicyclic aryl ring.

In some embodiments, $R^x$ is a 5-6 membered monocyclic heteroaryl ring having 1-4 heteroatoms independently selected from nitrogen, oxygen, or sulfur. In some embodiments, $R^x$ is a 5-membered monocyclic heteroaryl ring having 1-4 heteroatoms independently selected from nitrogen, oxygen, or sulfur. In some embodiments, $R^x$ is a 6-membered monocyclic heteroaryl ring having 1-4 heteroatoms independently selected from nitrogen, oxygen, or sulfur.

In some embodiments, $R^x$ is a 3-7 membered saturated or partially unsaturated heterocyclic ring having 1-3 heteroatoms independently selected from nitrogen, oxygen, or sulfur. In some embodiments, $R^x$ is a 3-membered saturated or partially unsaturated heterocyclic ring having 1-2 heteroatoms independently selected from nitrogen, oxygen, or sulfur. In some embodiments, $R^x$ is a 4-membered saturated or partially unsaturated heterocyclic ring having 1-2 heteroatoms independently selected from nitrogen, oxygen, or sulfur. In some embodiments, $R^x$ is a 5-membered saturated or partially unsaturated heterocyclic ring having 1-3 heteroatoms independently selected from nitrogen, oxygen, or sulfur. In some embodiments, $R^x$ is a 6-membered saturated or partially unsaturated heterocyclic ring having 1-3 heteroatoms independently selected from nitrogen, oxygen, or sulfur. In some embodiments, $R^x$ is a 7-membered saturated or partially unsaturated heterocyclic ring having 1-3 heteroatoms independently selected from nitrogen, oxygen, or sulfur.

In some embodiments, $R^x$ is a 7-10 membered bicyclic saturated or partially unsaturated heterocyclic ring having 1-5 heteroatoms independently selected from nitrogen, oxygen, or sulfur.

In some embodiments, $R^x$ is an 8-10 membered bicyclic heteroaryl ring having 1-5 heteroatoms independently selected from nitrogen, oxygen, or sulfur.

In certain embodiments, $R^y$ is independently halogen. In some embodiments, $R^y$ is —F. In some embodiments, $R^y$ is —Cl. In some embodiments, $R^y$ is —Br. In some embodiments, $R^y$ is —I.

In some embodiments, $R^y$ is —OR', —N(R')$_2$, —NR'C(O)R', —NR'C(O)OR', —NR'C(O)N(R')$_2$, —NR'SO$_2$R', —NR'SO$_2$N(R')$_2$, or —NR'OR', wherein each of R' is independently as defined above and described herein.

In some embodiments, $R^y$ is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur.

In some embodiments, $R^y$ is optionally substituted $C_{1-20}$ aliphatic. In some embodiments, $R^y$ is optionally substituted $C_{1-20}$ alkyl. In some embodiments, $R^y$ is optionally substituted $C_{1-12}$ aliphatic. In some embodiments, $R^y$ is optionally substituted $C_{1-12}$ alkyl. In some embodiments, $R^y$ is optionally substituted $C_{1-6}$ aliphatic. In some embodiments, $R^y$ is optionally substituted $C_{1-6}$ alkyl. In some embodiments, $R^y$ is optionally substituted hexyl, pentyl, butyl, propyl, ethyl or methyl. In some embodiments, $R^y$ is optionally substituted hexyl. In some embodiments, $R^y$ is optionally substituted pentyl. In some embodiments, $R^y$ is optionally substituted butyl. In some embodiments, $R^y$ is optionally substituted propyl. In some embodiments, $R^y$ is optionally substituted ethyl. In some embodiments, $R^y$ is optionally substituted methyl. In some embodiments, $R^y$ is hexyl. In some embodiments, $R^y$ is pentyl. In some embodiments, $R^y$ is butyl. In some embodiments, $R^y$ is propyl. In some embodiments, $R^y$ is ethyl. In some embodiments, $R^y$ is methyl. In some embodiments, $R^y$ is isopropyl.

In some embodiments, $R^y$ optionally substituted $C_{1-20}$ heteroaliphatic having 1-3 heteroatoms independently selected from nitrogen, oxygen, or sulfur. In some embodiments, $R^y$ is —OR', wherein R' is as defined above and described herein. In some embodiments, $R^y$ is —SR', wherein R' is as defined above and described herein. In some embodiments, $R^y$ is —N(R')$_2$, wherein each R' is independently as defined above and described herein.

In some embodiments, $R^y$ is R', wherein R' is as defined above and described herein.

In some embodiments, $R^y$ is optionally substituted phenyl. In some embodiments, $R^y$ is optionally substituted phenyl wherein one or more substituents are halogen. In some embodiments, $R^y$ is optionally substituted phenyl wherein one or more substituents are —F. In some embodiments, $R^y$ is optionally substituted phenyl wherein one or more substituents are —Cl. In some embodiments, $R^y$ is optionally substituted phenyl wherein one or more substituents are —Br. In some embodiments, $R^y$ is optionally substituted phenyl wherein one or more substituents are —I. In some embodiments, $R^y$ is phenyl.

In some embodiments, $R^y$ is a 3-7 membered saturated or partially unsaturated carbocyclic ring. In some embodiments, $R^y$ is a 3-membered saturated or partially unsaturated carbocyclic ring. In some embodiments, $R^y$ is a 4-membered saturated or partially unsaturated carbocyclic ring. In some embodiments, $R^y$ is a 5-membered saturated or partially unsaturated carbocyclic ring. In some embodiments, $R^y$ is a 6-membered saturated or partially unsaturated carbocyclic ring. In some embodiments, $R^y$ is a 7-membered saturated or partially unsaturated carbocyclic ring.

In some embodiments, $R^y$ is an 8-10 membered bicyclic saturated, partially unsaturated or aryl ring. In some embodiments, $R^y$ is an 8-10 membered bicyclic saturated ring. In some embodiments, $R^y$ is an 8-10 membered bicyclic partially unsaturated ring. In some embodiments, $R^y$ is an 8-10 membered bicyclic aryl ring.

In some embodiments, $R^y$ is a 5-6 membered monocyclic heteroaryl ring having 1-4 heteroatoms independently selected from nitrogen, oxygen, or sulfur. In some embodiments, $R^y$ is a 5-membered monocyclic heteroaryl ring having 1-4 heteroatoms independently selected from nitrogen, oxygen, or sulfur. In some embodiments, $R^y$ is a 6-membered monocyclic heteroaryl ring having 1-4 heteroatoms independently selected from nitrogen, oxygen, or sulfur.

In some embodiments, $R^y$ is a 3-7 membered saturated or partially unsaturated heterocyclic ring having 1-3 heteroatoms independently selected from nitrogen, oxygen, or sulfur. In some embodiments, $R^y$ is a 3-membered saturated or partially unsaturated heterocyclic ring having 1-2 heteroatoms independently selected from nitrogen, oxygen, or sulfur. In some embodiments, $R^y$ is a 4-membered saturated or partially unsaturated heterocyclic ring having 1-2 heteroatoms independently selected from nitrogen, oxygen, or sulfur. In some embodiments, $R^y$ is a 5-membered saturated or partially unsaturated heterocyclic ring having 1-3 heteroatoms independently selected from nitrogen, oxygen, or sulfur. In some embodiments, $R^y$ is a 6-membered saturated or partially unsaturated heterocyclic ring having 1-3 heteroatoms independently selected from nitrogen, oxygen, or sulfur. In some embodiments, $R^y$ is a 7-membered saturated or partially unsaturated heterocyclic ring having 1-3 heteroatoms independently selected from nitrogen, oxygen, or sulfur.

In some embodiments, $R^y$ is a 7-10 membered bicyclic saturated or partially unsaturated heterocyclic ring having 1-5 heteroatoms independently selected from nitrogen, oxygen, or sulfur.

In some embodiments, $R^y$ is an 8-10 membered bicyclic heteroaryl ring having 1-5 heteroatoms independently selected from nitrogen, oxygen, or sulfur.

In certain embodiments, $R^z$ is independently halogen. In some embodiments, $R^z$ is —F. In some embodiments, $R^z$ is —Cl. In some embodiments, $R^z$ is —Br. In some embodiments, $R^z$ is —I.

In some embodiments, $R^z$ is —OR', —N(R')$_2$, —NR'C(O)R', —NR'C(O)OR', —NR'C(O)N(R')$_2$, —NR'SO$_2$R', —NR'SO$_2$N(R')$_2$, or —NR'OR', wherein each of R' is independently as defined above and described herein.

In some embodiments, $R^z$ is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur.

In some embodiments, $R^z$ is optionally substituted $C_{1-20}$ aliphatic. In some embodiments, $R^z$ is optionally substituted $C_{1-20}$ alkyl. In some embodiments, $R^z$ is optionally substituted $C_{1-12}$ aliphatic. In some embodiments, $R^z$ is optionally substituted $C_{1-12}$ alkyl. In some embodiments, $R^z$ is optionally substituted $C_{1-6}$ aliphatic. In some embodiments, $R^z$ is optionally substituted $C_{1-6}$ alkyl. In some embodiments, $R^z$ is optionally substituted hexyl, pentyl, butyl, propyl, ethyl or methyl. In some embodiments, $R^z$ is optionally substituted hexyl. In some embodiments, $R^z$ is optionally substituted pentyl. In some embodiments, $R^z$ is optionally substituted butyl. In some embodiments, $R^z$ is optionally substituted propyl. In some embodiments, $R^z$ is optionally substituted ethyl. In some embodiments, $R^z$ is optionally substituted methyl. In some embodiments, $R^z$ is hexyl. In some embodiments, $R^z$ is pentyl. In some embodiments, $R^z$ is butyl. In some embodiments, $R^z$ is propyl. In some embodiments, $R^z$ is ethyl. In some embodiments, $R^z$ is methyl. In some embodiments, $R^z$ is isopropyl.

In some embodiments, $R^z$ optionally substituted $C_{1-20}$ heteroaliphatic having 1-3 heteroatoms independently selected from nitrogen, oxygen, or sulfur. In some embodiments, $R^z$ is —OR', wherein R' is as defined above and described herein. In some embodiments, $R^z$ is —SR', wherein R' is as defined above and described herein. In some embodiments, $R^z$ is —N(R')$_2$, wherein each R' is independently as defined above and described herein.

In some embodiments, $R^z$ is R', wherein R' is as defined above and described herein.

In some embodiments, $R^z$ is optionally substituted phenyl. In some embodiments, $R^z$ is optionally substituted phenyl wherein one or more substituents are halogen. In some embodiments, $R^z$ is optionally substituted phenyl wherein one or more substituents are —F. In some embodiments, $R^z$ is optionally substituted phenyl wherein one or more substituents are —Cl. In some embodiments, $R^z$ is optionally substituted phenyl wherein one or more substituents are —Br. In some embodiments, $R^z$ is optionally substituted phenyl wherein one or more substituents are —I. In some embodiments, $R^z$ is phenyl.

In some embodiments, $R^z$ is a 3-7 membered saturated or partially unsaturated carbocyclic ring. In some embodiments, $R^z$ is a 3-membered saturated or partially unsaturated carbocyclic ring. In some embodiments, $R^z$ is a 4-membered saturated or partially unsaturated carbocyclic ring. In some embodiments, $R^z$ is a 5-membered saturated or partially unsaturated carbocyclic ring. In some embodiments, $R^z$ is a 6-membered saturated or partially unsaturated carbocyclic ring. In some embodiments, $R^z$ is a 7-membered saturated or partially unsaturated carbocyclic ring.

In some embodiments, $R^z$ is an 8-10 membered bicyclic saturated, partially unsaturated or aryl ring. In some embodiments, $R^z$ is an 8-10 membered bicyclic saturated ring. In some embodiments, $R^z$ is an 8-10 membered bicyclic partially unsaturated ring. In some embodiments, $R^z$ is an 8-10 membered bicyclic aryl ring.

In some embodiments, $R^z$ is a 5-6 membered monocyclic heteroaryl ring having 1-4 heteroatoms independently selected from nitrogen, oxygen, or sulfur. In some embodiments, $R^z$ is a 5-membered monocyclic heteroaryl ring having 1-4 heteroatoms independently selected from nitrogen, oxygen, or sulfur. In some embodiments, $R^z$ is a 6-membered monocyclic heteroaryl ring having 1-4 heteroatoms independently selected from nitrogen, oxygen, or sulfur.

In some embodiments, $R^z$ is a 3-7 membered saturated or partially unsaturated heterocyclic ring having 1-3 heteroatoms independently selected from nitrogen, oxygen, or sulfur.

In some embodiments, $R^z$ is a 7-10 membered bicyclic saturated or partially unsaturated heterocyclic ring having 1-5 heteroatoms independently selected from nitrogen, oxygen, or sulfur. In some embodiments, $R^z$ is a 3-membered saturated or partially unsaturated heterocyclic ring having 1-2 heteroatoms independently selected from nitrogen, oxygen, or sulfur. In some embodiments, $R^z$ is a 4-membered saturated or partially unsaturated heterocyclic ring having 1-2 heteroatoms independently selected from nitrogen, oxygen, or sulfur. In some embodiments, $R^z$ is a 5-membered saturated or partially unsaturated heterocyclic ring having 1-3 heteroatoms independently selected from nitrogen, oxygen, or sulfur. In some embodiments, $R^z$ is a 6-membered saturated or partially unsaturated heterocyclic ring having 1-3 heteroatoms independently selected from nitrogen, oxygen, or sulfur. In some embodiments, $R^z$ is a 7-membered saturated or partially unsaturated heterocyclic ring having 1-3 heteroatoms independently selected from nitrogen, oxygen, or sulfur.

In some embodiments, $R^z$ is an 8-10 membered bicyclic heteroaryl ring having 1-5 heteroatoms independently selected from nitrogen, oxygen, or sulfur.

In some embodiments, each of $R^y$ and $R^z$ is independently an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur. In some embodiments, each of $R^y$ and $R^z$ is independently an optionally substituted group selected from $C_{1-20}$ aliphatic, phenyl, an 8-10 membered bicyclic aryl ring, a 5-6 membered monocyclic heteroaryl ring having 1-4 heteroatoms independently selected from nitrogen, oxygen, or sulfur, or an 8-10 membered bicyclic heteroaryl ring having 1-5 heteroatoms independently selected from nitrogen, oxygen, or sulfur. In some embodiments, each of $R^y$ and $R^z$ is independently an optionally substituted group selected from $C_{1-20}$ aliphatic, phenyl, and a 5-6 membered monocyclic heteroaryl ring having 1-4 heteroatoms independently selected from nitrogen, oxygen. In some embodiments, each of $R^y$ and $R^z$ is independently an optionally substituted group selected from $C_{1-20}$ aliphatic and phenyl.

In some embodiments, each $R^y$ and $R^z$ is independently R', wherein R' is as defined above and described herein.

In some embodiments, each of $R^y$ and $R^z$ is independently optionally substituted $C_{1-20}$ aliphatic. In some embodiments, each of $R^y$ and $R^z$ is independently optionally substituted $C_{1-12}$ aliphatic. In some embodiments, each of $R^y$ and $R^z$ is independently optionally substituted $C_{1-6}$ aliphatic. In some embodiments, each of $R^y$ and $R^z$ is independently optionally substituted $C_{1-6}$ alkyl. In some embodiments, each of $R^y$ and $R^z$ is independently optionally substituted hexyl. In some embodiments, each of $R^y$ and $R^z$ is independently optionally substituted pentyl. In some embodiments, each of $R^y$ and $R^z$ is independently optionally substituted butyl. In some embodiments, each of $R^y$ and $R^z$ is independently optionally substituted propyl. In some embodiments, each of $R^y$ and $R^z$ is independently optionally substituted ethyl. In some embodiments, each of $R^y$ and $R^z$ is independently optionally substituted methyl. In some embodiments, each of $R^y$ and $R^z$ is hexyl. In some embodiments, each of $R^y$ and $R^z$ is pentyl. In some embodiments, each of $R^y$ and $R^z$ is butyl. In some embodiments, each of $R^y$ and $R^z$ is propyl. In some embodiments, each of $R^y$ and $R^z$ is ethyl. In some embodiments, each of $R^y$ and $R^z$ is methyl. In some embodiments, each of $R^y$ and $R^z$ is isopropyl.

In some embodiments, each of $R^y$ and $R^z$ is independently optionally substituted phenyl. In some embodiments, each of $R^y$ and $R^z$ is independently phenyl.

As generally defined above, each R' is independently hydrogen or an optionally substituted group selected from $C_{1-6}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or:

two R' groups on the same nitrogen atom are optionally taken together with the nitrogen atom to form an optionally substituted 3-8 membered, saturated, partially unsaturated, or aryl ring having 1-4 heteroatoms independently selected from nitrogen, oxygen, or sulfur.

In some embodiments, R' is hydrogen.

In some embodiments, R' is an optionally substituted group selected from $C_{1-6}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur. In some embodiments, two R' groups on the same nitrogen atom are optionally taken together with the nitrogen atom to form an optionally substituted 3-8 membered, saturated, partially unsaturated, or aryl ring having 1-4 heteroatoms independently selected from nitrogen, oxygen, or sulfur.

In some embodiments, R is optionally substituted $C_{1-6}$ aliphatic. In some embodiments, R' is optionally substituted $C_{1-6}$ alkyl. In some embodiments, R' is optionally substituted hexyl, pentyl, butyl, propyl, ethyl or methyl. In some embodiments, R' is optionally substituted hexyl. In some embodiments, R' is optionally substituted pentyl. In some embodiments, R' is optionally substituted butyl. In some embodiments, R' is optionally substituted propyl. In some embodiments, R' is optionally substituted ethyl. In some embodiments, R' is optionally substituted methyl. In some embodiments, R' is hexyl. In some embodiments, R' is pentyl. In some embodiments, R' is butyl. In some embodiments, R' is propyl. In some embodiments, R' is ethyl. In some embodiments, R' is methyl. In some embodiments, R' is isopropyl. In some embodiments, R' is tert-butyl. In some embodiments, R' is —C(Me)$_2$Ph.

In some embodiments, R is optionally substituted phenyl. In some embodiments, R' is optionally substituted phenyl wherein one or more substituents are halogen. In some embodiments, R' is optionally substituted phenyl wherein one or more substituents are —F. In some embodiments, R' is optionally substituted phenyl wherein one or more substituents are —Cl. In some embodiments, R' is optionally substituted phenyl wherein one or more substituents are —Br. In some embodiments, R' is optionally substituted phenyl wherein one or more substituents are —I. In some embodiments, R' is phenyl.

In some embodiments, R' is a 3-7 membered saturated or partially unsaturated carbocyclic ring. In some embodiments, R' is a 3-membered saturated or partially unsaturated carbocyclic ring. In some embodiments, R' is a 4-membered saturated or partially unsaturated carbocyclic ring. In some embodiments, R' is a 5-membered saturated or partially unsaturated carbocyclic ring. In some embodiments, R' is a 6-membered saturated or partially unsaturated carbocyclic ring. In some embodiments, R' is a 7-membered saturated or partially unsaturated carbocyclic ring. In some embodiments, R' is an optionally substituted cycloheptyl. In some embodiments, R' is an optionally substituted cyclohexyl. In some embodiments, R' is an optionally substituted cyclopentyl. In some embodiments, R' is an optionally substituted cyclobutyl. In some embodiments, R' is an optionally substituted cyclopropyl.

In some embodiments, R' is an 8-10 membered bicyclic saturated, partially unsaturated or aryl ring. In some embodiments, R' is an 8-10 membered bicyclic saturated ring. In some embodiments, R' is an 8-10 membered bicyclic partially unsaturated ring. In some embodiments, R' is an 8-10 membered bicyclic aryl ring.

In some embodiments, R' is a 5-6 membered monocyclic heteroaryl ring having 1-4 heteroatoms independently selected from nitrogen, oxygen, or sulfur. In some embodiments, R' is a substituted 5-6 membered monocyclic heteroaryl ring having 1-3 heteroatoms independently selected from nitrogen, oxygen, or sulfur. In some embodiments, R' is an unsubstituted 5-6 membered monocyclic heteroaryl ring having 1-3 heteroatoms independently selected from nitrogen, oxygen, or sulfur. In some embodiments, R' is a 5-membered monocyclic heteroaryl ring having 1-4 heteroatoms independently selected from nitrogen, oxygen, or sulfur. In some embodiments, R' is a 6-membered monocyclic heteroaryl ring having 1-4 heteroatoms independently selected from nitrogen, oxygen, or sulfur.

In some embodiments, R' is an optionally substituted 5-membered monocyclic heteroaryl ring having 1-3 heteroatoms independently selected from nitrogen, oxygen or sulfur. In some embodiments, R' is an optionally substituted 6-membered monocyclic heteroaryl ring having 1-3 heteroatoms independently selected from nitrogen, oxygen, or sulfur.

In some embodiments, R' is an optionally substituted 5-membered monocyclic heteroaryl ring having 1 heteroatom selected from nitrogen, oxygen, or sulfur. In some embodiments, R' is selected from pyrrolyl, furanyl, or thienyl.

In some embodiments, R' is an optionally substituted 5-membered heteroaryl ring having two heteroatoms independently selected from nitrogen, oxygen, or sulfur. In certain embodiments, R' is an optionally substituted 5-membered heteroaryl ring having one nitrogen atom, and an additional heteroatom selected from sulfur or oxygen. Exemplary R' groups include optionally substituted pyrazolyl, imidazolyl, thiazolyl, isothiazolyl, oxazolyl or isoxazolyl.

In some embodiments, R' is a 6-membered heteroaryl ring having 1-3 nitrogen atoms. In other embodiments, R' is an optionally substituted 6-membered heteroaryl ring having 1-2 nitrogen atoms. In some embodiments, R' is an optionally substituted 6-membered heteroaryl ring having two nitrogen atoms. In certain embodiments, R' is an optionally substituted 6-membered heteroaryl ring having one nitrogen atom. Exemplary R' groups include optionally substituted pyridinyl, pyrimidinyl, pyrazinyl, pyridazinyl, triazinyl, or tetrazinyl.

In some embodiments, R' is an optionally substituted 3-7 membered saturated or partially unsaturated heterocyclic ring having 1-2 heteroatoms independently selected from nitrogen, oxygen, or sulfur. In some embodiments, R' is a substituted 3-7 membered saturated or partially unsaturated heterocyclic ring having 1-2 heteroatoms independently selected from nitrogen, oxygen, or sulfur. In some embodiments, R' is an unsubstituted 3-7 membered saturated or partially unsaturated heterocyclic ring having 1-2 heteroatoms independently selected from nitrogen, oxygen, or sulfur.

In certain embodiments, R' is an optionally substituted 5-6 membered partially unsaturated monocyclic ring having 1-2 heteroatoms independently selected from nitrogen, oxygen, or sulfur. In certain embodiments, R' is an optionally substituted tetrahydropyridinyl, dihydrothiazolyl, dihydrooxazolyl, or oxazolinyl group.

In some embodiments, R' is an optionally substituted 6-membered saturated or partially unsaturated heterocyclic ring having 1-2 heteroatoms independently selected from nitrogen, oxygen, or sulfur. In some embodiments, R' is an optionally substituted 6-membered partially unsaturated heterocyclic ring having 2 heteroatoms independently selected from nitrogen, oxygen, or sulfur. In some embodiments, R' is an optionally substituted 6-membered partially unsaturated heterocyclic ring having 2 oxygen atom.

In certain embodiments, R' is an optionally substituted 5-6 membered partially unsaturated monocyclic ring having 1-2 heteroatoms independently selected from nitrogen, oxygen, or sulfur. In certain embodiments, R' is an optionally substituted tetrahydropyridinyl, dihydrothiazolyl, dihydrooxazolyl, or oxazolinyl group.

In certain embodiments, R' is optionally substituted oxiranyl, oxetanyl, tetrahydrofuranyl, tetrahydropyranyl, oxepaneyl, aziridineyl, azetidineyl, pyrrolidinyl, piperidinyl, azepanyl, thiiranyl, thietanyl, tetrahydrothiophenyl, tetrahydrothiopyranyl, thiepanyl, dioxolanyl, oxathiolanyl, oxazolidinyl, imidazolidinyl, thiazolidinyl, dithiolanyl, dioxanyl, morpholinyl, oxathianyl, piperazinyl, thiomorpholinyl, dithianyl, dioxepanyl, oxazepanyl, oxathiepanyl, dithiepanyl, diazepanyl, dihydrofuranonyl, tetrahydropyranonyl, oxepanonyl, pyrolidinonyl, piperidinonyl, azepanonyl, dihydrothiophenonyl, tetrahydrothiopyranonyl, thiepanonyl, oxazolidinonyl, oxazinanonyl, oxazepanonyl, dioxolanonyl, dioxanonyl, dioxepanonyl, oxathiolinonyl, oxathianonyl, oxathiepanonyl, thiazolidinonyl, thiazinanonyl, thiazepanonyl, imidazolidinonyl, tetrahydropyrimidinonyl, diazepanonyl, imidazolidinedionyl, oxazolidinedionyl, thiazolidinedionyl, dioxolanedionyl, oxathiolanedionyl, piperazinedionyl, morpholinedionyl, thiomorpholinedionyl, tetrahydropyranyl, tetrahydrofuranyl, morpholinyl, thiomorpholinyl, piperidinyl, piperazinyl, pyrrolidinyl, tetrahydrothiophenyl, or tetrahydrothiopyranyl.

In some embodiments, R' is a 7-10 membered bicyclic saturated or partially unsaturated heterocyclic ring having 1-5 heteroatoms independently selected from nitrogen, oxygen, or sulfur. In some embodiments, R' is an optionally substituted indolinyl. In some embodiments, R' is an optionally substituted isoindolinyl. In some embodiments, R' is an optionally substituted 1, 2, 3, 4-tetrahydroquinoline. In some embodiments, R' is an optionally substituted 1, 2, 3, 4-tetrahydroisoquinoline.

In some embodiments, R is an 8-10 membered bicyclic heteroaryl ring having 1-5 heteroatoms independently selected from nitrogen, oxygen, or sulfur. In some embodiments, R' is an optionally substituted 5,6-fused heteroaryl ring having 1-5 heteroatoms independently selected from nitrogen, oxygen, or sulfur. In other embodiments, R' is an optionally substituted 5,6-fused heteroaryl ring having 1-2 heteroatoms independently selected from nitrogen, oxygen, or sulfur. In certain embodiments, R' is an optionally substituted 5,6-fused heteroaryl ring having 1 heteroatom independently selected from nitrogen, oxygen, or sulfur. In some embodiments, R' is an optionally substituted indolyl. In some embodiments, R' is an optionally substituted azabicyclo[3.2.1]octanyl. In certain embodiments, R' is an optionally substituted 5,6-fused heteroaryl ring having 2 heteroatoms independently selected from nitrogen, oxygen, or sulfur. In some embodiments, R' is an optionally substituted azaindolyl. In some embodiments, R' is an optionally substituted benzimidazolyl. In some embodiments, R' is an optionally substituted benzothiazolyl. In some embodiments, R' is an optionally substituted benzoxazolyl. In some embodiments, R' is an optionally substituted indazolyl. In certain embodiments, R' is an optionally substituted 5,6-fused heteroaryl ring having 3 heteroatoms independently selected from nitrogen, oxygen, or sulfur.

In certain embodiments, R' is an optionally substituted 6,6-fused heteroaryl ring having 1-4 heteroatoms independently selected from nitrogen, oxygen, or sulfur. In some embodiments, R' is an optionally substituted 6,6-fused heteroaryl ring having 1-2 heteroatoms independently selected from nitrogen, oxygen, or sulfur. In other embodiments, R' is an optionally substituted 6,6-fused heteroaryl ring having 1 heteroatom independently selected from nitrogen, oxygen, or sulfur. In some embodiments, R' is an optionally substituted quinolinyl. In some embodiments, R' is an optionally substituted isoquinolinyl. According to one aspect, R' is an optionally substituted 6,6-fused heteroaryl ring having 2 heteroatoms independently selected from nitrogen, oxygen, or sulfur. In some embodiments, R' is a quinazoline or a quinoxaline.

In some embodiments, each of $R^x$, $R^y$, and $R^z$ is independently R', wherein R' is as defined above and described herein and is not hydrogen. In some embodiments, $R^x$ is R', wherein R' is as defined above and described herein and R' is not hydrogen. In some embodiments, $R^y$ is R', wherein R' is as defined above and described herein and R' is not hydrogen. In some embodiments, $R^z$ is R', wherein R' is as defined above and described herein and R' is not hydrogen.

In some embodiments,

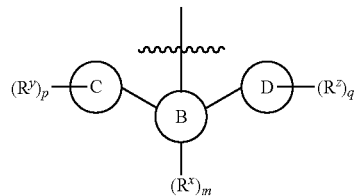

has the structure of:

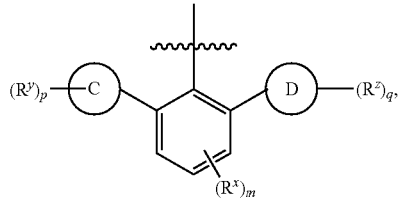

wherein each variable is independently as defined above and described herein.

In some embodiments,

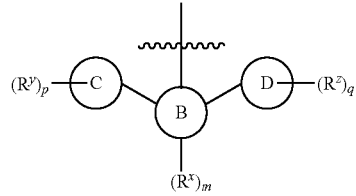

has the structure of:

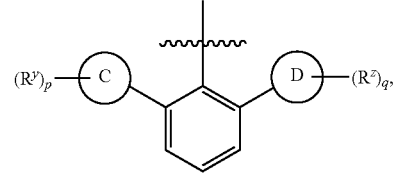

wherein each variable is independently as defined above and described herein.

In some embodiments,

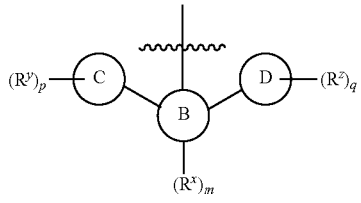

has the structure of:

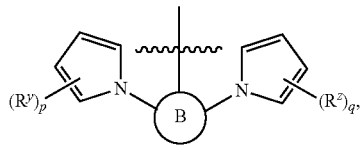

wherein each variable is independently as defined above and described herein.

In some embodiments,

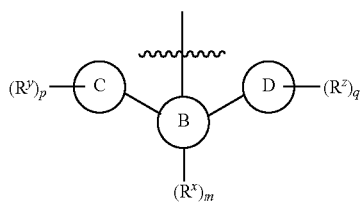

has the structure of:

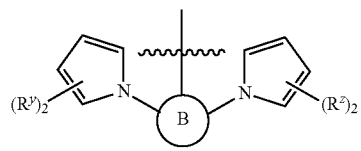

wherein each variable is independently as defined above and described herein.

In some embodiments,

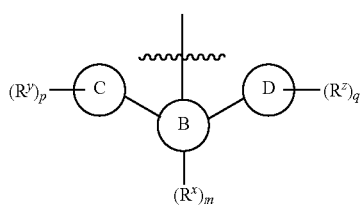

has the structure of:

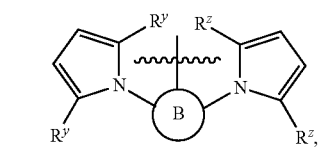

wherein each variable is independently as defined above and described herein.

In some embodiments,

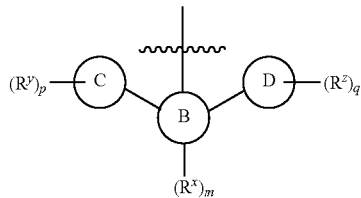

has the structure of:

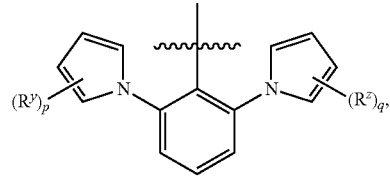

wherein each variable is independently as defined above and described herein.

In some embodiments,

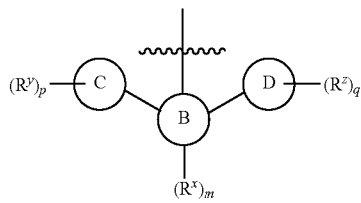

has the structure of:

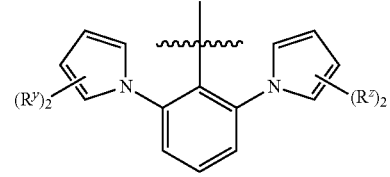

wherein each variable is independently as defined above and described herein.

In some embodiments,

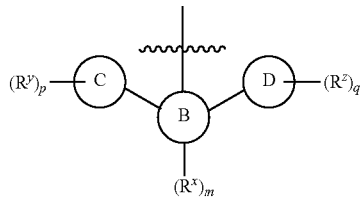

has the structure of:

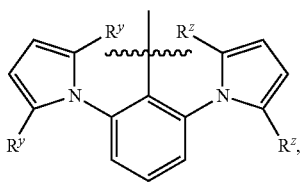

wherein each variable is independently as defined above and described herein.

As defined generally above, $R^4$ is an optionally substituted 5-membered monocyclic heteroaryl ring having 1-2 nitrogen atoms. In some embodiments, $R^4$ is an optionally substituted 5-membered monocyclic heteroaryl ring having 1-2 nitrogen atoms, wherein $R^4$ is bonded to M through a nitrogen atom.

In some embodiments, $R^4$ is an optionally substituted 5-membered monocyclic heteroaryl ring having 1-2 nitrogen atoms. In some embodiments, $R^4$ is an optionally substituted 5-membered monocyclic heteroaryl ring having one nitrogen atom. In some embodiments, $R^4$ is optionally substituted pyrrolyl. In some embodiments, $R^4$ is optionally substituted 1-pyrrolyl. In some embodiments, $R^4$ is an optionally substituted 5-membered monocyclic heteroaryl ring having two nitrogen atoms. In some embodiments, $R^4$ is optionally substituted imidazolyl. In some embodiments, $R^4$ is optionally substituted pyrazolyl.

In some embodiments, $R^4$ is optionally substituted pyrrolyl. In some embodiments, $R^4$ is optionally substituted 1-pyrrolyl. In some embodiments, $R^4$ is optionally substituted pyrrolyl having the structure of

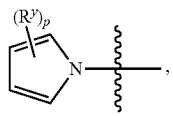

wherein each of p and $R^y$ is independently as defined above and described herein. In some embodiments, $R^4$ is disubstituted pyrrolyl. In some embodiments, $R^4$ is disubstituted pyrrolyl having the structure of

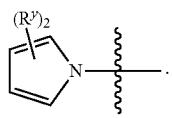

In some embodiments, $R^4$ is 2,5-disubstituted pyrrolyl. In some embodiments, $R^4$ is 2,5-disubstituted pyrrolyl having the structure of

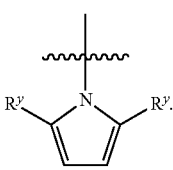

In some embodiments, $R^4$ is 2,5-disubstituted pyrrolyl having the structure of

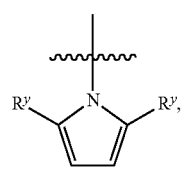

wherein each $R^y$ is independently R'. In some embodiments, $R^4$ is 2,5-disubstituted pyrrolyl having the structure of

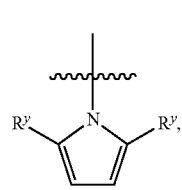

wherein each $R^y$ is independently hydrogen or $C_{1-4}$ aliphatic. In some embodiments, $R^4$ is 2,5-disubstituted pyrrolyl having the structure of

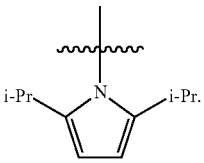 [SMILES: *n1c(C(C)C)ccc1C(C)C]

In some embodiments, $R^4$ is 2,5-disubstituted pyrrolyl having the structure of

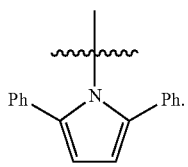

In some embodiments, $R^4$ is

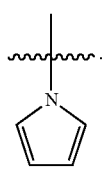

In some embodiments, $R^4$ is

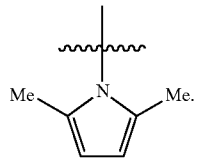

In some embodiments, $R^4$ is optionally substituted imidazolyl. In some embodiments, $R^4$ is optionally substituted imidazolyl having the structure of

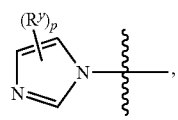

wherein each of p and $R^y$ is independently as defined above and described herein. In some embodiments, $R^4$ is disubstituted imidazolyl. In some embodiments, $R^4$ is disubstituted imidazolyl having the structure of

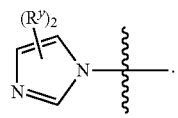

In some embodiments, $R^4$ is 2,5-disubstituted imidazolyl. In some embodiments, $R^4$ is 2,5-disubstituted imidazolyl having the structure of

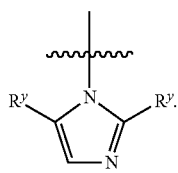

In some embodiments, $R^4$ is 2,5-disubstituted pyrrolyl having the structure of

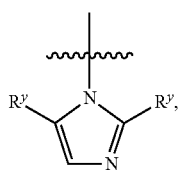

wherein each $R^y$ is independently $R'$. In some embodiments, $R^4$ is 2,5-disubstituted pyrrolyl having the structure of

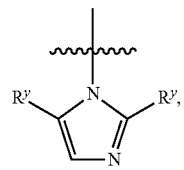

wherein each $R^y$ is independently hydrogen or $C_{1-4}$ aliphatic. In some embodiments, $R^4$ is 2,5-disubstituted pyrrolyl having the structure of

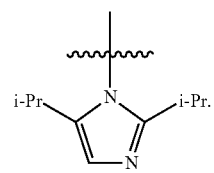 [SMILES: *n1c(C(C)C)cnc1C(C)C]

In some embodiments, $R^4$ is 2,5-disubstituted pyrrolyl having the structure of

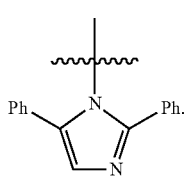

In some embodiments, $R^4$ is optionally substituted pyrazolyl. In some embodiments, $R^4$ is optionally substituted pyrazolyl having the structure of

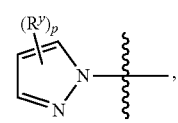

wherein each of p and $R^y$ is independently as defined above and described herein. In some embodiments, $R^4$ is disubstituted pyrazolyl. In some embodiments, $R^4$ is disubstituted pyrazolyl having the structure of

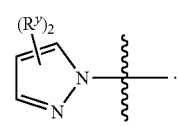

As defined above and described herein, $R^{2'}$ and $R^{3'}$ are taken together with the intervening metal atom to form an optionally substituted 3-8 membered saturated or partially unsaturated ring having, in addition to the intervening metal atom, 0-4 heteroatoms independently selected from nitrogen, oxygen, or sulfur. In some embodiments, $R^{2'}$ and $R^{3'}$ are taken together with the intervening metal atom to form an optionally substituted 3-8 membered saturated or partially unsaturated ring, wherein each ring atom is either M or carbon.

In some embodiments, $R^{2'}$ and $R^{3'}$ are taken together with the intervening metal atom to form an optionally substituted 3-8 membered saturated ring having, in addition to the intervening metal atom, 0-4 heteroatoms independently selected from nitrogen, oxygen, or sulfur. In some embodiments, $R^{2'}$ and $R^{3'}$ are taken together with the intervening metal atom to form an optionally substituted 3-8 membered saturated ring having, in addition to the intervening metal atom, 0-2 heteroatoms independently selected from nitrogen, oxygen, or sulfur. In some embodiments, $R^{2'}$ and $R^{3'}$ are taken together with the intervening metal atom to form an optionally substituted 5-6 membered saturated ring having, in addition to the intervening metal atom, 0-4 heteroatoms independently selected from nitrogen, oxygen, or sulfur. In some embodiments, $R^{2'}$ and $R^{3'}$ are taken together with the intervening metal atom to form an optionally substituted 5-6 membered saturated ring having, in addition to the intervening metal atom, 0-2 heteroatoms independently selected from nitrogen, oxygen, or sulfur. In some embodiments, $R^{2'}$ and $R^{3'}$ are taken together with the intervening metal atom to form an optionally substituted 3-4 membered saturated ring having, in addition to the intervening metal atom, 0-4 heteroatoms independently selected from nitrogen, oxygen, or sulfur. In some embodiments, $R^{2'}$ and $R^{3'}$ are taken together with the intervening metal atom to form an optionally substituted 3-4 membered saturated ring having, in addition to the intervening metal atom, 0-2 heteroatoms independently selected from nitrogen, oxygen, or sulfur. In some embodiments, $R^{2'}$ and $R^{3'}$ are taken together with the intervening metal atom to form an optionally substituted 3-5 membered saturated ring, wherein each ring atom is either M or carbon.

In some embodiments, $R^{2'}$ and $R^{3'}$ are taken together with the intervening metal atom to form an optionally substituted 3-membered saturated ring. In certain embodiments, $R^{2'}$ and $R^{3'}$ are taken together with the intervening metal atom to form a substituted 3-membered saturated ring. In certain embodiments, $R^{2'}$ and $R^{3'}$ are taken together with the intervening metal atom to form a 3-membered saturated ring unsubstituted at the ring carbon atoms. In certain embodiments, $R^{2'}$ and $R^{3'}$ are taken together with the intervening metal atom to form a metallacyclopropane ring optionally substituted at the ring carbon atoms. In certain embodiments, $R^{2'}$ and $R^{3'}$ are taken together with the intervening metal atom to form metallacyclopropane, wherein the ring carbon atoms of the metallacyclobutane are not substituted. In some embodiments, a compound of formula II wherein $R^{2'}$ and $R^{3'}$ are taken together with the intervening metal atom to form a metallacyclopropane ring can be considered as a compound comprising an olefin ligand. For example, a

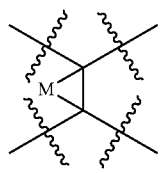

moiety may be considered as

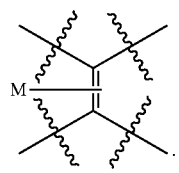

In certain embodiments, $R^{2'}$ and $R^{3'}$ are taken together with the intervening metal atom to form an optionally substituted 4-membered saturated ring. In certain embodiments, $R^{2'}$ and $R^{3'}$ are taken together with the intervening metal atom to form a substituted 4-membered saturated ring. In certain embodiments, $R^{2'}$ and $R^{3'}$ are taken together with the intervening metal atom to form an unsubstituted 4-membered saturated ring. In certain embodiments, $R^{2'}$ and $R^{3'}$ are taken together with the intervening metal atom to form metallacyclobutane optionally substituted at the ring carbon atoms. In certain embodiments, $R^{2'}$ and $R^{3'}$ are taken together with the intervening metal atom to form metallacyclobutane, wherein the ring carbon atoms of the metallacyclobutane are not substituted.

In some embodiments, a compound of formula II has the structure of formula II-a:

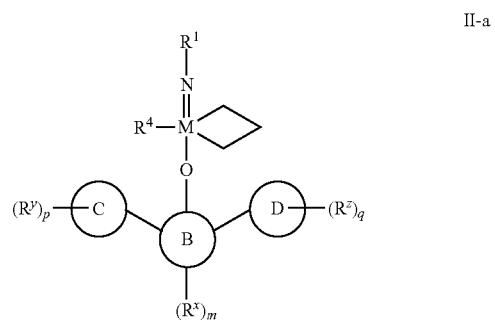

wherein each variable is independently as defined above and described herein.

In certain embodiments, $R^{2'}$ and $R^{3'}$ are taken together with the intervening metal atom to form an optionally substituted 5-membered saturated ring. In certain embodiments, $R^{2'}$ and $R^{3'}$ are taken together with the intervening metal atom to form a substituted 5-membered saturated ring. In certain embodiments, $R^{2'}$ and $R^{3'}$ are taken together with the intervening metal atom to form a 5-membered saturated ring unsubstituted at the ring carbon atoms. In certain embodiments, $R^{2'}$ and $R^{3'}$ are taken together with the intervening metal atom to form a metallacyclopentane ring optionally substituted at the ring carbon atoms. In certain embodiments, $R^{2'}$ and $R^{3'}$ are taken together with the intervening metal atom to form metallacyclopentane, wherein the ring carbon atoms of the metallacyclopentane are not substituted.

In some embodiments, $R^{2'}$ and $R^{3'}$ are taken together with the intervening metal atom to form an optionally substituted 3-8 membered partially unsaturated ring having, in addition to the intervening metal atom, 0-4 heteroatoms independently selected from nitrogen, oxygen, or sulfur. In some embodiments, $R^{2'}$ and $R^{3'}$ are taken together with the intervening metal atom to form an optionally substituted 3-8 membered partially unsaturated ring having, in addition to the intervening metal atom, 0-2 heteroatoms independently selected from nitrogen, oxygen, or sulfur. In some embodiments, $R^{2'}$ and $R^{3'}$ are taken together with the intervening metal atom to form an optionally substituted 5-6 membered partially unsaturated ring having, in addition to the intervening metal atom, 0-4 heteroatoms independently selected from nitrogen, oxygen, or sulfur. In some embodiments, $R^{2'}$ and $R^{3'}$ are taken together with the intervening metal atom to form an optionally substituted 5-6 membered partially unsaturated ring having, in addition to the intervening metal atom, 0-2 heteroatoms independently selected from nitrogen, oxygen, or sulfur. In some embodiments, $R^{2'}$ and $R^{3'}$ are taken together with the intervening metal atom to form an optionally substituted 3-4 membered partially unsaturated ring having, in addition to the intervening metal atom, 0-4 heteroatoms independently selected from nitrogen, oxygen, or sulfur. In some embodiments, $R^{2'}$ and $R^{3'}$ are taken together with the intervening metal atom to form an optionally substituted 3-4 membered partially unsaturated ring having, in addition to the intervening metal atom, 0-2 heteroatoms independently selected from nitrogen, oxygen, or sulfur.

In some embodiments, a compound of formula I has the structure of formula I-a:

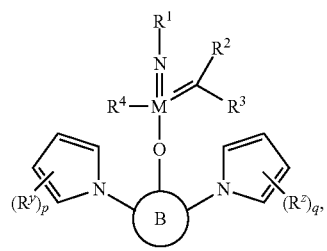

I-a wherein each variable is independently as defined above and described herein.

In some embodiments, a compound of formula I has the structure of formula I-b:

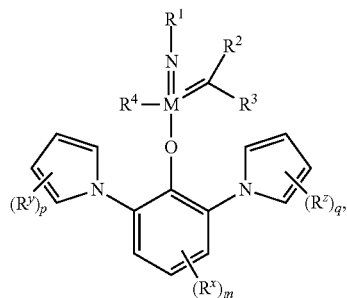

I-b wherein each variable is independently as defined above and described herein.

In some embodiments, a compound of formula I has the structure of formula I-c:

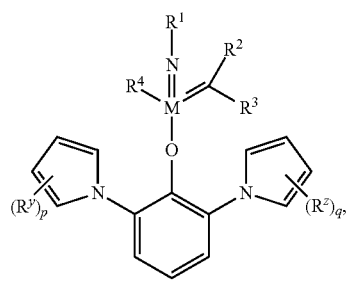

I-c wherein each variable is independently as defined above and described herein.

In some embodiments, a compound of formula I has the structure of formula I-d:

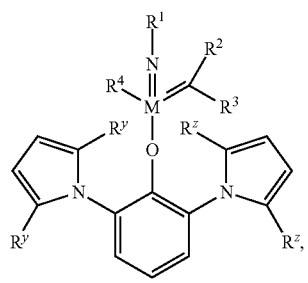

I-d wherein each variable is independently as defined above and described herein.

In some embodiments, a compound of formula II has the structure of formula II-b:

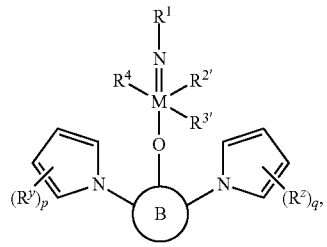

II-b wherein each variable is independently as defined above and described herein.

In some embodiments, a compound of formula II has the structure of formula II-c:

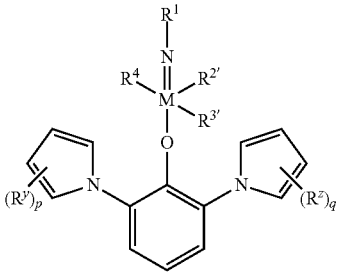

II-c wherein each variable is independently as defined above and described herein.

In some embodiments, a compound of formula II has the structure of formula II-d:

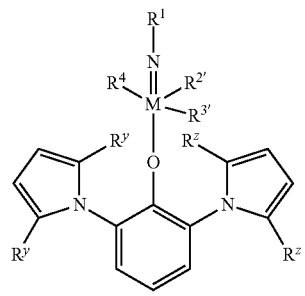

II-d wherein each variable is independently as defined above and described herein.

In some embodiments, a compound of formula III has the structure of formula III-a:

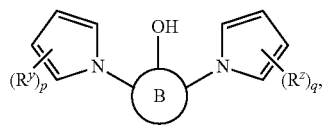

III-a wherein each variable is independently as defined above and described herein.

In some embodiments, a compound of formula III has the structure of formula III-b:

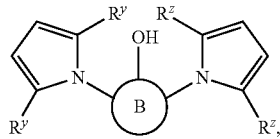

III-b wherein each variable is independently as defined above and described herein.

In some embodiments, a compound of formula III has the structure of formula III-c:

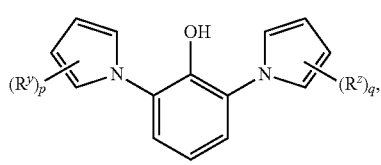

III-c wherein each variable is independently as defined above and described herein.

In some embodiments, a compound of formula III has the structure of formula III-d:

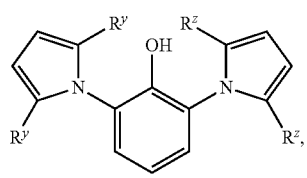

III-d wherein each variable is independently as defined above and described herein.

Exemplary compounds of formula I include but are not limited to those depicted below:

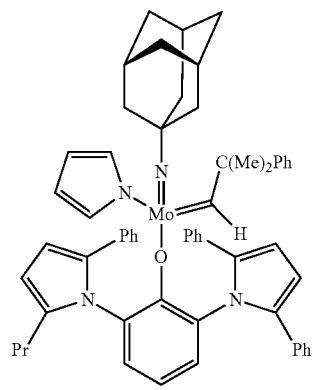

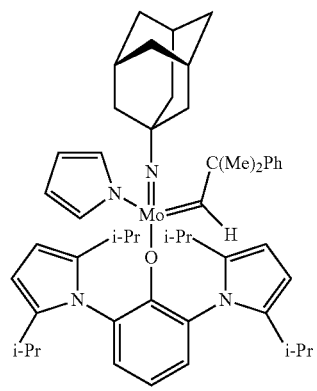

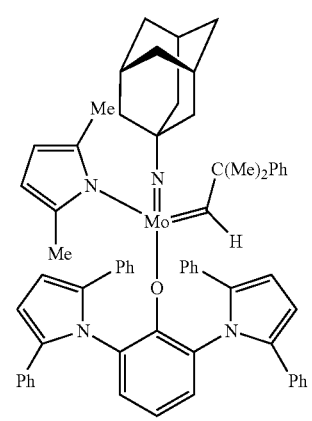

-continued

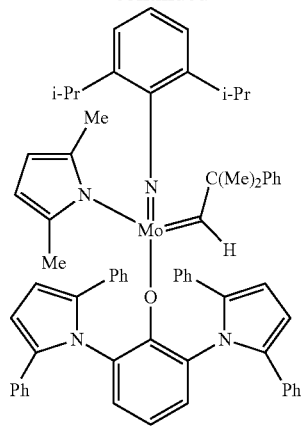

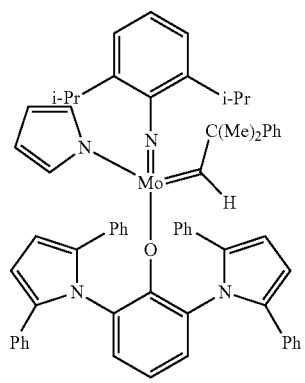

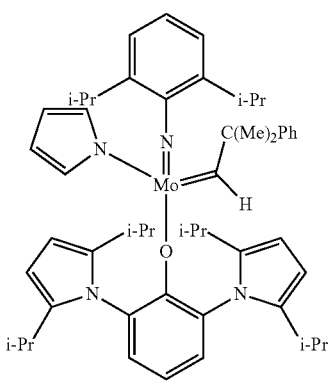

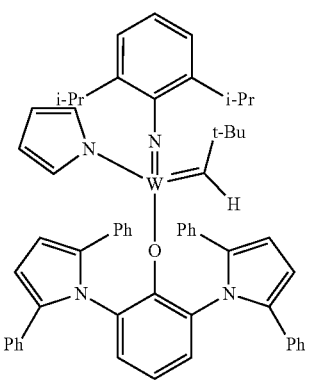

-continued

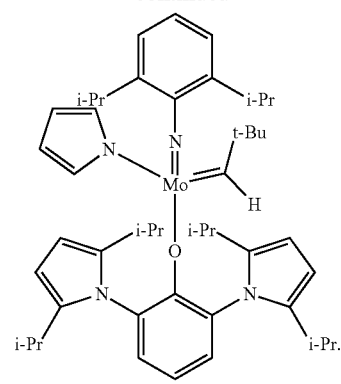

In some embodiments, a compound of formula II is

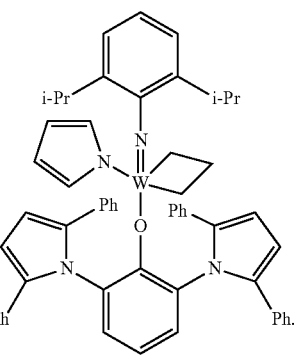

Exemplary compounds of formula III include but are not limited to those depicted below:

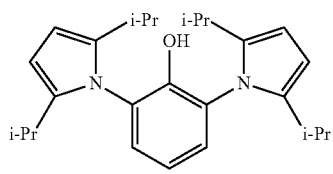

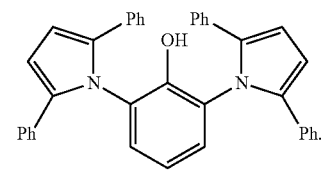

Exemplary Uses of Provided Compounds

In some embodiments, a provided compound of formula III is used to prepare compounds that promote metathesis reactions. In some embodiments, a provided compound that promotes metathesis reactions has the structure of formula I. In some embodiments, a provided compound that promotes metathesis reactions has the structure of formula II.

In some embodiments, the present invention provides a method for preparing a compound of formula I:

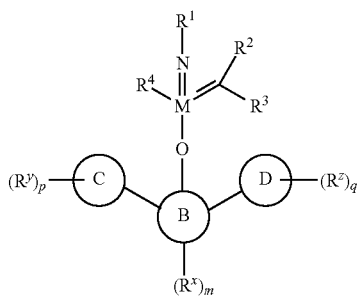

comprising:
(a) providing a first compound having the structure of formula IV:

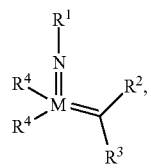

wherein each variable is independently as defined above and described herein;
(b) providing a second compound having the structure of formula III:

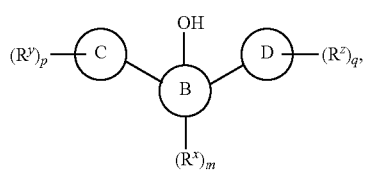

or its salt thereof;
wherein each variable is independently as defined above and described herein; and
(c) reacting the first compound with the second compound.

In some embodiments, the present invention provides a method for preparing a compound of formula II:

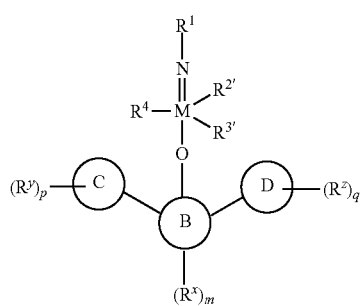

comprising:
(a) providing a first compound having the structure of formula II:

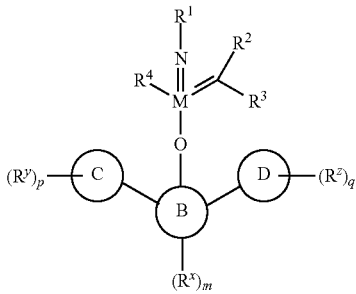

(b) reacting the first compound with an olefin.
In some embodiments, an olefin is ethylene.

In some embodiments, the present invention provides methods for performing highly efficient and Z-selection metathesis reactions. In some embodiments, the present invention provides a method comprising:
(a) providing a compound of formula I or II;
(b) reacting a first unsaturated bond and a second unsaturated bond to produce a product comprising an unsaturated bond;

In some embodiments, a compound in a provided method is a compound of formula I. In some embodiments, a compound in a provided method is a compound of formula II.

In some embodiments, a first unsaturated bond is an unsaturated carbon-carbon bond. In some embodiments, a second unsaturated bond is an unsaturated carbon-carbon bond. In some embodiments, both the first and the second unsaturated bonds are unsaturated carbon-carbon bonds. In some embodiments, a product comprising an unsaturated bond comprises an unsaturated carbon-carbon bond. In some embodiments, a product comprising an unsaturated bond comprises an unsaturated carbon-carbon bond, wherein the unsaturated carbon-carbon bond comprises a carbon atom from the first unsaturated bond and a carbon atom from the second unsaturated bond. In some embodiments, an unsaturated carbon-carbon bond is a double bond (C=C). In some embodiments, an unsaturated carbon-carbon bond is a triple bond (C≡C). In some embodiments, a first unsaturated bond is a carbon-carbon double bond (C=C). In some embodiments, a first unsaturated bond is a carbon-carbon triple bond (C≡C). In some embodiments, a second unsaturated bond is a carbon-carbon double bond (C=C). In some embodiments, a second unsaturated bond is a carbon-carbon triple bond (C≡C). In some embodiments, a product comprising an unsaturated bond comprises an unsaturated carbon-carbon bond. In some embodiments, a product comprising an unsaturated bond comprises a carbon-carbon double bond (C=C). In some embodiments, a product comprising an unsaturated bond comprises a carbon-carbon triple bond (C≡C). In some embodiments, both the first unsaturated bond and the second unsaturated bond are carbon-carbon double bond (C=C), and the product comprises a carbon-carbon double bond (C=C). In some embodiments, both the first unsaturated bond and the second unsaturated bond are carbon-carbon double bond (C=C), and the product comprises a carbon-carbon double bond (C=C), wherein the carbon-carbon double bond in the product comprises a carbon atom from the first unsaturated bond and a carbon atom from the second unsaturated bonds. In some embodiments, a first unsaturated bond is a carbon-carbon double bond (C=C), a second unsaturated bond is a carbon-carbon triple bond (C≡C), and the product comprises a carbon-carbon double bond (C=C).

In some embodiments, the present invention provides a method comprising:

(a) providing a compound of formula I or II; and
(b) reacting a first unsaturated carbon-carbon bond and a second unsaturated carbon-carbon bond to produce a product comprising an unsaturated carbon-carbon bond, wherein said unsaturated carbon-carbon bond in the product comprises one carbon atom from the first unsaturated carbon-carbon bond and one carbon atom from the second unsaturated carbon-carbon bond.

Highly efficient and Z-selective homocoupling of two olefins via metathesis reactions remains a major challenge in the field. Improved efficiency and/or selectivity are highly desirable. In some embodiments, a provided compound is particularly efficient in promoting homocoupling metathesis. In some embodiments, a provided compound is particularly efficient in promoting the homocoupling of terminal alkenes. In some embodiments, a terminal alkene is 1-octene. In some embodiments, a provided method comprising the use of a provided compound delivers up to 62% conversion and >95% Z-selectivity in the homocoupling of 1-octene in 10 minutes. Such high efficiency and selectivity are unexpected.

In some embodiments, the compound comprising the first unsaturated carbon-carbon bond and the compound comprising the second unsaturated carbon-carbon bond are identical. In some embodiments, the compound comprising the first unsaturated carbon-carbon bond is an olefin. In some embodiments, the compound comprising the second unsaturated carbon-carbon bond is an olefin. In some embodiments, both the compound comprising the first unsaturated carbon-carbon bond and the compound comprising the second unsaturated carbon-carbon bond are olefin. In some embodiments, both the compound comprising the first unsaturated carbon-carbon bond and the compound comprising the second unsaturated carbon-carbon bond are olefin, and the two compounds are identical.

In some embodiments, the present invention provides exemplary compounds and methods as follows:

E1. A compound of formula I:

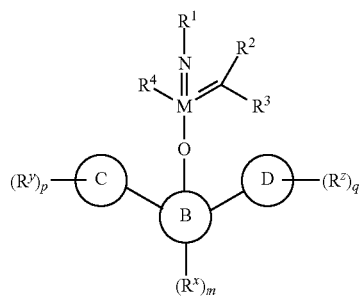

I wherein:
M is molybdenum or tungsten;
$R^1$ is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

each of $R^2$ and $R^3$ is independently R', —OR', —SR', —N(R')$_2$, —OC(O)R', —SOR', —SO$_2$R', —SO$_2$N(R')$_2$, —C(O)N(R')$_2$, —NR'C(O)R', or —NR'SO$_2$R';

m is 0-3;

Ring B is an optionally substituted group selected from phenyl or a 5-6 membered monocyclic heteroaryl ring having 1-4 heteroatoms independently selected from nitrogen, oxygen, or sulfur;

each of p and q is independently 0-4;

each of Ring C and Ring D is independently an optionally substituted 5-membered monocyclic heteroaryl ring having 1-4 nitrogen atoms;

each of $R^x$, $R^y$ and $R^z$ is independently halogen, —OR', —N(R')$_2$, —NR'C(O)R', —NR'C(O)OR', —NR'C(O)N(R')$_2$, —NR'SO$_2$R', —NR'SO$_2$N(R')$_2$, —NR'OR', or an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

$R^4$ is an optionally substituted 5-membered monocyclic heteroaryl ring having 1-2 nitrogen atoms; and each R' is independently hydrogen or an optionally substituted group selected from $C_{1-6}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or:

two R' groups on the same nitrogen atom are optionally taken together with the nitrogen atom to form an optionally substituted 3-8 membered, saturated, partially unsaturated, or aryl ring having 1-4 heteroatoms independently selected from nitrogen, oxygen, or sulfur.

E2. The compound of example E1, wherein each of $R^2$ and $R^3$ is independently R'.
E3. The compound of any one of the preceding examples, wherein one of $R^2$ and $R^3$ is hydrogen and the other is not hydrogen.
E4. The compound of any one of the preceding examples, wherein one of $R^2$ and $R^3$ is hydrogen and the other is optionally substituted $C_{1-20}$ aliphatic.
E5. The compound of any one of the preceding examples, wherein one of $R^2$ and $R^3$ is hydrogen and the other is —C(Me)$_3$ or —C(Me)$_2$Ph.
E6. A compound of formula II:

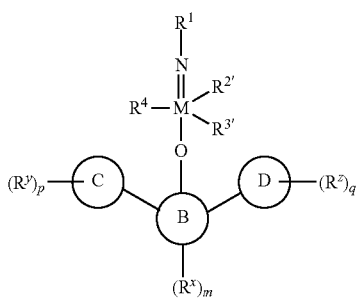

II wherein:
M is molybdenum or tungsten;
$R^1$ is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;
$R^{2'}$ and $R^{3'}$ are taken together with their intervening metal atoms to form an optionally substituted 3-8 membered saturated or partially unsaturated ring having, in addition to the intervening metal atom, 0-4 heteroatoms independently selected from nitrogen, oxygen, or sulfur;
m is 0-3;
Ring B is an optionally substituted group selected from phenyl or a 5-6 membered monocyclic heteroaryl ring having 1-4 heteroatoms independently selected from nitrogen, oxygen, or sulfur;
each of p and q is independently 0-4;
each of Ring C and Ring D is independently an optionally substituted 5-membered monocyclic heteroaryl ring having 1-4 nitrogen atoms;
each of $R^x$, $R^y$ and $R^z$ is independently halogen, —OR', —N(R')$_2$, —NR'C(O)R', —NR'C(O)OR', —NR'C(O)N(R')$_2$, —NR'SO$_2$R', —NR'SO$_2$N(R')$_2$, —NR'OR', or an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;
$R^4$ is an optionally substituted 5-membered monocyclic heteroaryl ring having 1-2 nitrogen atoms; and
each R' is independently hydrogen or an optionally substituted group selected from $C_{1-6}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or:
two R' groups on the same nitrogen atom are optionally taken together with the nitrogen atom to form an optionally substituted 3-8 membered, saturated, partially unsaturated, or aryl ring having 1-4 heteroatoms independently selected from nitrogen, oxygen, or sulfur.

E7. The compound of example E6, wherein $R^{2'}$ and $R^{3'}$ are taken together with M to form an optionally substituted 3-membered ring.
E8. The compound of example E6, wherein $R^{2'}$ and $R^{3'}$ are taken together with M to form an optionally substituted 4-membered ring.
E9. The compound of example E6, wherein the compound has the structure of formula II-a:

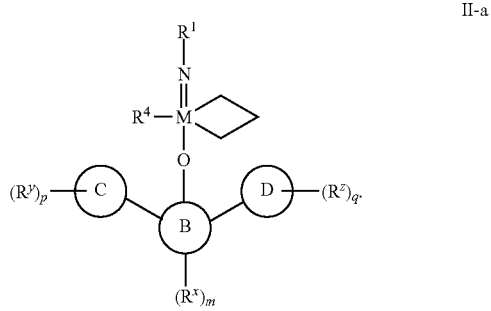

II-a

E10. The compound of example E6, wherein $R^{2'}$ and $R^{3'}$ are taken together with M to form an optionally substituted 5-membered ring.
E11. The compound of any one of the preceding examples, wherein $R^1$ is optionally substituted $C_{1-20}$ aliphatic.
E12. The compound of any one of the preceding examples, wherein $R^1$ is optionally substituted adamantyl.

E13. The compound of any one of examples E1-E10, wherein $R^1$ is optionally substituted phenyl.

E14. The compound of any one of examples E1-E10, wherein $R^1$ is selected from

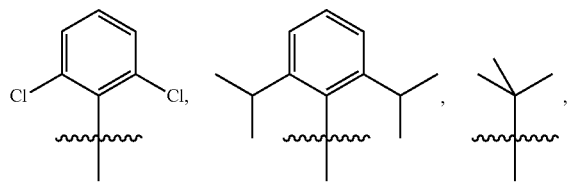

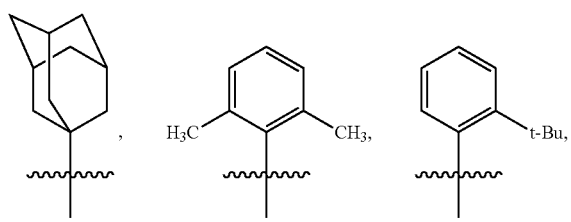

E15. The compound of any one of the preceding examples, wherein $R^4$ is bonded to M through a nitrogen atom.

E16. The compound of any one of the preceding examples, wherein $R^4$ is optionally substituted pyrrolyl.

E17. The compound of any one of the preceding examples, wherein $R^4$ is 2,5-disubstituted pyrrolyl.

E18. The compound of any one of examples E1-E15, wherein $R^4$ is

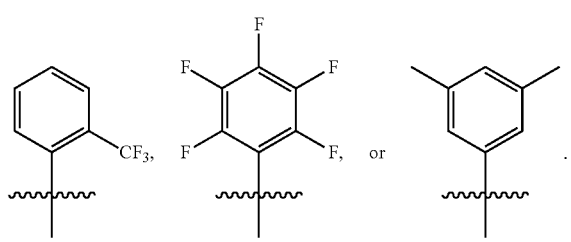

E19. The compound of example E18, wherein $R^4$ is

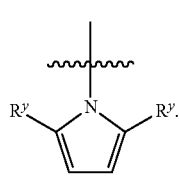

E20. The compound of example E18, wherein $R^4$ is

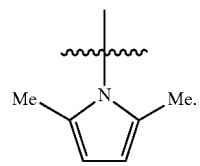

E21. The compound of any one of the preceding examples, wherein $R^1$ is

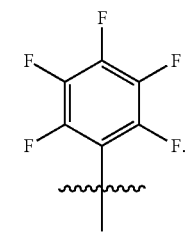

E22. The compound of any one of the preceding examples, wherein $R^1$ is

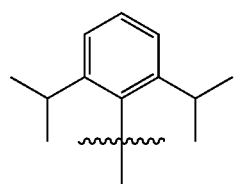

E23. The compound of any one of the preceding examples, wherein $R^1$ is

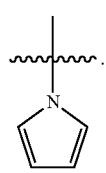 [SMILES: *n1cccc1]

E24. A compound of formula III:

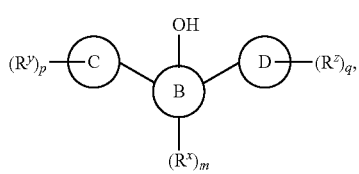

III or its salt thereof.

E25. The compound of any one of the preceding examples, wherein Ring C is optionally substituted pyrrolyl, imidazolyl or pyrazolyl.

E26. The compound of any one of examples E1-E24, wherein Ring C is

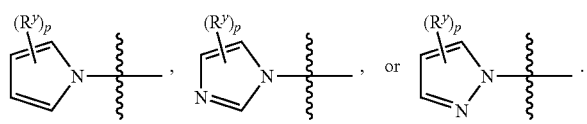

E27. The compound of example E26, wherein Ring C is

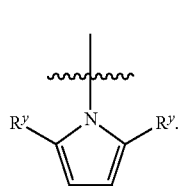

E28. The compound of example E27, wherein Ring C is

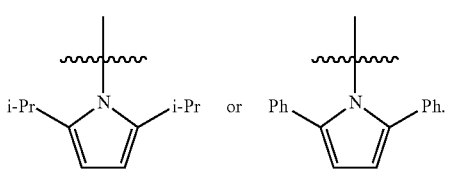 [SMILES: *n1c(C(C)C)ccc1C(C)C ; "or" ; *n1c(-c2ccccc2)ccc1-c1ccccc1]

E29. The compound of any one of the preceding examples, wherein Ring D is optionally substituted pyrrolyl, imidazolyl or pyrazolyl.

E30. The compound of any one of examples E1-E28, wherein Ring D is

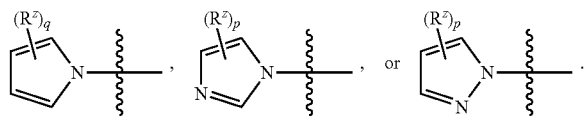

E31. The compound of example E30, wherein Ring D is

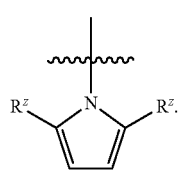

E32. The compound of example E31, wherein Ring D is

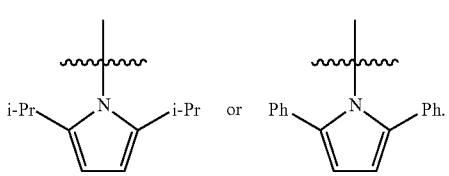 [SMILES: *n1c(C(C)C)ccc1C(C)C ; "or" ; *n1c(-c2ccccc2)ccc1-c1ccccc1]

E33. The compound of any one of the preceding examples, wherein Ring C and Ring D are the same.

E34. The compound of any one of examples E1-E32, wherein Ring C and Ring D are different.

E35. The compound of any one of the preceding examples, wherein at least one of Ring C and Ring D is optionally substituted pyrrolyl.

E36. The compound of any one of examples E1-E24, wherein

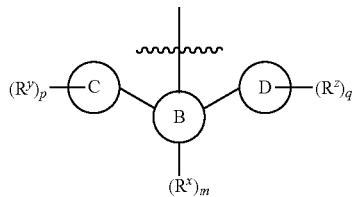

has the structure of:

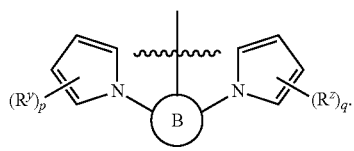

E37. The compound of example E36, wherein

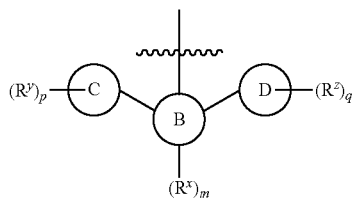

has the structure of:

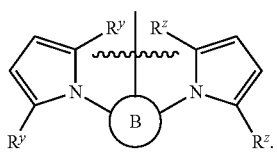

E38. The compound of any one of examples E1-E24, where p is 4.

E39a. The compound of any one of examples E1-E28, wherein q is 4.

E39b. The compound of any one of the preceding examples, wherein Ring B is optionally substituted phenyl or

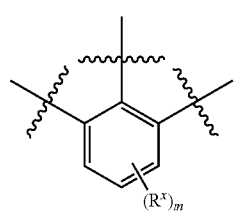

E40. The compound of any of the preceding examples, wherein Ring B is
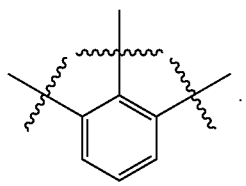 [SMILES: *c1cccc(*)c1*]
E41. The compound of example E36, wherein
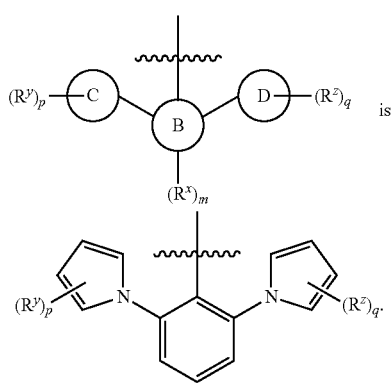
E42. The compound of example E41, wherein
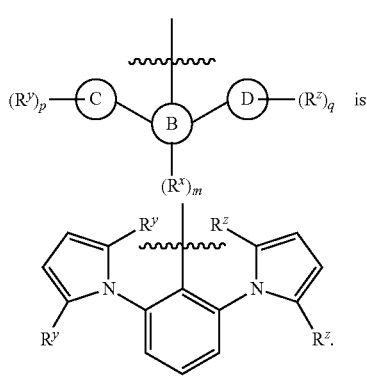
E43. The compound of example E42, wherein
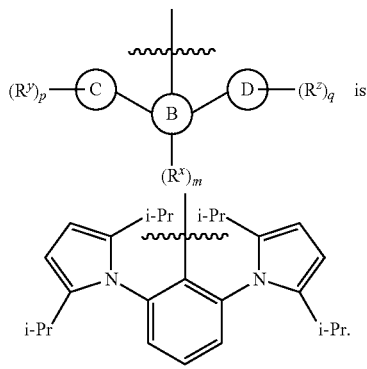
E44. The compound of example E42, wherein
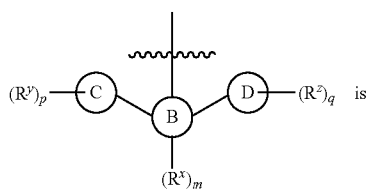
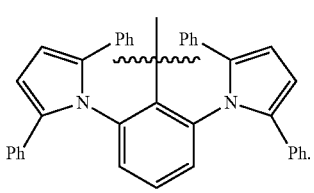
E45. The compound of example E1, wherein the compound is selected from
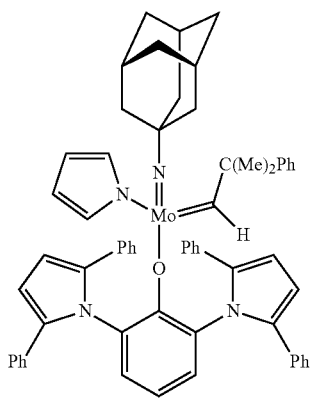
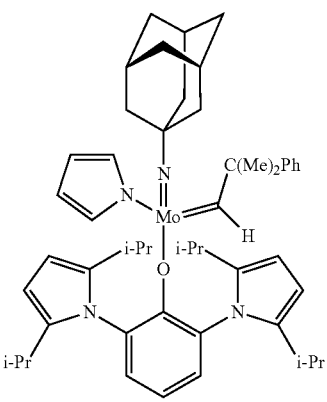

-continued

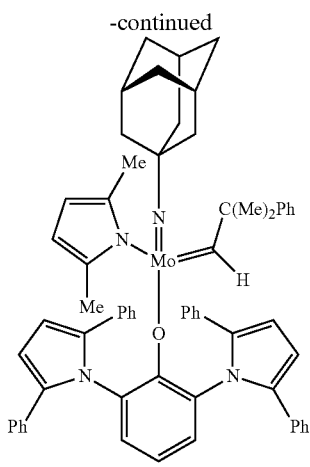

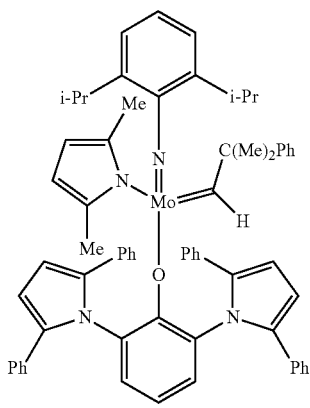

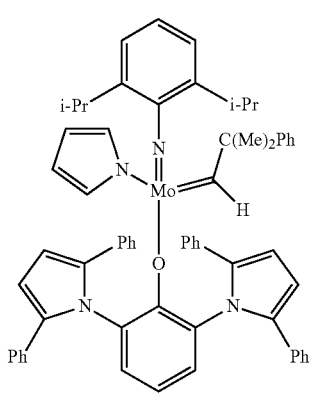

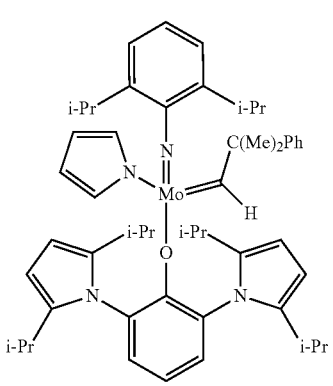

-continued

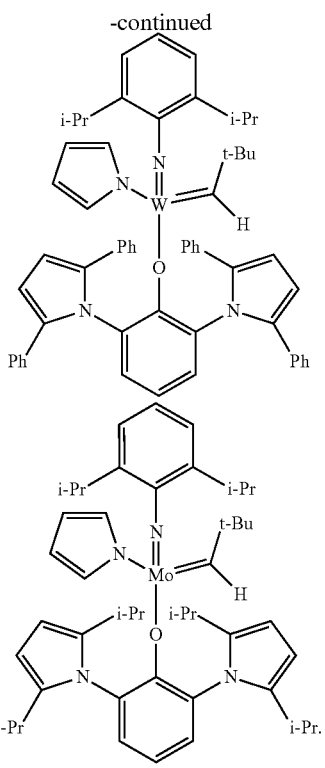

E46. The compound of example E6, wherein the compound is

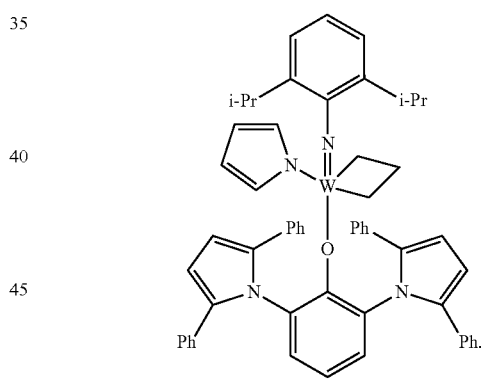

E47. A method comprising:
 (a) providing a compound of formula I or II; and
 (b) reacting a first unsaturated carbon-carbon bond and a second unsaturated carbon-carbon bond to produce a product comprising an unsaturated carbon-carbon bond.

E48. The method of example E47, wherein the compound is a compound of any one of examples E1-E23 and E25-E46.

E49. The method of example E47 or E48, wherein one of the first and the second unsaturated bonds is a carbon-carbon double bond.

E50. The method of example E47 or E48, wherein each of the first and the second unsaturated bonds is a carbon-carbon double bond, and the product comprises a carbon-carbon double bond.

E51. The method of example E47 or E48, wherein one of the first and the second unsaturated bonds is a carbon-carbon triple bond.

E52. The method of any one of examples E47-E51, wherein the product comprises an unsaturated carbon-carbon bond, wherein said unsaturated carbon-carbon bond in the product comprises one carbon atom from the first unsaturated bond and one carbon atom from the second unsaturated bond.

E53. The method of any one of examples E47-E52, wherein the product comprises a carbon-carbon double bond, and said carbon-carbon double bond is formed with Z-selectivity.

E54. The method of any one of example E47-E53, wherein the Z-selectivity is greater than about 60%.

E55. The method of example E54, wherein the Z-selectivity is greater than about 70%.

E56. The method of example E55, wherein the Z-selectivity is greater than about 80%.

E57. The method of example E56, wherein the Z-selectivity is greater than about 90%.

E58. The method of example E57, wherein the Z-selectivity is greater than about 95%.

E59. The method of any one of examples E47-E58, wherein the compound comprising the first unsaturated carbon-carbon bond and the compound comprising the second unsaturated carbon-carbon bond are identical.

E60. The compound of example E24, wherein the compound has the structure of:

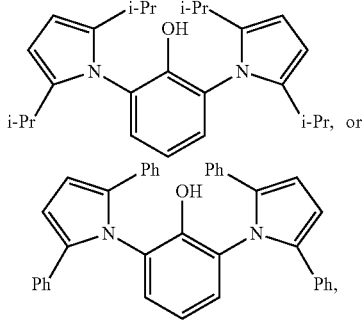

or its salt thereof.

E61. A method for preparing a metal complex, comprising the use of a compound of example E24.

E62 The method of example E61, wherein the compound of example E24 is a compound of example E60.

Conditions

In some embodiments, a ligand is provided in a molar ratio of about 10:1, 9:1, 8:1, 7:1, 6:1, 5:1, 4:1, 3:1, 2:1, or 1:1 relative to the metal. In some embodiments, a ligand is provided in a molar ratio of about 0.9:1, 0.8:1, 0.7:1, 0.6:1, 0.5:1, 0.4:1, 0.3:1, 0.2:1, or 0.1:1 relative to the metal. In certain embodiments, a ligand is provided in a molar ratio of about 1:1 relative to the metal. One of skill in the art will appreciate that the optimal molar ratio of ligand to metal will depend on, inter alia, whether the ligand is mono- or polydentate. In some embodiments, a ligand or ligand precursor having the structure of formula I is provided in a molar ratio of about 1:1 to Mo or W.

Suitable conditions for performing provided methods generally employ one or more solvents. In certain embodiments, one or more organic solvents are used. Examples of such organic solvents include, but are not limited to, hydrocarbons such as benzene, toluene, and pentane, halogenated hydrocarbons such as dichloromethane, or polar aprotic solvents, such as ethereal solvents including ether, tetrahydrofuran (THF), or dioxanes, or protic solvents, such as alcohols, or mixtures thereof. In certain embodiments, one or more solvents are deuterated.

In some embodiments, a single solvent is used. In certain embodiments, a solvent is benzene. In some embodiments, a solvent is toluene. In certain embodiments, a solvent is ether. In some embodiments, a solvent is a nitrile. In some embodiments, a solvent is acetonitrile.

In some embodiments, mixtures of two or more solvents are used, and in some cases may be preferred to a single solvent. In certain embodiments, the solvent mixture is a mixture of an ethereal solvent and a hydrocarbon. Exemplary such mixtures include, for instance, an ether/benzene mixture. Solvent mixtures may be comprised of equal volumes of each solvent or may contain one solvent in excess of the other solvent or solvents. In certain embodiments wherein a solvent mixture is comprised of two solvents, the solvents may be present in a ratio of about 20:1, about 10:1, about 9:1, about 8:1, about 7:1, about 6:1, about 5:1, about 4:1, about 3:1, about 2:1, or about 1:1. In certain embodiments wherein a solvent mixture comprises an ethereal solvent and a hydrocarbon, the solvents may be present in a ratio of about 20:1, about 10:1, about 9:1, about 8:1, about 7:1, about 6:1, about 5:1, about 4:1, about 3:1, about 2:1, or about 1:1 ethereal solvent:hydrocarbon. In certain embodiments, the solvent mixture comprises a mixture of ether and benzene in a ratio of about 5:1. One of skill in the art would appreciate that other solvent mixtures and/or ratios are contemplated herein, that the selection of such other solvent mixtures and/or ratios will depend on the solubility of species present in the reaction (e.g., substrates, additives, etc.), and that experimentation required to optimized the solvent mixture and/or ratio would be routine in the art and not undue.

Suitable conditions, in some embodiments, employ ambient temperatures. In some embodiments, a suitable temperature is about 15° C., about 20° C., about 25° C., or about 30° C. In some embodiments, a suitable temperature is from about 15° C. to about 25° C. In certain embodiments, a suitable temperature is about 20° C., 21° C., 22° C., 23° C., 24° C., or 25° C.

In certain embodiments, a provided method is performed at elevated temperature. In some embodiments, a suitable temperature is from about 25° C. to about 110° C. In certain embodiments, a suitable temperature is from about 40° C. to about 100° C., from about 50° C. to about 100° C., from about 60° C. to about 100° C., from about 70° C. to about 100° C., from about 80° C. to about 100° C., or from about 90° C. to about 100° C. In some embodiments, a suitable temperature is about 80° C. In some embodiments, a suitable temperature is about 30° C. In some embodiments, a suitable temperature is about 40° C. In some embodiments, a suitable temperature is about 50° C. In some embodiments, a suitable temperature is about 60° C. In some embodiments, a suitable temperature is about 70° C. In some embodiments, a suitable temperature is about 80° C. In some embodiments, a suitable temperature is about 90° C. In some embodiments, a suitable temperature is about 100° C. In some embodiments, a suitable temperature is about 110° C.

In certain embodiments, a provided method is performed at temperature lower than ambient temperatures. In some embodiments, a suitable temperature is from about −100° C. to about 10° C. In certain embodiments, a suitable temperature is from about −80° C. to about 0° C. In certain embodiments, a suitable temperature is from about −70° C. to about 10° C. In certain embodiments, a suitable temperature is from about −60° C. to about 10° C. In certain embodiments, a suitable temperature is from about −50° C. to about 10° C. In certain embodiments, a suitable temperature is from about −40° C. to about 10° C. In certain embodiments, a suitable temperature is or from about −30° C. to about 10° C. In some embodiments, a suitable temperature is below 0° C. In some embodiments, a suitable temperature is about −100° C. In some embodiments, a suitable temperature is about −90° C. In some embodiments, a suitable temperature is about −80° C. In some embodiments, a suitable temperature is about −70° C. In some embodiments, a suitable temperature is about −60° C. In some embodiments, a suitable temperature is about −50° C. In some embodiments, a suitable temperature is about −40° C. In some embodiments, a suitable temperature is about −30° C. In some embodiments, a suitable temperature is about −20° C. In some embodiments, a suitable temperature is about −10° C. In some embodiments, a suitable temperature is about 0° C. In some embodiments, a suitable temperature is about 10° C.

In some embodiments, a provided method is performed at different temperatures. In some embodiments, temperature changes in a provided method. In some embodiments, a provided method involves temperature increase from a lower suitable temperature to a higher suitable temperature. In some embodiments, a provided method comprises temperature increase from about −80° C., about −70° C., about −60° C., about −50° C., about −40° C., about −30° C., about −20° C., about −10° C., and about 0° C. to about 0° C., about 10° C., about 20° C., ambient temperature, about 22° C., about 25° C., about 30° C., about 40° C., about 50° C., about 60° C., about 70° C., about 80° C., about 90° C., about 100° C. and about 110° C. In some embodiments, a provided method comprises temperature increase from about −30° C. to 22° C. In some embodiments, a provided method comprises temperature decrease from a higher suitable temperature to a lower suitable temperature. In some embodiments, a provided method comprises temperature increase from about 110° C., about 100° C., about 90° C., about 80° C., about 70° C., about 60° C., about 50° C., about 40° C., about 30° C., about 25° C., about 22° C., ambient temperature, about 20° C., about 10° C., and about 0° C. to about 0° C., about −10° C., about −20° C., about −30° C., about −40° C., about −50° C., about −60° C., about −70° C., about −80° C., about −90° C., and about −100° C.

Suitable conditions typically involve reaction times of about 1 minute to about one or more days. In some embodiments, the reaction time ranges from about 0.5 hour to about 20 hours. In some embodiments, the reaction time ranges from about 0.5 hour to about 15 hours. In some embodiments, the reaction time ranges from about 1.0 hour to about 12 hours. In some embodiments, the reaction time ranges from about 1 hour to about 10 hours. In some embodiments, the reaction time ranges from about 1 hour to about 8 hours. In some embodiments, the reaction time ranges from about 1 hour to about 6 hours. In some embodiments, the reaction time ranges from about 1 hour to about 4 hours. In some embodiments, the reaction time ranges from about 1 hour to about 2 hours. In some embodiments, the reaction time ranges from about 2 hours to about 8 hours. In some embodiments, the reaction time ranges from about 2 hours to about 4 hours. In some embodiments, the reaction time ranges from about 2 hours to about 3 hours. In certain embodiments, the reaction time is about 1, 2, 3, 4, 5, 6, 7, 8, 9, 10, 11, or 12 hours. In certain embodiments, the reaction time is about 1 hour. In certain embodiments, the reaction time is about 2 hours. In certain embodiments, the reaction time is about 3 hours. In certain embodiments, the reaction time is about 4 hours. In certain embodiments, the reaction time is about 5 hours. In certain embodiments, the reaction time is about 6 hours. In certain embodiments, the reaction time is about 12 hours. In certain embodiments, the reaction time is less than about 1 hour. In certain embodiments, the reaction time is about 5, 10, 15, 20, 25, 30, 35, 40, 45, 50, or 55 minutes. In some embodiments, the reaction time is about 5 minutes. In some embodiments, the reaction time is about 10 minutes. In some embodiments, the reaction time is about 15 minutes. In some embodiments, the reaction time is about 20 minutes. In some embodiments, the reaction time is about 25 minutes. In some embodiments, the reaction time is about 30 minutes. In some embodiments, the reaction time is about 35 minutes. In some embodiments, the reaction time is about 40 minutes. In some embodiments, the reaction time is about 100 minutes. In some embodiments, the reaction time is about 110 minutes. In some embodiments, the reaction time is about 200 minutes. In some embodiments, the reaction time is about 300 minutes. In some embodiments, the reaction time is about 400 minutes.

Some embodiments may provide the ability to selectively synthesize, via a metathesis reaction, products having a Z or E configuration about a double bond. In some embodiments, a method of the present invention provides the ability to synthesize compounds comprising a Z-olefin. In some embodiments, such methods are useful when applied to a wide range of olefin substrates, including those having sterically small or large groups adjacent the olefin. In some embodiments, the substrate olefins are terminal olefins.

In some embodiments, the present invention provides a method for Z-selective metathesis reactions. In some embodiments, a provided method produces a double bond in a Z:E ratio greater than about 1:1, greater than about 2:1, greater than about 3:1, greater than about 4:1, greater than about 5:1, greater than about 6:1, greater than about 7:1, greater than about 8:1, greater than about 9:1, greater than about 95:5, greater than about 96:4, greater than about 97:3, greater than about 98:2, or, in some cases, greater than about 99:1, as determined using methods described herein (e.g., HPLC or NMR). In some cases, about 100% of the double bond produced in the metathesis reaction may have a Z configuration. The Z or cis selectivity may also be expressed as a percentage of product formed. In some cases, the product may be greater than about 50% Z, greater than about 60% Z, greater than about 70% Z, greater than about 80% Z, greater than about 90% Z, greater than about 95% Z, greater than about 96% Z, greater than about 97% Z, greater than about 98% Z, greater than about 99% Z, or, in some cases, greater than about 99.5% Z.

In some embodiments, a provided compound isomerizes a product. In some embodiments, a provided compound isomerizes a Z product. In some embodiments, a provided compound isomerizes a Z product slower than the formation of the product. In some embodiments, a provided compound isomerizes an E product. In some embodiments, a provided compound isomerizes an E product slower than the formation of the product.

In some embodiments, a provided compound does not isomerize a product. In some embodiments, a provided compound does not isomerize a Z product. In some embodiments, a provided compound does not isomerize an E product.

In some embodiments, a provided metal complex compound, e.g. a compound of formula I or II, or an active catalyst formed from a provided compound, is stable under metathesis conditions. In some embodiments, a provided compound, or an active catalyst formed from a provided compound, decomposes under metathesis conditions. In some embodiments, a provided compound, or an active catalyst formed from a provided compound, decomposes under metathesis conditions within about 1 hour. In some embodiments, a provided compound, or an active catalyst formed from a provided compound, decomposes under metathesis conditions within about 2 hours. In some embodiments, a provided compound, or an active catalyst formed from a provided compound, decomposes under metathesis conditions within about 6 hours. In some embodiments, a provided compound, or an active catalyst formed from a provided compound, decomposes under metathesis conditions within about 12 hours. In some embodiments, a provided compound, or an active catalyst formed from a provided compound, decomposes under metathesis conditions within about 24 hours. In some embodiments, a provided compound, or an active catalyst formed from a provided compound, decomposes under metathesis conditions within about 48 hours. In some embodiments, a provided compound, or an active catalyst formed from a provided compound, decomposes under metathesis conditions within about 96 hours.

In some embodiments, a provided compound, or an active catalyst formed from a provided compound, decomposes prior to isomerization of a product. In some embodiments, a provided compound, or an active catalyst formed from a provided compound, partially decomposes prior to isomerization of a product. In some embodiments, a provided compound, or an active catalyst formed from a provided compound, decomposes prior to isomerization of a Z product. In some embodiments, a provided compound, or an active catalyst formed from a provided compound, partially decomposes prior to isomerization of a Z product. In some embodiments, a provided compound, or an active catalyst formed from a provided compound, decomposes prior to isomerization of an E product. In some embodiments, a provided compound, or an active catalyst formed from a provided compound, partially decomposes prior to isomerization of an E product.

In some embodiments, a metathesis reaction using a compound of the present invention produces a polymer wherein the polymer is >50% cis, >50% syndiotactic. In some embodiments, a metathesis reaction using a compound of the present invention produces a polymer wherein the polymer is >60% cis, >60% syndiotactic. In some embodiments, a metathesis reaction using a compound of the present invention produces a polymer wherein the polymer is >70% cis, >70% syndiotactic. In some embodiments, a metathesis reaction using a compound of the present invention produces a polymer wherein the polymer is 80% cis, >80% syndiotactic. In some embodiments, a metathesis reaction using a compound of the present invention produces a polymer wherein the polymer is >90% cis, 90% syndiotactic. In some embodiments, a metathesis reaction using a compound of the present invention produces a polymer wherein the polymer is >95% cis, 90% syndiotactic. In some embodiments, a metathesis reaction using a compound of the present invention produces a polymer wherein the polymer is >99% cis, 90% syndiotactic. In some embodiments, a metathesis reaction using a compound of the present invention produces a polymer wherein the polymer is >90% cis, >95% syndiotactic. In some embodiments, a metathesis reaction using a compound of the present invention produces a polymer wherein the polymer is >95% cis, >95% syndiotactic. In some embodiments, a metathesis reaction using a compound of the present invention produces a polymer wherein the polymer is >99% cis, >90% syndiotactic. In some embodiments, a metathesis reaction using a compound of the present invention produces a polymer wherein the polymer is >99% cis, >95% syndiotactic. In some embodiments, a metathesis reaction using a compound of the present invention produces a polymer wherein the polymer is >99% cis, >97% syndiotactic. In some embodiments, a metathesis reaction using a compound of the present invention produces a polymer wherein the polymer is >99% cis, >99% syndiotactic.

In some embodiments, a provided method requires an amount of a provided compound (e.g., a metal complex having the structure of formula I or II) such that the loading is from about 0.01 mol % to about 20 mol % of the provided compound relative to substrate (e.g., a first or second double bond). In certain embodiments, a provided compound is used in an amount of between about 0.01 mol % to about 10 mol %. In certain embodiments, a provided compound is used in an amount of between about 0.01 mol % to about 6 mol %. In certain embodiments, a provided compound is used in an amount of between about 0.01 mol % to about 5 mol %. In certain embodiments, a provided compound is used in an amount of between about 0.01 mol % to about 4 mol %. In certain embodiments, a provided compound is used in an amount of between about 0.01 mol % to about 3 mol %. In certain embodiments, a provided compound is used in an amount of between about 0.01 mol % to about 1 mol %. In certain embodiments, a provided compound is used in an amount of between about 0.01 mol % to about 0.5 mol %. In certain embodiments, a provided compound is used in an amount of between about 0.01 mol % to about 0.2 mol %. In certain embodiments, a provided compound is used in an amount of about 0.05%, 0.1%, 0.2%, 0.5%, 1%, 2%, 3 mol %, 4 mol %, 5 mol %, 6 mol %, 7 mol %, 8 mol %, 9 mol %, or 10 mol %.

In some embodiments, a method of the present invention requires an amount of solvent such that the concentration of the reaction is between about 0.01 M and about 1 M. In some embodiments, the concentration of the reaction is between about 0.01 M and about 0.5 M. In some embodiments, the concentration of the reaction is between about 0.01 M and about 0.1 M. In some embodiments, the concentration of the reaction is between about 0.01 M and about 0.05 M. In some embodiments, the concentration of the reaction is about 0.01 M. In some embodiments, the concentration of the reaction is about 0.02 M. In some embodiments, the concentration of the reaction is about 0.03 M. In some embodiments, the concentration of the reaction is about 0.04 M. In some embodiments, the concentration of the reaction is about 0.05 M. In some embodiments, the concentration of the reaction is about 0.1 M. In some embodiments, the concentration of the reaction is about 0.3 M.

In some embodiments, a method of the present invention is performed at ambient pressure. In some embodiments, a method of the present invention is performed at reduced pressure. In some embodiments, a method of the present invention is performed at a pressure of less than about 20 torr. In some embodiments, a method of the present invention is performed at a pressure of less than about 15 torr. In some embodiments, a method of the present invention is performed at a pressure of less than about 10 torr. In some embodiments, a method of the present invention is performed at a pressure of about 9, 8, 7, 6, 5, 4, 3, 2, or 1 torr. In certain embodiments, a method of the present invention is performed at a pressure of about 7 torr. In certain embodiments, a method of the present invention is performed at a pressure of about 1 torr. In some embodiments, a method of the present invention is performed at increase pressure. In some embodiments, a method of the present invention is performed at greater than about 1 atm. In some embodiments, a method of the present invention is performed at greater than about 2 atm. In some embodiments, a method of the present invention is performed at greater than about 3 atm. In some embodiments, a method of the present invention is performed at greater than about 5 atm. In some embodiments, a method of the present invention is performed at greater than about 10 atm. In some embodiments, a method of the present invention is performed at about 2 atm. In some embodiments, a method of the present invention is performed at about 3 atm. In some embodiments, a method of the present invention is performed at about 5 atm. In some embodiments, a method of the present invention is performed at about 10 atm.

In some embodiments, a method of the present invention is performed at increased pressure. In some embodiments, a method of the present invention is performed at greater than about 1 atm. In some embodiments, a method of the present invention is performed at greater than about 2 atm. In some embodiments, a method of the present invention is performed at greater than about 3 atm. In some embodiments, a method of the present invention is performed at greater than about 5 atm. In some embodiments, a method of the present invention is performed at greater than about 10 atm. In some embodiments, a method of the present invention is performed at about 2 atm. In some embodiments, a method of the present invention is performed at about 3 atm. In some embodiments, a method of the present invention is performed at about 5 atm. In some embodiments, a method of the present invention is performed at about 10 atm.

As mentioned above, provided compounds are useful for metathesis reactions. Exemplary such methods and reactions are described below.

It will be appreciated that, in certain embodiments, each variable recited for the above method is as defined above and described in embodiments, herein, singly and in combination.

EXEMPLIFICATION

The present invention recognizes, among other things, that there is a continuing demand for sterically demanding ligands for metathesis catalysts. In some embodiments, the present invention provides new compounds that can be used as ligand precursors to prepare metal complexes that promote highly efficient and Z-selective metathesis reactions. In some embodiments, the present invention provides new metal complexes that promote highly efficient and Z-selective metathesis reactions. In some embodiments, the present invention provides methods for preforming highly efficient and Z-selective metathesis reactions. Exemplary but non-limiting examples are depicted herein. In some embodiments, the present invention provides metal complexes that contain O-2,6-(2,5-R$_2$Pyrrolyl)$_2$C$_6$H$_3$ (2,6-DiPyrrolylPhenoxide or ODPP$^R$) ligands. In some embodiments, R=i-Pr or Ph.

2-Methoxy-1,3-diaminobenzene was prepared from 2-bromo-1,3-dinitrobenzene as shown in equation 1. The pyrrolyl groups were then constructed employing the desired γ-diketone in a Paal-Knorr condensation followed by deprotection with BBr$_3$. Both DPP$^{Ph}$OH and DPP$^{iPr}$OH were purified employing column chromatography and recrystallized from hexane (DPP$^{iPr}$OH) or isopropanol.

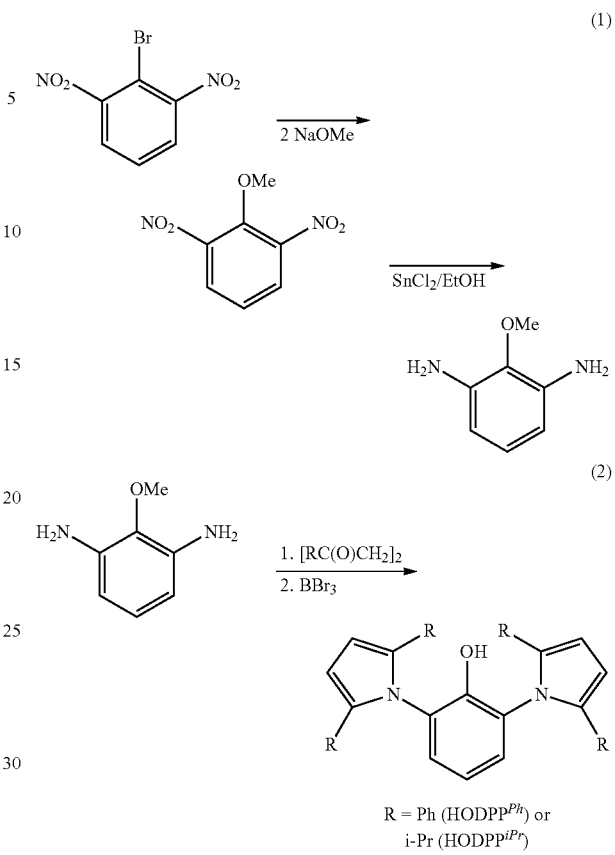

Addition of one equivalent of DPP$^{Ph}$OH or DPP$^{iPr}$OH to Mo(NAd)(CHCMe$_2$Ph)(Pyr)$_2$, Mo(NAd)(CHCMe$_2$Ph)(Me$_2$Pyr)$_2$, Mo(NAr)(CHCMe$_2$Ph)(Pyr)$_2$ and Mo(NAr)(CHCMe$_2$Ph)(Me$_2$Pyr)$_2$ (Ad=1-adamantyl, Ar=2,6-i-Pr$_2$C$_6$H$_3$, Pyr=pyrrolide; Me$_2$Pyr=2,5-dimethylpyrrolide) produced MAP complexes 1a, 1b, 2a, 2b, 3a, and 3b (Hock, A. S.; Schrock, R. R.; Hoveyda, A. H. *J. Am. Chem Soc.* 2006, 128, 16373).

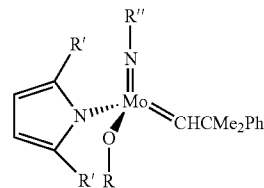

1a; R'' = Ad, R' = H, OR = ODPP$^{Ph}$
1b; R'' = Ad, R' = H, OR = ODPP$^{iPr}$
2a; R'' = Ad, R' = Me, OR = ODPP$^{Ph}$
2b; R'' = Ar, R' = H, OR = ODPP$^{Ph}$
3a; R'' = Ar, R' = H, OR = ODPP$^{Ph}$
3b; R'' = Ar, R' = H, OR = ODPP$^{iPr}$

The reaction to give 1a required heating the mixture for one hour at 80° C., whereas the reaction to give 1b was complete at 22° C. (~20 mM) within four hours. For steric reasons, the reactions to give 2a and 2b were slower than those that yielded 1a and 1b. It should be noted, for comparison, that both Mo(NAd)(CHCMe$_2$Ph)(Pyr)(OHIPT)$^{5a}$ and Mo(NAr)(CHCMe$_2$Ph)(Pyr)(OHIPT)$^9$ have been prepared (the latter in situ) from Mo(NR)(CHCMe$_2$Ph)

(Pyr)$_2$ (R=Ad or Ar) and one equivalent of HIPTOH. Therefore, ODPP$^{Ph}$ and ODPP$^{iPr}$ appear to behave approximately like the OHIPT ligand, at least in terms of the synthesis of MAP species through protonation of bispyrrolides.

Figure 2:
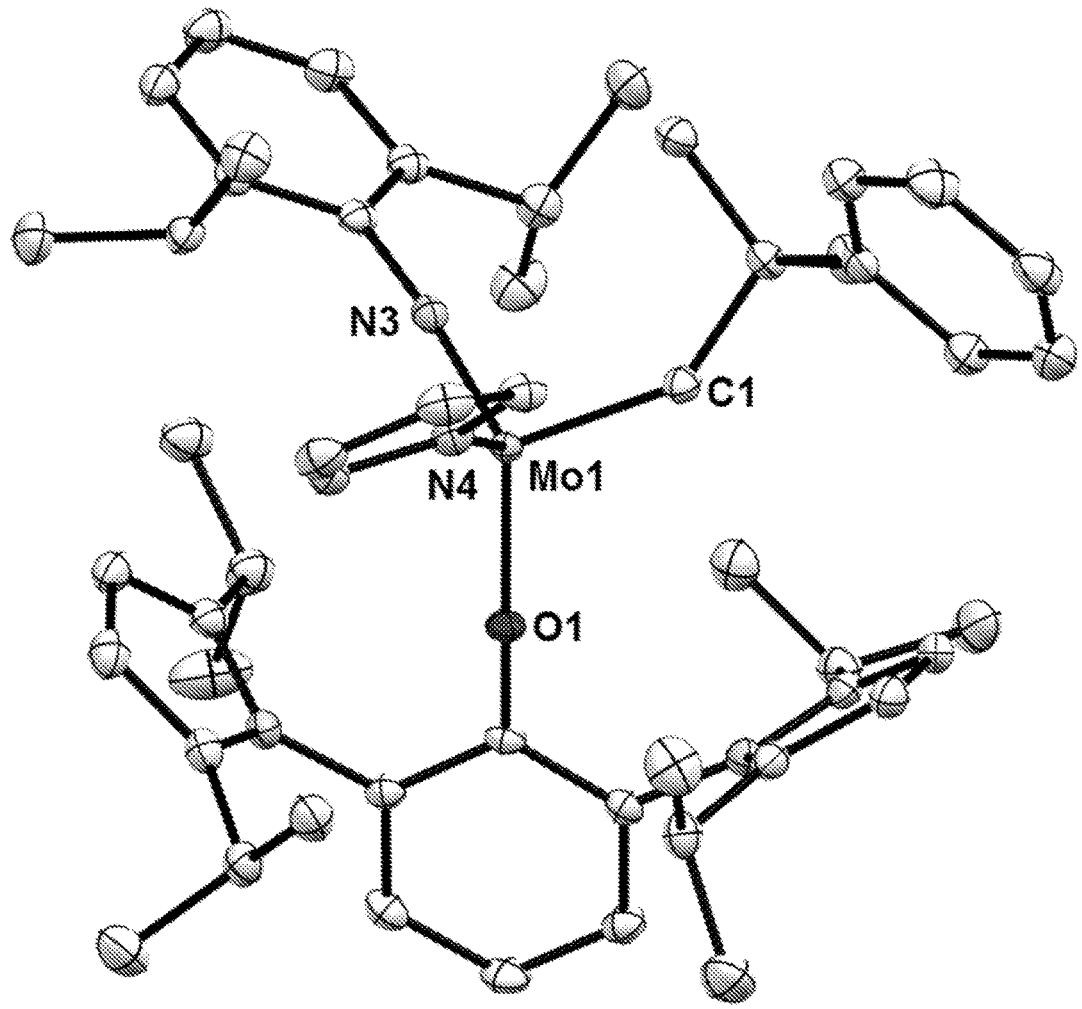
FIG. 2. Thermal ellipsoid representation of the structure of 3b at the 50% probability level. The solvent molecule and hydrogen atoms were omitted for clarity.

The X-ray structure of Mo(NAr)(CHCMe$_2$Ph)(Me$_2$Pyr)(ODPP$^{Ph}$) (2b) is shown in FIG. 1. The dihedral angles between the phenyl ring in ODPP$^{Ph}$ and the pyrrolyl rings are 83.7(3)° (C41-C42-N3-C47) and 68.7(3)° (C41-C46-N4-C67). In the structure of Mo(NAr)(CHCMe$_2$Ph)(Pyr)(ODPP$^{iPr}$) (3b) (FIG. 2) the dihedral angles between the phenyl ring in ODPP$^{iPr}$ and the pyrrolyl rings are 70.3(2)° (C21-C22-N1-C30) and 80.8(2)° (C21-C26-N2-C37). The Mo—O—C angle is larger in 3b)(167.42(9)°) than in 2b) (153.7(1)°), consistent with the greater steric demand of the ODPP$^{iPr}$ ligand system than the ODPP$^{Ph}$ ligand system. Other bond distances and angles in the two structures can be found below.

The reaction between W(NAr)(CH-t-Bu)(Pyr)$_2$(dme) and one equivalent of DPP$^{Ph}$OH led to W(NAr)(CH-t-Bu)(Pyr)(ODPP$^{Ph}$) (4a). The reaction was performed in a sonicator bath due to the limited solubility of DPP$^{Ph}$OH in C$_6$H$_6$. Since DPP$^{iPr}$OH is more soluble in benzene than DPP$^{Ph}$OH in benzene, sonication was not required for the synthesis of W(NAr)(CH-t-Bu)(Pyr)(ODPP$^{iPr}$) (4b).

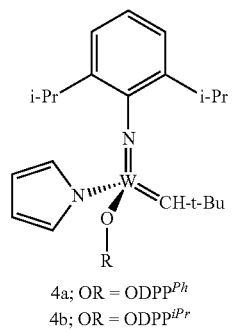

4a; OR = ODPP$^{Ph}$
4b; OR = ODPP$^{iPr}$

Figure 3:
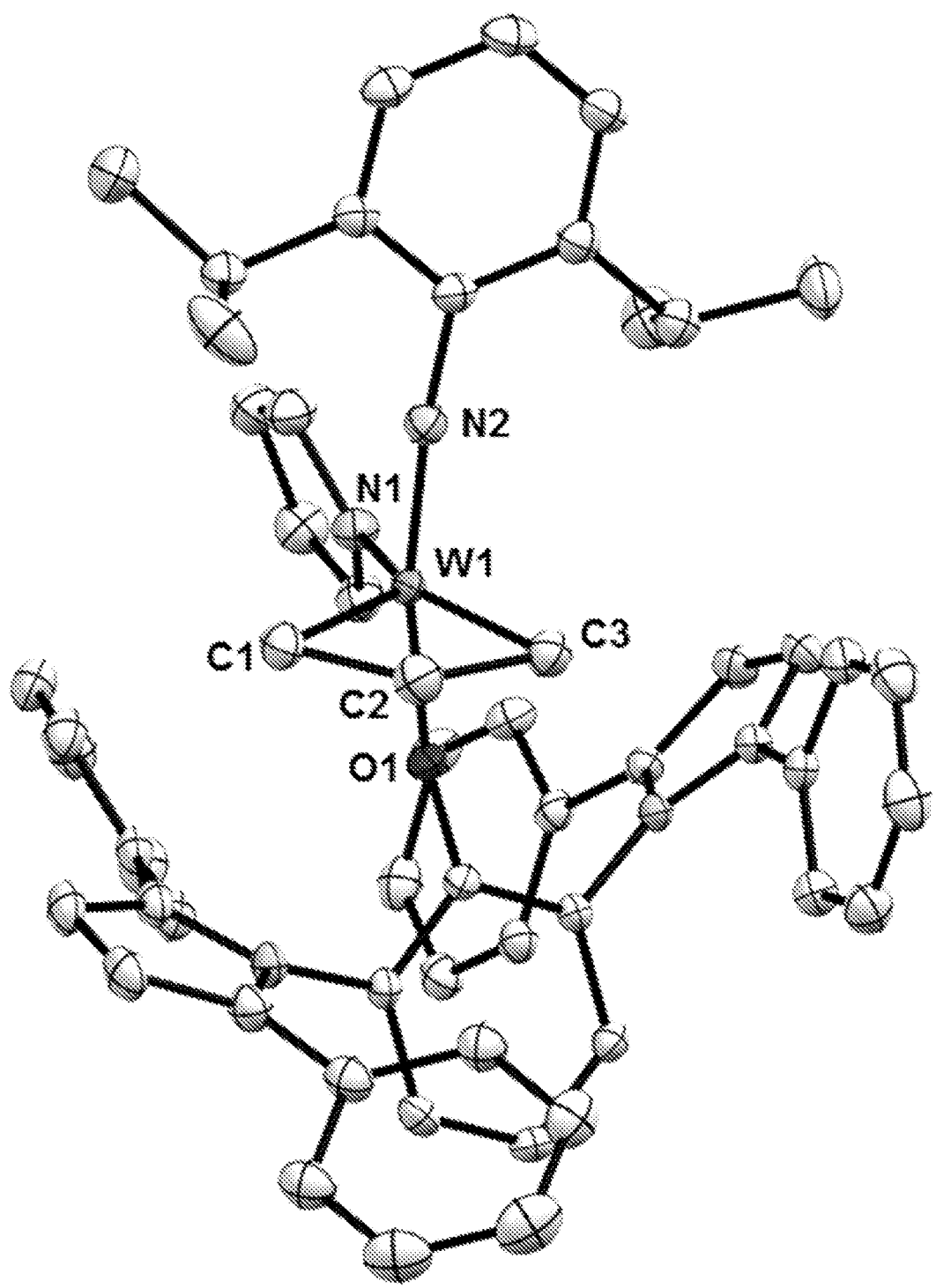
FIG. 3. Thermal ellipsoid representation of the structure of 5 at the 50% probability level. The minor component of the tungsten disorder and the hydrogen atoms are omitted for clarity. Selected bond lengths (Å) and angles (°): W(1)-O(1) 1.986(2), W(1)-N(1) 2.031(1), W(1)-N(2) 1.752(2), W(1)-C(1) 2.035(2), W(1)-C(3) 2.083(2), W . . . C2 2.370(2), C(1)-C(2) 1.603(3), C(2)-C(3) 1.590(3); O(1)-W(1)-N(1) 84.03(7), N(2)-W(1)-O(1) 166.13(7), N(2)-W(1)-C(3) 93.16(9), N(2)-W(1)-C(1) 97.96(9), N(1)-W(1)-C(2) 165.65(8), W(1)-C(3)-C(2) 79.1(1), C(3)-C(2)-C(1) 117.5(2), C(2)-C(1)-W(1) 80.3(1), C(1)-W(1)-C(3) 83.02(9), N(1)-W(1)-N(2) 91.27(8), N(1)-W(1)-C(3) 150.64(8).
Figure 4:
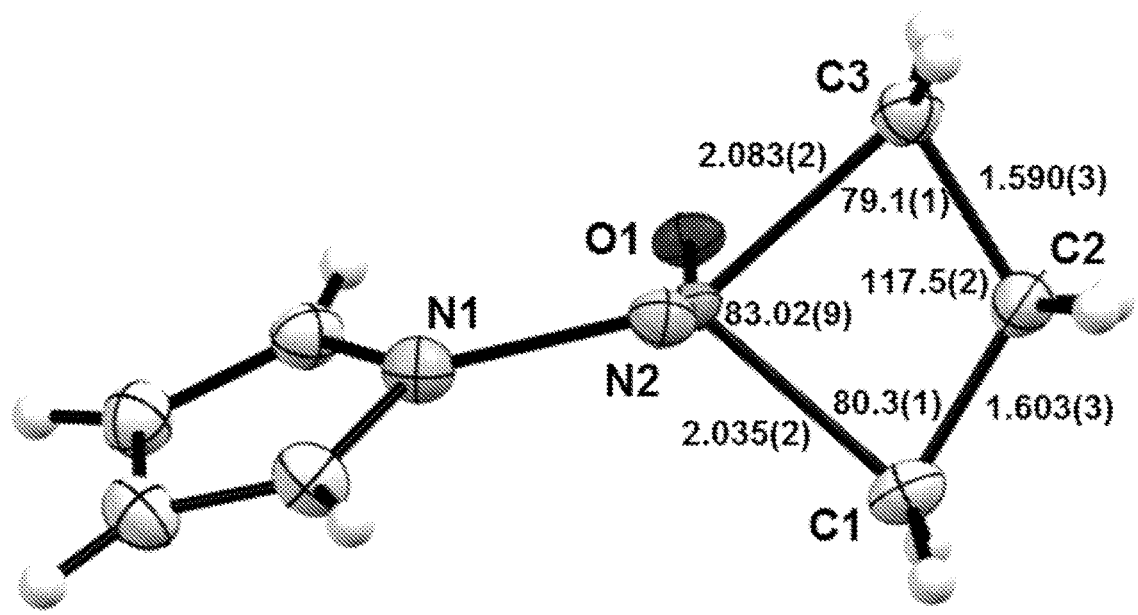
FIG. 4. Thermal ellipsoid drawing (50%) of metallacyclobutane moiety in 5 with bond lengths (Å) and angles (°).

Compound 4a reacts readily with ethylene to yield a metallacyclobutane complex, W(NAr)(C$_3$H$_6$)(Pyr)(ODPP$^{Ph}$) (5). Without the intention to be limited by theory, according to proton and carbon NMR data 5 has a TBP geometry. However, the structure of 5 in the solid state (FIG. 3) is closer to a square pyramidal structure, according to the τ value (0.26), which for a SP is 0 and for a perfect TBP is 1 (Addison, A. W.; Rao, T. J.; Reedijk, J.; van Rijn, J.; Verschoor, G. C. J. Chem. Soc., Dalton Trans. 1984, 1349). The metallacyclobutane carbon atom in approximately the apical position (W–C1=2.035(2) Å) is closer to the metal than is the carbon atom in the basal position (W–C2=2.083(2) Å) by a statistically significant amount (FIG. 4). The C$_\alpha$-C$_\beta$ bond lengths (1.590(3) and 1.603(3)) are (barely) statistically different and in the direction that, without the intention to be limited by theory, implies an ethylene that contains C2 and C3 is approaching or leaving the CNO face of W(NAr)(CH$_2$)(Pyr)(ODPP$^{Ph}$) approximately trans to the pyrrolide (FIG. 4). The W—C(2) distance is 2.370(2), which is 0.1-0.2 Å longer than a typical W—C single bond. Since the structure of 5 is different from a square pyramidal complex (SP in FIG. 5) in which the imido group is in the apical position and the metallacyclic ring in basal positions, another type that has been observed in the solid state and in solution (Yuan, J.; Townsend, E. M.; Schrock, R. R.; Goldman, A. S.; Müller, P.; Takase, M. Adv. Syn. Catal. 2011, 353, 1985), we will call the structure of 5 an SP' metallacyclobutane structure.

Figure 5:
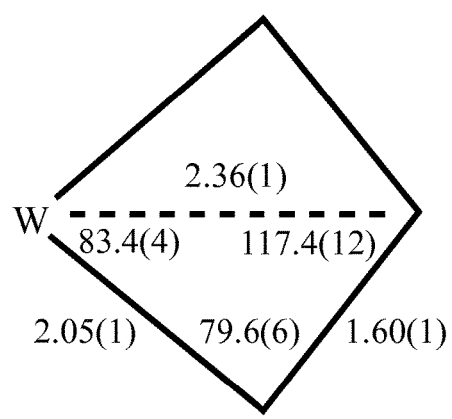
FIG. 5. Selected distances and angles in five TBP structures (Avg) and one SP structure.
Figure 5:
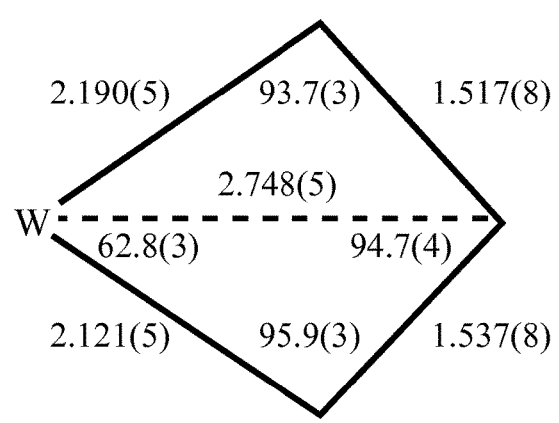

Selected distances and angles (averages) in the structures of five unsubstituted tungstacyclobutane TBP complexes (Flook, M. M.; Jiang, A. J.; Schrock, R. R.; Müller, P.; Hoveyda, A. H. J. Am. Chem. Soc. 2009, 131, 7962; Marinescu, S. C.; Schrock, R. R.; Müller, P.; Takase, M. K.; Hoveyda, A. H. Organometallics 2011, 30, 1780; and Jiang, A. J.; Simpson, J. H.; Müller, P.; Schrock, R. R. J. Am. Chem. Soc. 2009, 131, 7770), which have τ values from 0.47 to 0.68, including both complexes in the asymmetric unit of the structure of W(NAr)(C$_3$H$_6$)(MePyr)(OBr$_2$Bitet) (Jiang, A. J.; Simpson, J. H.; Müller, P.; Schrock, R. R. J. Am. Chem. Soc. 2009, 131, 7770), and the one β substituted SP structure (W(NAr)[CH$_2$CH(Ph)CH$_2$](Pyr)(OHIPTNMe$_2$) (Yuan, J.; Townsend, E. M.; Schrock, R. R.; Goldman, A. S.; Müller, P.; Takase, M. Adv. Syn. Catal. 2011, 353, 1985), in which τ=0.06) are shown in FIG. 5. The TBP and SP' structures are closer to the transition state for olefin loss from the metallacyclobutane ring than is the SP structure, and the SP' structure is the closest. Without the intention to be limited by theory, τ values for the TBP metallacyclobutane complexes are unlikely to approach 1 as a consequence of the constraints inherent in a complex that contains a metallacylobutane ring in the equatorial position; the maximum is ~0.68.

While not wishing to be limited by theory, the findings here are consistent with those concerning metallacyclobutanes made from MAP alkylidenes ((a) Solans-Monfort, X.; Clot, E.; Coperet, C.; Eisenstein, O. J. Am. Chem. Soc. 2005, 127, 14015; (b) Poater, A.; Solans-Monfort, X.; Clot, E.; Coperet, C.; Eisenstein, O. J. Am. Chem. Soc. 2007, 129, 8207; (c) Solans-Monfort, X.; Coperet, C.; Eisenstein, O. J. Am. Chem. Soc. 2010, 132, 7750; (d) Solans-Monfort, X.; Coperet, C.; Eisenstein, O. Organometallics 2012, 31, 6812). The olefin approaches the more "open" CNO (imido/alkylidene/OR) face "trans" to the pyrrolide to yield a square pyramidal metallacyclobutane in which the ring spans apical and basal sites, a structure that is essentially that found here. The structure becomes a TBP when the O-M-N$_{imido}$ angle opens to ~180° and the pyrrolide moves into an equatorial position where the N2-M-C3 and N2-M-C1 angles are equal. A continuation of the movement of N2, N1, and O leads to another SP' structure in which the metallacyclobutane again spans apical (now C3) and basal (now C1) sites and the ethylene that is leaving the coordination sphere contains C1 and C2. Both experimentally and theoretically the barrier for interconversion of TBP and SP forms in general is relatively low (For relatively recent studies see (a) Moberg, C. Angew. Chem. Int. Ed. 2011, 50, 10290. (b) Couzijn, E. P. A.; Slootweg, J. C.; Ehlers, A. W.; Lammertsma, K. J. Am. Chem. Soc. 2010, 132, 18127). The energy barrier for interconversion of TBP and SP' metallacyclobutane structures seems likely to be significantly even lower since minimal movement of the imido and aryloxide ligands is required.

Regarding why the structure of 5 is SP' instead of TBP, without the intention to be limited by theory, we reason that the energy difference between the two could be so low that intramolecular steric forces and/or packing forces in the crystal tip the balance in favor of SP'. In some embodiments, evidence consists of a loss of mirror symmetry in the metallacylobutane ring at low temperatures.

The ROMP polymerization of 50 equivalents of 5, 6-dicarbomethoxynorbornadiene was chosen as an initial measure of the stereoselectivity of the six MAP catalysts described earlier. Although the rates of the polymerizations varied in terms of steric hindrance around the metal, all polymers were found to have a >99% cis, syndiotactic structure.

Compounds 4a and 4b are highly active for the homo-coupling of 1-octene (Table 1). For comparison, W(NAr)(C$_3$H$_6$)(pyr)(OHIPT) (6) was tested under identical conditions. Both compounds 4a and 4b provide a significantly faster rate than 6. Catalyst 4a provided 62% conversion and >95% Z-selectivity in 10 minutes. Catalyst 4b provided 83% conversion over 400 minutes with >95% Z-selectivity.

TABLE 1

Homocoupling of 1-octene with 4a and 4b.a

| Catalyst | t (min) | % Conv | % Z |
|---|---|---|---|
| 4a | 10 | 62 | >95 |
| 4a | 40 | 72 | 90 |
| 4a | 110 | 88 | 84 |
| 4a | 400 | >95 | 62 |
| 4b | 10 | 24 | — |
| 4b | 40 | 36 | — |
| 4b | 110 | 59 | >95 |
| 4b | 400 | 83 | 94 |
| 6 | 10 | 5 | — |
| 6 | 40 | 16 | — |
| 6 | 110 | 46 | >95 |
| 6 | 400 | 93 | >95 | aConditions: 25° C., 4 mol % catalyst loading, 0.3M in C$_6$H$_6$.

General Procedures. All manipulations were conducted under a nitrogen atmosphere in a Vacuum Atmospheres drybox or using Schlenk techniques unless otherwise specified. All glassware was oven-dried prior to use. Ether, pentane, toluene, and benzene were degassed with dinitrogen and passed through activated alumina columns under nitrogen. All dried and deoxygenated solvents were stored over molecular sieves in a nitrogen-filled glovebox. NMR spectra were recorded on a Bruker or Varian 300 MHz, 400 MHz, 500 MHz or 600 MHz spectrometer at room temperature unless otherwise specified. Chemical shifts for $^1$H spectra were referenced to the residual resonances of the deuterated solvent and are reported as parts per million relative to tetramethylsilane. 2-Bromo-1,3-dinitrobenzene (Sienkowska, M.; Benin, V.; Kaszynski, P. *Tetrahedron* 2000, 56, 165), 2,7-dimethyloctane-3,6-dione (Ito, Y.; Konoike, T.; Saegusa, T. *J. Am. Chem. Soc.,* 1975, 97, 2912), Mo(NAd)(CHCMe$_2$Ph)(Pyr)$_2$ (Hock, A. S.; Schrock, R. R.; Hoveyda, A. H. *J. Am. Chem Soc.* 2006, 128, 16373), W(NAr)(CH-t-Bu)(Pyr)$_2$(dme) (Kreickmann, T.; Arndt, S.; Schrock, R. R.; Mueller, P. *Organometallics* 2007, 26, 5702) and DCMNBD (Tabor, D. C.; White, F. H.; Collier, L. W.; Evans, S. A. *J. Org Chem.* 1983, 48, 1638) were prepared according to the literature. Analytical data were obtained from the CENTC Elemental Analysis Facility at the University of Rochester, funded by NSF CHE-0650456, or by Midwest Microlabs, Indianapolis, Ind.

2-methoxy-1,3-dinitrobenzene: An argon filled Schlenk flask was charged with 25.77 g (104 mmol) of 2-bromo-1,3-dinitrobenzene, 150 mL of absolute methanol was added and the reaction mixture was chilled in an ice bath. 2.4 g (104 mmol) of Na was added, and the resulting reaction mixture was purged with argon until all Na was dissolved and stirred at RT over night. The solvent was removed, the residue was re-suspended in acetone and filtered through Celite to remove NaBr. The solvent was removed, and the crude product was recrystallized from iPrOH. Yield: 19.8 g (90%). $^1$H NMR (CDCl$_3$): δ 8.05 (d, J$_{HH}$=8.2 Hz, 2H, Ar), 7.38 (t, J$_{HH}$=8.2 Hz, 1H, Ar), 4.07 (s, 3H, OCH$_3$) ppm.

2-methoxybenzene-1,3-diamine: A 2 L round bottomed flask was charged with 23 g (116 mmol) 2-methoxy-1,3-dinitrobenzene and 261 g (1.16 mol) tin chloride dihydrate. 160 mL EtOH was added, and the resulting suspension was stirred at 70° C. for 90 min. In the beginning, the reaction is very exothermic be careful! The solvent was removed and the reaction mixture was diluted with H$_2$O and slowly added to about 500 mL of a 10 M NaOH solution. The suspension was cooled down to RT and extracted three times with EtOAc. The combined organic layers were dried over MgSO$_4$, filtered and the solvent was removed under reduced pressure. The product was obtained as red oil and used without further purification. Yield: 13 g (81%). $^1$H NMR (CDCl$_3$): δ 6.73 (t, J$_{HH}$=7.8 Hz, 1H, Ar), 6.18 (d, J$_{HH}$=7.8 Hz, 2H, Ar), 3.77 (s, 3H, OCH$_3$), 3.75 (bs, 4H, NH$_2$) ppm.

1,1'-(2-methoxy-1,3-phenylene)bis(2,5-diisopropylpyrrolyl): A mixture of 2-methoxybenzene-1,3-diamine (8.5 g, 61.5 mmol), 2,7-dimethyloctane-3,6-dione (23 g, 135 mmol), p-toluenesulfonic acid monohydrate (40 mg, 0.21 mmol) and 120 mL toluene was refluxed in a Dean-Stark apparatus for 24 h. The solution was filtered through silica gel, and the solvent was removed under reduced pressure. The pure product was obtained after column chromatography and (LM: toluene) recrystallization from iPrOH. Yield: 13.5 g (54%). $^1$H NMR (CDCl$_3$): δ7.31 (d, J$_{HH}$=7.7 Hz, 2H, Ar), 7.18 (t, J$_{HH}$=7.7 Hz, 1H, Ar), 5.99 (s, 4H, Pyr), 3.08 (s, 3H, OCH$_3$), 2.61 (sep, J$_{HH}$=6.6 Hz, 4H, CHMe$_2$), 1.10 (t, J$_{HH}$=6.6 Hz, 24H, CH(CH$_3$)$_2$) ppm.

1,1'-(2-methoxy-1,3-phenylene)bis(2,5-diphenylpyrrolyl): The reaction was performed in the same manner as 1,1'-(2-methoxy-1,3-phenylene)bis(2,5-diisopropylpyrrolyl). The pure product was obtained after column chromatography and (LM: toluene) recrystallization from iPrOH/acetone. Yield: 4.8 g (61%). $^1$H NMR (CDCl$_3$): δ 7.18 (m, 12H, Ph), 7.10 (d, J$_{HH}$=7.8 Hz, 2H, Ar), 7.00 (m, 8H, Ph), 6.88 (t, J$_{HH}$=7.8 Hz, 1H, Ar), 6.40 (s, 4H, Pyr), 2.45 (s, 3H, OCH$_3$) ppm.

2,6-bis(2,5-diisopropylpyrrolyl)phenol (DPP$^{iPr}$OH): In a dry box a 250 mL Schlenk flask was charged with 13.1 g (32 mmol) 1,1'-(2-methoxy-1,3-phenylene)bis(2,5-diisopropylpyrrolyl) and 150 mL CH$_2$Cl$_2$. 18.3 mL (193 mmol) BBr$_3$ was added and the resulting solution was stirred for 14 h at 55° C., chilled with and ice bath and quenched with 100 mL H$_2$O. The aqueous solution was extracted three times with Et$_2$O. The combined organic layers were dried over MgSO$_4$, filtered and the solvent was removed under reduced pressure. The pure produced was obtained after column chromatography (LM: toluene) and recrystallization from hexane. Yield: 8.3 g (66%). $^1$H NMR (CDCl$_3$): δ 7.30 (d, J$_{HH}$=7.8 Hz, 2H, Ar), 7.09 (t, J$_{HH}$=7.8 Hz, 1H, Ar), 6.04 (s, 4H, Pyr), 5.26 (s, 1H, OH), 2.57 (sep, J$_{HH}$=6.8 Hz, 4H, CH(CH$_3$)$_2$), 1.11 (d, J$_{HH}$=6.8 Hz, 12H, CH(CH$_3$)$_2$), 1.04 (d, J$_{HH}$=6.8 Hz, 12H, CH(CH$_3$)$_2$) ppm. Anal. Calc. (%) for C$_{26}$H$_{36}$N$_2$O: C, 79.55; H, 9.24; N, 7.14. Found: C, 79.49; H, 9.27; N, 7.11.

2,6-bis(2,5-diphenylpyrrolyl)phenol (DPP$^{Ph}$OH): The reaction was performed in the same manner as DPP$^{iPr}$OH. The pure product was obtained after column chromatography (LM: toluene) and recrystallization from iPrOH. Yield: 887 mg (46%). $^1$H NMR (CDCl$_3$): δ 7.15 (m, 12H, Ph), 7.08 (d, J$_{HH}$=7.8 Hz, 2H, Ar), 6.96 (m, 8H, Ph), 6.75 (t, J$_{HH}$=7.8 Hz, 1H, Ar), 6.40 (s, 4H, Pyr), 4.85 (s, 3H, OH) ppm. Anal. Calc. (%) for C$_{38}$H$_{28}$N$_2$O: C, 86.34; H, 5.34; N, 5.30. Found: C, 85.99; H, 5.50; N, 5.28.

Mo(NAd)(CHCMe$_2$Ph)(Pyr)(ODPP$^{Ph}$) (1a): In a J-Young tube Mo(NAd)(CHCMe$_2$Ph)(Pyr)$_2$ (100 mg, 0.2 mmol) and DPP$^{Ph}$OH (104 mg, 0.2 mmol) was combined and 2 mL C$_6$D$_6$ was added. The resulting solution was heated at 80° C. for 60 min, and the completeness of the reaction was confirmed by $^1$H-NMR spectroscopy. The solvent was removed, and the residue was extracted with toluene, filtered through Celite and covered with a layer of pentane. After 18 h at −30° C. a yellow powder was isolated: Yield: 113 mg (59%). $^1$H NMR (C$_6$D$_6$): δ 12.29 (s, 1H, Mo═CH, JCH=121.4 Hz), 7.34 (m, 2H, Ar), 7.24-6.96 (m, 25H, Ar), 6.74 (m, 2H, Ar), 6.65 (m, 2H, Ar), 6.56 (m, 4H, Ar), 6.11 (m, 1H, Ar), 1.78 (s, 3H, Mo═CHCMe2Ph), 1.73 (m, 8H, NAd), 1.50 (s, 3H, Mo═CHCMe2Ph), 1.33 (m, 7H, NAd) ppm. $^{13}$C NMR (C$_6$D$_6$): δ 283.6 (Mo═C), 158.5, 148.9, 138.4, 138.0, 133.6, 133.5, 133.0, 131.8, 131.6, 128.8, 128.7, 128.5, 128.2, 128.1, 126.9, 126.6, 126.4, 120.4, 112.2, 111.1, 110.4, 77.6, 52.3, 43.7, 35.7, 32.5, 31.1, 29.8 ppm. Anal. Calc. (%) for C$_{62}$H$_{58}$MoN$_4$O: C, 76.68; H, 6.02; N, 5.77. Found: C, 76.47; H, 6.31; N, 5.58.

Mo(NAd)(CHCMe$_2$Ph)(Pyr)(ODPP$^{iPr}$) (1b): In a J-Young tube Mo(NAd)(CHCMe$_2$Ph)(Pyr)$_2$ (100 mg, 0.2 mmol) and DPP$^{iPr}$OH (78.5 mg, 0.2 mmol) was combined and 2 mL C$_6$D$_6$ was added. The resulting solution was stored at RT for 4 h. The completeness of the reaction was confirmed by $^1$H-NMR spectroscopy. The solvent was removed, and the residue was extracted with toluene, filtered through Celite and covered with a layer of pentane. After 18 h at −30° C. a yellow solid was isolated: Yield: 123 mg (74%). $^1$H NMR (C$_6$D$_6$): δ 12.32 (s, 1H, Mo═CH, JCH=122.1 Hz), 7.43 (m, 2H, Ar), 7.27-7.20 (m, 5H, Ar), 7.12 (m, 1H, Ar), 6.98 (m, 4H, Ar), 6.62 (t, 2H, NC2H4), 6.55 (t, 2H, NC2H4), 6.22 (d, 2H, iPr$_2$pyrr), 6.15 (d, 2H, iPr$_2$pyrr), 2.84 (m, 2H, CH(CH$_3$)$_2$), 2.71 (m, 2H, CH(CH$_3$)$_2$), 1.91 (m, 9H, NAd), 1.80 (s, 3H, Mo═CHCMe2Ph), 1.67 (s, 3H, Mo═CHCMe2Ph), 1.49 (m, 6H, NAd), 1.16 (m, 12H, CH(CH$_3$)$_2$), 1.03 (d, 6H, CH(CH$_3$)$_2$), 0.99 (d, 6H, CH(CH$_3$)$_2$) ppm. $^{13}$C NMR (C$_6$D$_6$): δ 290.2 (Mo═C), 157.7, 149.4, 140.3, 139.7, 133.3, 132.7, 130.7, 128.5, 127.0, 126.4, 120.7, 77.4, 52.3, 44.1, 35.9, 32.4, 32.2, 29.9, 26.7, 26.4, 23.6, 23.2, 23.0, 22.3 ppm. Anal. Calc. (%) for C$_{50}$H$_{66}$MoN$_4$O: C, 71.92; H, 7.97; N, 6.71. Found: C, 71.92; H, 7.94; N, 6.68.

Mo(NAd)(CHCMe$_2$Ph)(Me$_2$Pyr)(ODPP$^{Ph}$) (2a): The reaction was performed as reported for 1a, but the reaction time was 4 h at 80° C. Yield: 92 mg (52%). $^1$H NMR (C$_6$D$_6$): δ 12.06 (s, 1H, Mo═CH, JCH=121.7 Hz), 7.26 (m, 6H, Ar), 7.22-7.08 (m, 19H, Ar), 6.87 (d, 2H, Ar), 6.60 (s, 4H, Pyrr), 6.31 (bs, 2H, pyrr), 6.23 (t, 1H, Ar), 2.11 (bs, 6H, Me$_2$Pyrr), 2.04 (s, 3H, Mo═CHCMe2Ph), 1.98-183 (m, 9H, NAd), 1.52 (s, 3H, Mo═CHCMe2Ph), 1.43 (m, 6H, NAd) ppm. $^{13}$C NMR (C$_6$D$_6$): δ289.8 (Mo═C), 158.8, 149.0, 137.3, 137.2, 133.6, 133.5, 132.0, 131.6, 128.7, 128.6, 128.3, 128.2, 126.9, 126.6, 126.5, 126.4, 126.2, 120.3, 112.2, 111.3, 77.9, 52.7, 44.0, 35.8, 34.0, 31.9, 29.9 ppm. Anal. Calc. (%) for C$_{64}$H$_{62}$MoN$_4$O: C, 76.93; H, 6.25; N, 5.61. Found: C, 77.29; H, 6.30; N, 5.53.

Mo(NAr)(CHCMe$_2$Ph)(Me$_2$Pyr)(ODPP$^{Ph}$) (2b): The reaction was performed as reported for 1a, but the reaction time was 7 d at 80° C. Yield: 115 mg (63%). $^1$H NMR (C$_6$D$_6$): δ 12.48 (s, 1H, Mo═CH, JCH=122.1 Hz), 7.30-6.91 (m, 28H, Ar), 6.69 (d, 2H, Ar), 6.61 (d, 2H, pyrr), 6.54 (d, 2H, pyrr), 6.16 (bs, 1H, pyrr), 6.08 (t, 1H, Ar), 5.90 (bs, 1H, pyrr), 3.61 (m, 1H, CH(CH$_3$)$_2$), 2.96 (m, 1H, CH(CH$_3$)$_2$), 1.85 (s, 6H, Me$_2$Pyrr), 1.80 (s, 3H, Mo═CHCMe2Ph), 1.48 (s, 3H, Mo═CHCMe2Ph), 1.06 (d, 6H, CH(CH$_3$)$_2$) 0.95 (m, 6H, CH(CH$_3$)$_2$) ppm. $^{13}$C NMR (C$_6$D$_6$): δ 296.8 (Mo═C), 158.8, 153.5, 151.3, 147.3, 146.2, 133.4, 133.3, 132.4, 131.8, 128.7, 128.6, 127.9, 127.7, 126.3, 126.2, 126.1, 123.6, 122.9, 125.0, 113.3, 112.0, 109.7, 109.5, 56.5, 33.0, 30.1, 29.2, 27.1, 25.2, 24.8, 23.4, 22.5, 18.0, 15.5, 14.0 ppm. Anal. Calc. (%) for C$_{66}$H$_{64}$MoN$_4$O: C, 77.32; H, 6.29; N, 5.46. Found: C, 77.25; H, 6.45; N, 5.25.

Mo(NAr)(CHCMe$_2$Ph)(Pyr)(ODPP$^{Ph}$) (3a): The reaction was performed as reported for 1a. Yield: 128 mg (69%). $^1$H NMR (C$_6$D$_6$): δ 12.32 (s, 1H, Mo═CH, JCH=121.5 Hz), 7.39-6.93 (m, 27H, Ar), 6.75 (d, 2H, Ar), 6.55 (d, 2H, pyrr), 6.48 (d, 2H, pyrr), 6.28 (m, 4H, pyrr), 6.11 (t, 1H, Ar), 3.32 (m, 2H, CH(CH$_3$)$_2$), 1.60 (s, 3H, Mo═CHCMe2Ph), 1.35 (s, 3H, Mo═CHCMe2Ph), 1.67 (d, 6H, CH(CH$_3$)$_2$), 1.03 (d, 6H, CH(CH$_3$)$_2$) ppm. $^{13}$C NMR (C$_6$D$_6$): δ 294.6 (Mo═C), 158.1, 154.2, 147.3, 147.1, 137.9, 137.8, 134.1, 133.4, 132.8, 131.9, 131.6, 129.0, 128.6, 128.4, 128.3, 127.5, 126.7, 126.6, 126.5, 126.3, 123.1, 120.7, 112.4, 12.0, 110.2, 56.8, 31.0, 30.2, 28.9, 24.5, 23.4 ppm. Anal. Calc. (%) for C$_{64}$H$_{62}$MoN$_4$O: C, 76.93; H, 6.25; N, 5.61. Found: C, 7.33; H, 6.06; N, 5.54.

Mo(NAr)(CHCMe$_2$Ph)(Pyr)(ODPP$^{iPr}$) (3b): The reaction was performed as reported for 1b. Yield: 116 mg (72%). $^1$H NMR (C$_6$D$_6$): δ 13.01 (s, 1H, Mo═CH, JCH=122.9 Hz), 7.41 (m, 2H, Ar), 7.27 (m, 2H, Ar), 7.21 (m, 2H, Ar), 7.11 (m, 1H, Ar), 7.02-6.96 (m, 4H, Ar), 6.54 (t, 2H, NC2H4), 6.36 (t, 2H, NC2H4), 6.24 (m, 4H, iPr$_2$pyrr), 3.52 (m, 2H, CH(CH$_3$)$_2$), 2.79 (m, 2H, CH(CH$_3$)$_2$), 2.73 (m, 2H, CH(CH$_3$)$_2$), 1.80 (s, 3H, Mo═CHCMe2Ph), 1.65 ((s, 3H, Mo═CHCMe2Ph), 1.29 (m, 12H, CH(CH$_3$)$_2$), 1.10 (m, 12H, CH(CH$_3$)$_2$), 1.00 (m, 12H, CH(CH$_3$)$_2$) ppm. $^{13}$C NMR (C$_6$D$_6$): δ 298.5 (Mo═C), 157.4, 153.7, 147.9, 140.3, 139.9, 133.1, 131.3, 131.2, 128.7, 127.7, 126.7, 126.6, 123.5, 121.0, 110.4, 104.4, 103.8, 56.1, 31.1, 30.9, 25.8, 26.8, 26.3, 24.7, 24.4, 23.8, 23.2, 22.7, 22.1 ppm. Anal. Calc. (%) for C$_{52}$H$_{68}$MoN$_4$O: C, 72.53; H, 7.96; N, 6.51. Found: C, 72.34; H, 7.95; N, 6.55.

W(NAr)(CH-t-Bu)(pyr)(ODPP$^{Ph}$) (4a). A vessel containing a suspension of W(NAr)(CH-t-Bu)(pyr)$_2$(dme) (47.6 mg, 0.0731 mmol) and 2,6-bis(2,5-diphenyl-N-pyrrolyl) phenol (38.6 mg, 0.0731 mmol) in C$_6$H$_6$ was placed in a sonicator bath for 48 hours. All volatiles were removed in vacuo and the residue was extracted with pentane (5 mL) to provide the crude product. Recrystallization from toluene and pentane yielded the product as a yellow-orange crystalline solid (46.1 mg, 62% yield). $^1$H NMR (500 MHz, C$_6$D$_6$, 25° C.) δ 9.17 (br s, 1H, W═CH), 7.27 (m, 4H, Ar), 7.07-6.95 (m, 15H, Ar), 6.87 (m, 4H, Ar), 6.67 (d, J=8.0 Hz, 2H, Ar), 6.51-6.45 (m, 6H, Ar), 6.28 (m, 2H, Ar), 6.06 (t, J=8.0 Hz, 1H, Ar) δ 3.30 (sept, J=6.8 Hz, 2H, CH(CH$_3$)$_2$), 1.25 (d, J=6.8 Hz, 6H, CH(CH$_3$)$_2$), 1.00 (d, J=6.8 Hz, 6H, CH(CH$_3$)$_2$), 0.94 (s, 9H, $^t$Bu). $^{13}$C{$^1$H} NMR (125 MHz, C$_6$D$_6$, 25° C.) δ 264.92 (W═CHR), 157.38, 152.36, 145.70, 137.74, 137.58, 135.24, 134.00, 133.22, 131.86, 131.65, 129.06, 128.81, 128.60, 128.55, 128.45, 128.35, 127.45, 126.78, 126.46, 122.74, 121.71, 112.75, 112.04, 111.49, 48.44, 32.60, 28.57, 24.45, 23.31. Anal. Calc. (%) for C$_{59}$H$_{58}$N$_4$OW: C, 69.27; H, 5.71; N, 5.48. Found: C, 69.18; H, 5.78; N, 5.37.

W(NAr)(CH-t-Bu)(pyr)(ODPP$^{iPr}$) (4b). A vessel containing a solution of W(NAr)(CH-t-Bu)(pyr)$_2$(dme) (48.6 mg, 0.0746 mmol) and 2,6-bis(2,5-diisopropyl-N-pyrrolyl)phenol (29.3 mg, 0.0746 mmol) in C$_6$H$_6$ was heated at 60° C. for 16 hours. All volatiles were removed in vacuo and the residue was triturated with cold pentane (5 mL) to provide the crude product. Recrystallization from pentane yielded the product as a yellow-orange crystalline solid (24.9 mg, 38% yield). $^1$H NMR (500 MHz, C$_6$D$_6$, 25° C.) δ 10.02 (br s, 1H, W=CH), 7.06 (m, 2H, Ar), 6.98 (m, 1H, Ar), 6.91 (m, 2H, Ar), 6.78 (m, 2H, Ar), 6.54 (t, J=7.9 Hz, 1H, Ar), 6.36 (m, 2H, Ar), 6.17 (m, 4H, Ar), 3.58 (br s, 2H, N(Ar) CH(CH$_3$)$_2$), 2.72-2.55 (m, 4H, ODPP CH(CH$_3$)$_2$), 1.33 (d, J=6.8 Hz, 6H, CH(CH$_3$)$_2$), 1.25-1.17 (m, 15H, CH(CH$_3$)$_2$ and $^t$Bu), 1.09 (d, J=6.8 Hz, 6H, CH(CH$_3$)$_2$), 1.01 (d, J=6.5 Hz, 6H, CH(CH$_3$)$_2$), 0.93 (m, 12H, CH(CH$_3$)$_2$). $^{13}$C{$^1$H} NMR (125 MHz, C$_6$D$_6$, 25° C.) δ 268.61 (W=CHR), 157.34, 152.13, 140.35, 139.75, 135.41, 131.44, 131.17, 126.31, 123.11, 122.01, 111.77, 104.58, 104.41, 103.91, 47.17, 33.03, 28.25, 26.83, 26.26, 24.71, 24.22, 23.80, 23.35, 22.71, 21.96. Anal. Calc. (%) for C$_{47}$H$_{66}$N$_4$OW: C, 63.65; H, 7.50; N, 6.32. Found: C, 63.29; H, 7.38; N, 6.13.

W(NAr)(C$_3$H$_6$)(pyr)(ODPP$^{Ph}$) (5). A solution of W(NAr)(CH-t-Bu)(pyr)(ODPP$^{Ph}$) in C$_6$D$_6$ was subjected to three freeze-pump-thaw cycles and treated with ethylene (1 atm). After 16 hours, the solution was lyophilized to quantitatively afford the product as a light yellow solid. $^1$H NMR (500 MHz, C$_6$D$_6$, 25° C.) δ 7.43-6.47 (m, 31H, Ar), 6.22 (t, J=7.9 Hz, 1H, Ar), 5.82 (m, 2H, Ar), 4.46 (m, $^1$J$_{CH}$=160 Hz, 2H, α-CH$_2$), 3.87 (sept, J=6.5 Hz, 2H, CH(CH$_3$)$_2$), 3.49 (m, $^1$J$_{CH}$=150 Hz, 2H, α-CH$_2$), 1.13 (m, 12H, CH(CH$_3$)$_2$), −0.78 (m, $^1$J$_{CH}$=155 Hz, 1H, β-CH$_2$), −1.38 (m, $^1$J$_{CH}$=155 Hz, 1H, β-CH$_2$). $^1$J$_{CH}$ values were obtained by preparing a sample with $^{13}$C labeled ethylene. $^{13}$C{$^1$H} NMR (125 MHz, C$_6$D$_6$, 25° C.) δ 157.50, 149.03, 146.99, 137.90, 133.33, 131.89, 130.54, 129.33, 128.81, 128.62, 128.57, 128.45, 126.83, 126.28, 125.70, 123.00, 118.59, 111.87, 109.49, 99.99, 28.33, 24.66, 21.45 (C$_α$), −4.24 (C$_β$). Anal. Calc. (%) for C$_{57}$H$_{54}$N$_4$OW: C, 68.81; H, 5.47; N, 5.63. Found: C, 68.44; H, 5.35; N, 5.18.

ROMP of DCMNBD: For a standard ROMP procedure, 100 mg (0.48 mmol) DCMNBD was dissolved in about 1 ml toluene and added to a solution 2% of the isolated catalyst dissolved in about 1 ml toluene. After the reaction was completed (checked by $^1$H-NMR) the polymer was isolated by drop wise adding the reaction mixture into a stirred MeOH solution. After 1 h the polymer was filtered off, washed with MeOH and dried in vacuo. The purity and tacticity of the compound was proven by $^1$H and $^{13}$C NMR spectroscopy.

Homocoupling of 1-octene. The procedure was adapted from Jiang et al (Jiang, A. J.; Zhao, Y.; Schrock, R. R.; Hoveyda, A. H. *J. Am. Chem. Soc.* 2009, 131, 16630). 1-octene (10 μL, 0.064 mmol) was added via syringe to a solution of an olefin metathesis catalyst (2.5 μmol) in benzene (200 μL). An internal standard is also added to the reaction mixture (trimethoxybenzene or mesitylene). The solution was stirred at room temperature in 0.5 dram vials, with the cap loosely screwed on. The progress of the reaction was monitored by aliquots taken at 10, 40, 110 and 400 minutes from the onset of the reaction. Aliquots were taken directly from the reaction mixture and added to an NMR tube, where they were quenched by moist CDCl$_3$. Z-selectivity was determined by integrating the resonances corresponding to cis- and trans-7-tetradecene.

Crystallographic details. Low-temperature diffraction data (φ- and ω-scans) were collected on a Bruker D8 three-circle diffractometer coupled to a Bruker-AXS Smart Apex CCD detector with graphite-monochromated Cu Kα radiation (λ=1.54178 Å) for the structures of compounds 3a and 3b and on a Bruker-AXS X8 Kappa Duo diffractometer coupled to a Smart Apex2 CCD detector with Mo Kα radiation (λ=0.71073 Å) from an Incoatec IμS micro-source for the structure of compound 5. The structures were solved by direct methods using SHELXS (Sheldrick, G. M., *Acta Cryst.* 1990, A46, 467-473) and refined against F$^2$ on all data by full-matrix least squares with SHELXL-97 (Sheldrick, G. M., *Acta Cryst.* 2008, A64, 112-122) following established refinement strategies (Müller, P. *Crystallography Reviews* 2009, 15, 57-83). All non-hydrogen atoms were refined anisotropically. Except for hydrogen atoms on carbon atoms in direct contact with the metal (for details see below), all hydrogen atoms were included into the model at geometrically calculated positions and refined using a riding model. The isotropic displacement parameters of all hydrogen atoms were constrained to 1.2 times the U$_{eq}$ value of the atoms they are linked to (1.5 times for methyl groups). Details of the data quality, a summary of the residual values of the refinements as well as all other pertinent parameters are listed in Tables Si to S15.

Compound 3a crystallizes in the orthorhombic space group P2$_1$2$_1$2$_1$ with one molecule of 3a and one benzene molecule in the asymmetric unit. Coordinates for the hydrogen atom on C1, that is the carbon atom directly binding to the metal, were taken from the difference Fourier synthesis. The hydrogen atoms were subsequently refined semi-freely with the help of a distance restraint on the C—H-distance (target 0.95(2) Å).

TABLE 2

Crystal data and structure refinement for 3a.

| | |
|---|---|
| Identification code | d10107 |
| Empirical formula | C$_{72}$H$_{70}$MoN$_4$O |
| Formula weight | 1103.26 |
| Temperature | 100(2) K |
| Wavelength | 1.54178 Å |
| Crystal system | Orthorhombic |
| Space group | P2$_1$2$_1$2$_1$ |
| Unit cell dimensions | a = 12.2807(2) Å    α = 90°. |
| | b = 20.2298(3) Å    β = 90°. |
| | c = 23.4545(3) Å    γ = 90°. |
| Volume | 5826.94(15) Å$^3$ |
| Z | 4 |
| Density (calculated) | 1.258 Mg/m$^3$ |
| Absorption coefficient | 2.205 mm$^{-1}$ |
| F(000) | 2320 |
| Crystal size | 0.20 × 0.20 × 0.10 mm$^3$ |
| Theta range for data collection | 2.88 to 70.04°. |
| Index ranges | −14 <= h <= 14, −24 <= k <= 24, −28 <= l <= 28 |
| Reflections collected | 119291 |
| Independent reflections | 11008 [R$_{int}$ = 0.0445] |
| Completeness to theta = 70.04° | 99.8% |
| Absorption correction | Semi-empirical from equivalents |
| Max. and min. transmission | 0.8097 and 0.6669 |
| Refinement method | Full-matrix least-squares on F$^2$ |
| Data/restraints/parameters | 11008/1/714 |
| Goodness-of-fit on F$^2$ | 1.059 |
| Final R indices [I > 2σ(I)] | R1 = 0.0266, wR2 = 0.0693 |
| R indices (all data) | R1 = 0.0274, wR2 = 0.0700 |
| Absolute structure parameter | −0.015(4) |
| Largest diff. peak and hole | 0.891 and −0.348 e · Å$^{-3}$ |

Compound 3b crystallizes in the monoclinic space group P2$_1$/c with one molecule of 3b and one pentane molecule in the asymmetric unit. Coordinates for the hydrogen atom on C1, that is the carbon atom directly binding to the metal, were taken from the difference Fourier synthesis. The hydrogen atoms were subsequently refined semi-freely with the help of a distance restraint on the C—H-distance (target 0.95(2) Å).

TABLE 3

Crystal data and structure refinement for 3b.

| | |
|---|---|
| Identification code | d10099 |
| Empirical formula | $C_{57}H_{80}MoN_4O$ |
| Formula weight | 933.19 |
| Temperature | 100(2) K |
| Wavelength | 1.54178 Å |
| Crystal system | Monoclinic |
| Space group | $P2_1/c$ |
| Unit cell dimensions | a = 19.1624(4) Å   α = 90°. |
| | b = 15.9182(3) Å   β = 99.7440(10)°. |
| | c = 17.2741(3) Å   γ = 90°. |
| Volume | 5193.12(17) Å$^3$ |
| Z | 4 |
| Density (calculated) | 1.194 Mg/m$^3$ |
| Absorption coefficient | 2.370 mm$^{-1}$ |
| F(000) | 2000 |
| Crystal size | 0.45 × 0.30 × 0.10 mm$^3$ |
| Theta range for data collection | 2.34 to 69.32°. |
| Index ranges | −23 <= h <= 23, −19 <= k <= 19, |
| | −20 <= l <= 20 |
| Reflections collected | 103056 |
| Independent reflections | 9721 [$R_{int}$ = 0.0314] |
| Completeness to theta = 69.32° | 99.9% |
| Absorption correction | Semi-empirical from equivalents |
| Max. and min. transmission | 0.7975 and 0.4152 |
| Refinement method | Full-matrix least-squares on F$^2$ |
| Data/restraints/parameters | 9721/1/585 |
| Goodness-of-fit on F$^2$ | 1.026 |
| Final R indices [I > 2σ(I)] | R1 = 0.0251, wR2 = 0.0645 |
| R indices (all data) | R1 = 0.0261, wR2 = 0.0653 |
| Largest diff. peak and hole | 0.506 and −0.457 e · Å$^{-3}$ |

Crystals of 5 were grown from a mixture of toluene and pentane at −20° C. The compound crystallized in the triclinic space group P-1 with one molecule in the asymmetric unit. Coordinates for the metallacycle hydrogen atoms were taken from the difference Fourier synthesis and the hydrogen atoms were subsequently refined semi-freely with the help of a distance restraint on the C—H distance (target 0.99(2) Å). The largest residual election density was modeled as a second tungsten position and the relative occupancy of the two components refined to 0.9367(12). Residual electron density proximal to the pyrrolide and alkoxide was observed in the difference Fourier synthesis but attempts to model as two part disorder failed to achieve a stable refinement.

TABLE 4

Crystal data and structure refinement for 5

| | |
|---|---|
| Identification code | x8_12204 |
| Empirical formula | C57H54N4OW |
| Formula weight | 994.89 |
| Temperature | 100(2) K |
| Wavelength | 0.71073 Å |
| Crystal system | Triclinic |
| Space group | P-1 |
| Unit cell dimensions | a = 13.2795(6) Å   α = 62.0830(10)°. |
| | b = 13.6061(6) Å   β = 81.7030(10)°. |
| | c = 14.0913(7) Å   γ = 86.4550(10)°. |
| Volume | 2226.16(18) Å$^3$ |
| Z | 2 |
| Density (calculated) | 1.484 Mg/m$^3$ |
| Absorption coefficient | 2.641 mm$^{-1}$ |
| F(000) | 1012 |
| Crystal size | 0.30 × 0.23 × 0.19 mm$^3$ |
| Theta range for data collection | 1.55 to 31.59°. |
| Index ranges | −19 <= h <= 19, −20 <= k <= 17, |
| | −20 <= l <= 20 |
| Reflections collected | 112060 |
| Independent reflections | 14786 [R(int) = 0.0403] |
| Completeness to theta = 31.59° | 99.1% |
| Absorption correction | Semi-empirical from equivalents |
| Max. and min. transmission | 0.6296 and 0.5006 |

TABLE 4-continued

Crystal data and structure refinement for 5

| | |
|---|---|
| Refinement method | Full-matrix least-squares on F$^2$ |
| Data/restraints/parameters | 14786/6/596 |
| Goodness-of-fit on F$^2$ | 1.078 |
| Final R indices [I > 2sigma(I)] | R1 = 0.0246, wR2 = 0.0565 |
| R indices (all data) | R1 = 0.0290, wR2 = 0.0579 |
| Largest diff. peak and hole | 1.132 and −0.650 e · Å$^{-3}$ |

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The invention claimed is:

1. A compound of formula I:

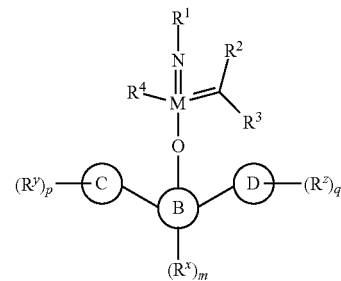

wherein:

M is molybdenum or tungsten;

R$^1$ is an optionally substituted group selected from C$_{1-20}$ aliphatic, C$_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

each of $R^2$ and $R^3$ is independently R', —OR', —SR', —N(R')$_2$, —OC(O)R', —SOR', —SO$_2$R', —SO$_2$N(R')$_2$, —C(O)N(R')$_2$, —NR'C(O)R', or —NR'SO$_2$R';

m is 0-3;

Ring B is an optionally substituted group selected from phenyl or a 5-6 membered monocyclic heteroaryl ring having 1-4 heteroatoms independently selected from nitrogen, oxygen, or sulfur;

each of p and q is independently 0-4;

each of Ring C and Ring D is independently an optionally substituted 5-membered monocyclic heteroaryl ring having 1-4 nitrogen atoms;

each of $R^x$, $R^y$ and $R^z$ is independently halogen, —OR', —N(R')$_2$, —NR'C(O)R', —NR'C(O)OR', —NR'C(O)N(R')$_2$, —NR'SO$_2$R', —NR'SO$_2$N(R')$_2$, —NR'OR', or an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

$R^4$ is an optionally substituted 5-membered monocyclic heteroaryl ring having 1-2 nitrogen atoms; and each R' is independently hydrogen or an optionally substituted group selected from $C_{1-6}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or:

two R' groups on the same nitrogen atom are optionally taken together with the nitrogen atom to form an optionally substituted 3-8 membered, saturated, partially unsaturated, or aryl ring having 1-4 heteroatoms independently selected from nitrogen, oxygen, or sulfur.

2. The compound of claim 1, wherein one of $R^2$ and $R^3$ is hydrogen and the other is optionally substituted $C_{1-20}$ aliphatic.

3. A compound of formula II:

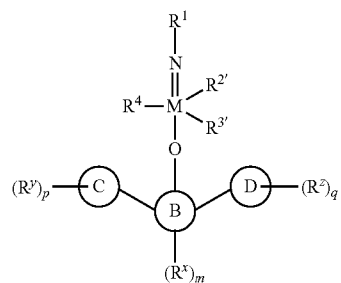

wherein:

M is molybdenum or tungsten;

$R^1$ is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

$R^{2'}$ and $R^{3'}$ are taken together with their intervening metal atoms to form an optionally substituted 3-8 membered saturated or partially unsaturated ring having, in addition to the intervening metal atom, 0-4 heteroatoms independently selected from nitrogen, oxygen, or sulfur;

m is 0-3;

Ring B is an optionally substituted group selected from phenyl or a 5-6 membered monocyclic heteroaryl ring having 1-4 heteroatoms independently selected from nitrogen, oxygen, or sulfur;

each of p and q is independently 0-4;

each of Ring C and Ring D is independently an optionally substituted 5-membered monocyclic heteroaryl ring having 1-4 nitrogen atoms;

each of $R^x$, $R^y$ and $R^z$ is independently halogen, —OR', —N(R')$_2$, —NR'C(O)R', —NR'C(O)OR', —NR'C(O)N(R')$_2$, —NR'SO$_2$R', —NR'SO$_2$N(R')$_2$, —NR'OR', or an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

$R^4$ is an optionally substituted 5-membered monocyclic heteroaryl ring having 1-2 nitrogen atoms; and each R' is independently hydrogen or an optionally substituted group selected from $C_{1-6}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or:

two R' groups on the same nitrogen atom are optionally taken together with the nitrogen atom to form an optionally substituted 3-8 membered, saturated, partially unsaturated, or aryl ring having 1-4 heteroatoms independently selected from nitrogen, oxygen, or sulfur.

4. The compound of claim 3, wherein the compound has the structure of formula II-a:

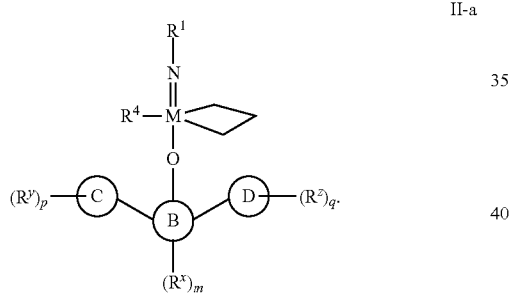

II-a

5. The compound of claim 1, wherein $R^1$ is optionally substituted $C_{1-20}$ aliphatic.

6. The compound of claim 1, wherein $R^1$ is optionally substituted phenyl.

7. The compound claim 1, wherein $R^1$ is selected from

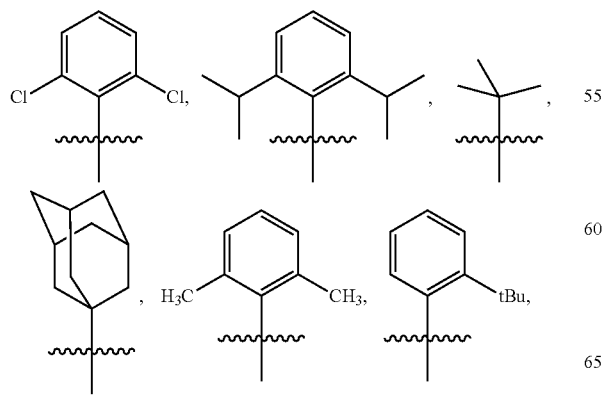

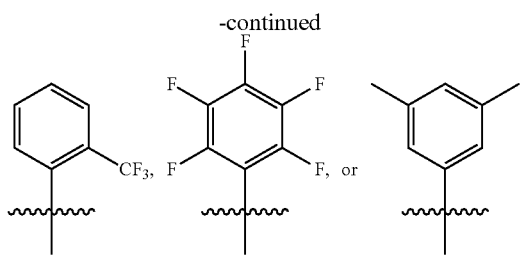

8. The compound of claim 1, wherein $R^4$ is optionally substituted pyrrolyl.

9. The compound of claim 1, wherein the compound is selected from

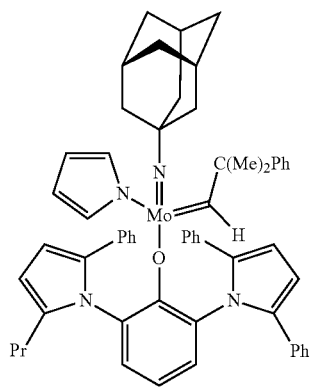

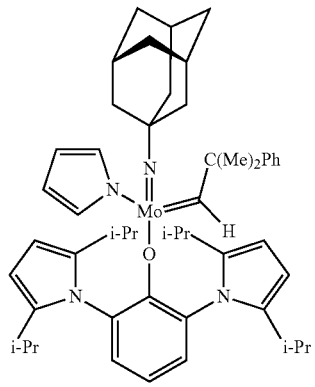

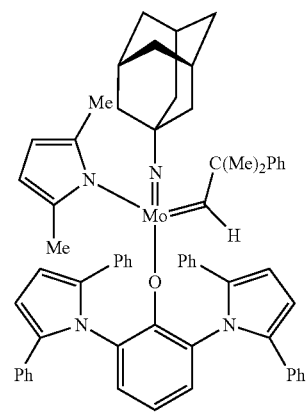

-continued

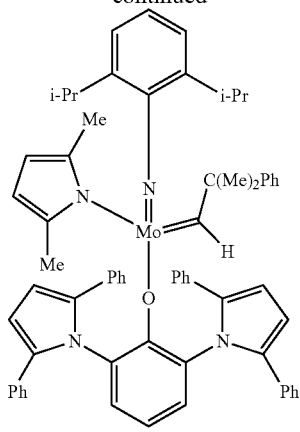

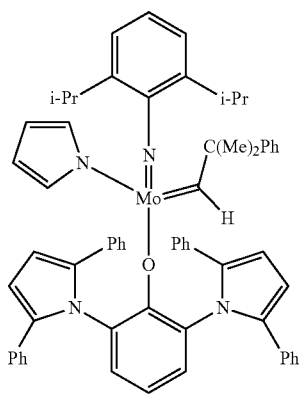

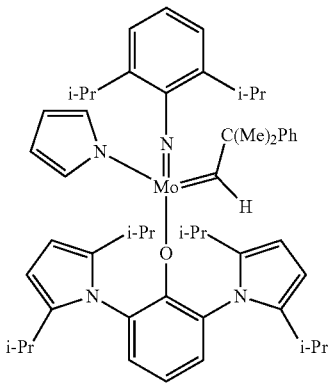

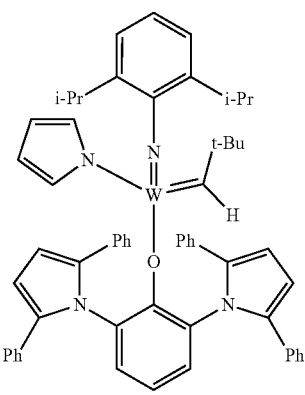

-continued

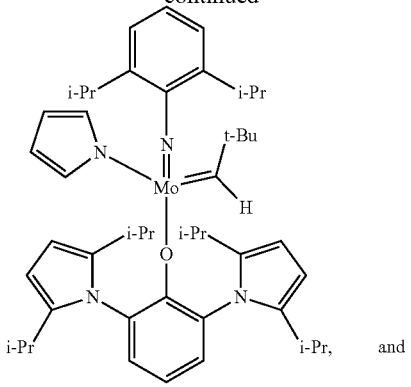

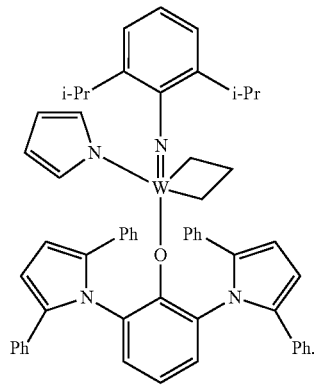

and

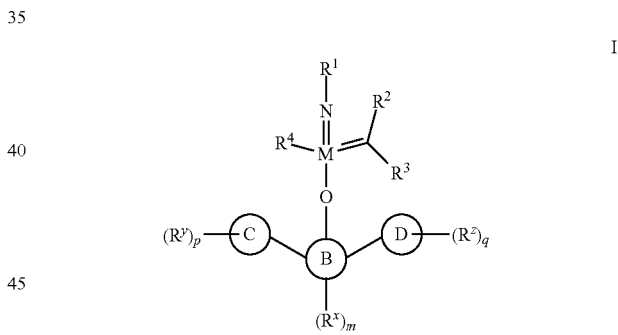

10. A method comprising:
(a) providing a compound of formula I:

I wherein:
M is molybdenum or tungsten;
$R^1$ is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

each of R² and R³ is independently R', —OR', —SR', —N(R')₂, —OC(O)R', —SOR', —SO₂R', —SO₂N(R')₂, —C(O)N(R')₂, —NR'C(O)R', or —NR'SO₂R';

m is 0-3;

Ring B is an optionally substituted group selected from phenyl or a 5-6 membered monocyclic heteroaryl ring having 1-4 heteroatoms independently selected from nitrogen, oxygen, or sulfur;

each of p and q is independently 0-4;

each of Ring C and Ring D is independently an optionally substituted 5-membered monocyclic heteroaryl ring having 1-4 nitrogen atoms;

each of $R^x$, $R^y$ and $R^z$ is independently halogen, —OR', —N(R')₂, —NR'C(O)R', —NR'C(O)OR', —NR'C(O)N(R')₂, —NR'SO₂R', —NR'SO₂N(R')₂, —NR'OR', or an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

R⁴ is an optionally substituted 5-membered monocyclic heteroaryl ring having 1-2 nitrogen atoms; and each R' is independently hydrogen or an optionally substituted group selected from $C_{1-6}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or:

two R' groups on the same nitrogen atom are optionally taken together with the nitrogen atom to form an optionally substituted 3-8 membered, saturated, partially unsaturated, or aryl ring having 1-4 heteroatoms independently selected from nitrogen, oxygen, or sulfur;

or a compound of formula II:

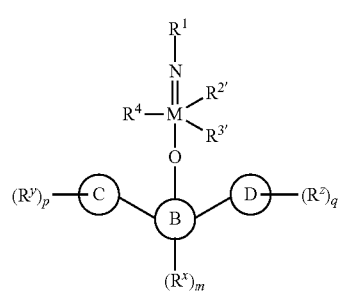

wherein:

M is molybdenum or tungsten;

R¹ is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

R²' and R³' are taken together with their intervening metal atoms to form an optionally substituted 3-8 membered saturated or partially unsaturated ring having, in addition to the intervening metal atom, 0-4 heteroatoms independently selected from nitrogen, oxygen, or sulfur;

m is 0-3;

Ring B is an optionally substituted group selected from phenyl or a 5-6 membered monocyclic heteroaryl ring having 1-4 heteroatoms independently selected from nitrogen, oxygen, or sulfur;

each of p and q is independently 0-4;

each of Ring C and Ring D is independently an optionally substituted 5-membered monocyclic heteroaryl ring having 1-4 nitrogen atoms;

each of $R^x$, $R^y$ and $R^z$ is independently halogen, —OR', —N(R')₂, —NR'C(O)R', —NR'C(O)OR', —NR'C(O)N(R')₂, —NR'SO₂R', —NR'SO₂N(R')₂, —NR'OR', or an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

$R^4$ is an optionally substituted 5-membered monocyclic heteroaryl ring having 1-2 nitrogen atoms; and each R' is independently hydrogen or an optionally substituted group selected from $C_{1-6}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or:

two R' groups on the same nitrogen atom are optionally taken together with the nitrogen atom to form an optionally substituted 3-8 membered, saturated, partially unsaturated, or aryl ring having 1-4 heteroatoms independently selected from nitrogen, oxygen, or sulfur; and (b) reacting a first compound comprising a first unsaturated carbon-carbon bond and a second compound comprising a second unsaturated carbon-carbon bond to produce a product comprising an unsaturated carbon-carbon bond.

11. The method of claim 10, wherein the compound is selected from

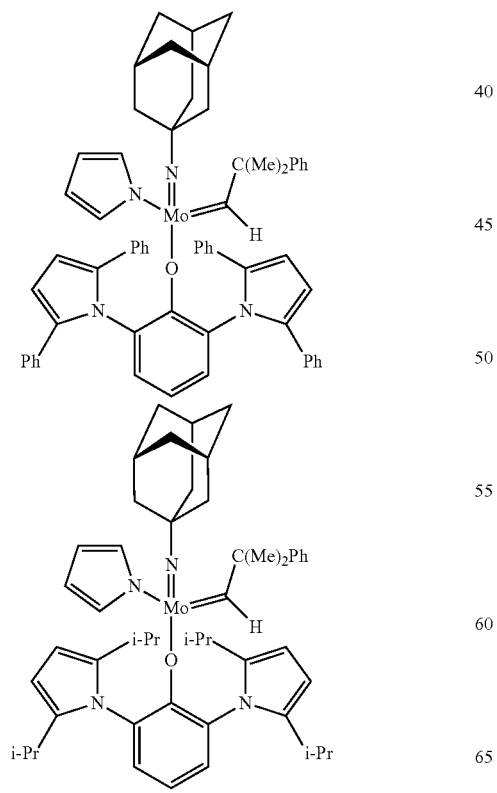

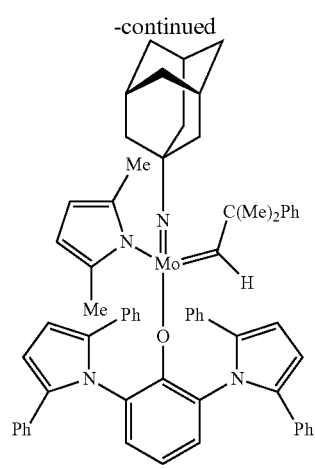

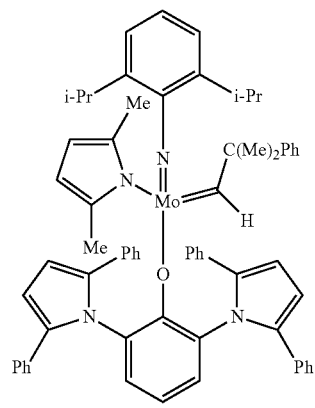

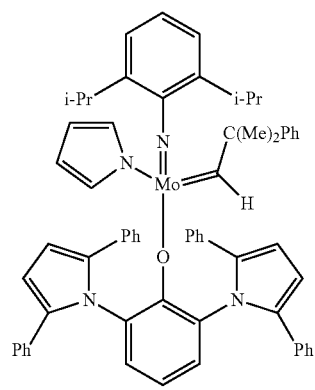

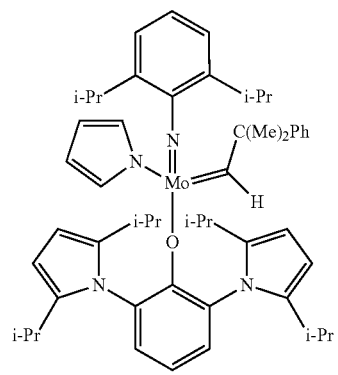

-continued
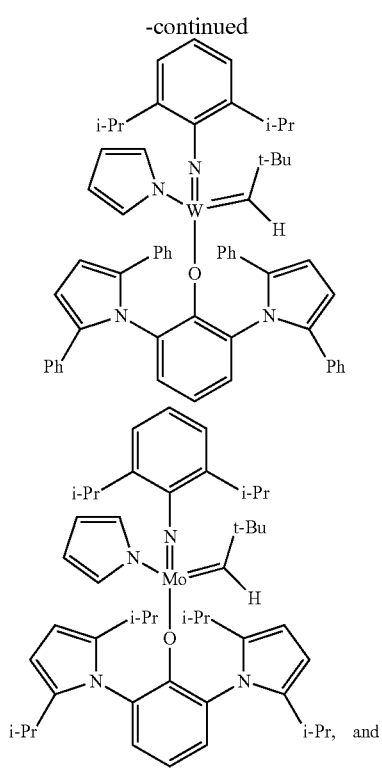
i-Pr, and
-continued
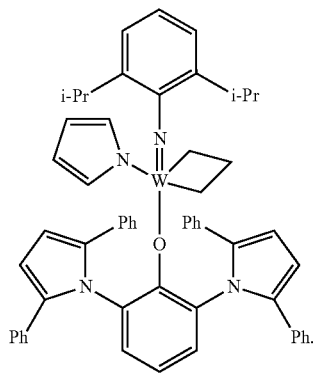
12. The method of claim 10, wherein each of the unsaturated carbon-carbon bonds is a carbon-carbon double bond.
13. The method of claim 10, wherein the product comprises a carbon-carbon double bond, and said carbon-carbon double bond is formed with Z-selectivity.
14. The method of claim 13, wherein the Z-selectivity is greater than about 90%.
* * * * *